United States Patent
Hall et al.

(10) Patent No.: US 11,913,943 B2
(45) Date of Patent: *Feb. 27, 2024

(54) BED BUGS DETECTION DEVICE

(71) Applicant: Redcoat Solutions, Inc., Rockingham, VA (US)

(72) Inventors: William John Hall, Harrisonburg, VA (US); Benedict Louis Zin, San Diego, CA (US); Andy Sturman, San Diego, CA (US); Min Wang, San Diego, CA (US)

(73) Assignee: Redcoat Solutions, Inc., Rockingham, VA (US)

( * ) Notice: Subject to any disclaimer, the term of this patent is extended or adjusted under 35 U.S.C. 154(b) by 617 days.

This patent is subject to a terminal disclaimer.

(21) Appl. No.: 16/994,322

(22) Filed: Aug. 14, 2020

(65) Prior Publication Data
US 2020/0378959 A1 Dec. 3, 2020

Related U.S. Application Data

(63) Continuation of application No. 15/331,081, filed on Oct. 21, 2016, now Pat. No. 10,823,726.

(60) Provisional application No. 62/244,188, filed on Oct. 21, 2015.

(51) Int. Cl.
| | |
|---|---|
| *G01N 33/53* | (2006.01) |
| *C07K 16/00* | (2006.01) |
| *G01N 21/84* | (2006.01) |
| *G01N 33/558* | (2006.01) |
| *G01N 33/553* | (2006.01) |
| *G01N 33/543* | (2006.01) |
| *C07K 16/18* | (2006.01) |
| *G01N 21/78* | (2006.01) |
| *G01N 33/68* | (2006.01) |
| *G01N 21/77* | (2006.01) |

(52) U.S. Cl.
CPC ......... *G01N 33/5308* (2013.01); *C07K 16/00* (2013.01); *C07K 16/18* (2013.01); *G01N 21/78* (2013.01); *G01N 21/8483* (2013.01); *G01N 33/54388* (2021.08); *G01N 33/553* (2013.01); *G01N 33/68* (2013.01); *C07K 2317/14* (2013.01); *C07K 2317/565* (2013.01); *G01N 2021/7759* (2013.01); *G01N 2201/12* (2013.01); *G01N 2333/43552* (2013.01)

(58) Field of Classification Search
CPC .... C07K 16/00; C07K 16/18; C07K 2317/14; C07K 2317/565; G01N 2021/7759; G01N 21/78; G01N 21/8483; G01N 2201/12; G01N 2333/43552; G01N 33/5308; G01N 33/54386; G01N 33/54388; G01N 33/553; G01N 33/558; G01N 33/68
See application file for complete search history.

(56) References Cited

U.S. PATENT DOCUMENTS

| | | |
|---|---|---|
| 6,319,676 B1 | 11/2001 | Nazareth et al. |
| 7,129,053 B1 | 10/2006 | Reiter et al. |
| 7,214,542 B2 | 5/2007 | Hutchinson |
| 7,220,597 B2 | 5/2007 | Zin et al. |
| 7,482,128 B2 | 6/2009 | Jensen et al. |
| 7,591,099 B2 | 9/2009 | Lang et al. |
| 7,727,734 B1 | 6/2010 | Smith |
| 7,743,552 B2 | 6/2010 | Borth et al. |
| 8,375,626 B2 | 2/2013 | Borth et al. |
| 8,435,461 B2 | 5/2013 | Kirby et al. |
| 8,460,890 B2 | 6/2013 | Smith |
| 8,551,968 B2 | 10/2013 | Refaeli et al. |
| 8,606,528 B2 | 12/2013 | Sharrock |
| 8,617,486 B2 | 12/2013 | Kirby et al. |
| 8,984,084 B2 | 3/2015 | Borth et al. |
| 9,188,583 B2 | 11/2015 | Vaidyanathan et al. |
| 9,458,512 B2 | 10/2016 | Colaizzi et al. |
| 9,500,643 B2 | 11/2016 | Vaidyanathan et al. |

(Continued)

FOREIGN PATENT DOCUMENTS

| | | |
|---|---|---|
| AU | 2013200548 B2 | 2/2013 |
| WO | WO 99/64863 A1 | 12/1999 |

(Continued)

OTHER PUBLICATIONS

Arkle, S., et al., "Antibody Detection by ELISA in Chicken Infested with *Dermanyssus gallinae*," *Epidémiol et santé anim* 48:15-19, Maisons-Alfort, France (2005).

Blow, J.A., et al., "Stercorarial Shedding and Transtadial Transmission of Hepatitis B Virus by Common Bed Bugs (*Hemiptera: Cimicidae*)" *J. Med. Entomol.* 38: 694-700, Entomological Society of America, United States (2001).

Eom, I.Y., et al., "Simultaneous sampling and analysis of indoor air infested with *Cimex lectularius* L. (*Hemiptera: Cimicidae*) by solid phase microextraction, thin film microextraction and needle trap device," *Anal Chim Acta* 716: 2-10, Elsevier B.V., The Netherlands (2012).

(Continued)

*Primary Examiner* — Galina M. Yakovleva

(74) *Attorney, Agent, or Firm* — STERNE, KESSLER, GOLDSTEIN & FOX P.L.L.C.

(57) ABSTRACT

System and method embodiments for analyzing a test fluid to detect prior or present infestations of bed bugs are described. In an embodiment, the method may include receiving the test fluid on a test strip within the detection device. The test strip may include a reaction portion and a reagent portion containing an antibody or antigen-binding fragment that is conjugated to a colored particle. The test fluid may include bed bug antigen that reacts with the conjugated antibody. The detection device may include a first and a second optical sensor for monitoring a reaction and a background color intensity, respectively. Upon a predetermined time delay elapsing, the detection device determines whether bed bug antigen is present in the test fluid using the monitored color intensities and minimum and maximum color intensity thresholds associated with bed bugs. Then, the detection device outputs a result using a visual display.

14 Claims, 30 Drawing Sheets

(56) References Cited

U.S. PATENT DOCUMENTS

| | | | |
|---|---|---|---|
| 9,549,542 | B2 | 1/2017 | Cain |
| 10,045,520 | B2 | 8/2018 | Carver et al. |
| 10,264,776 | B2 | 4/2019 | Borth et al. |
| 10,768,172 | B2 | 9/2020 | Hall et al. |
| 10,823,726 | B2 | 11/2020 | Hall et al. |
| 2004/0152208 | A1 | 8/2004 | Hutchinson |
| 2008/0311002 | A1 | 12/2008 | Kirby et al. |
| 2009/0155921 | A1 | 6/2009 | Lu et al. |
| 2010/0120061 | A1 | 5/2010 | Badwan et al. |
| 2010/0212213 | A1 | 8/2010 | Hope et al. |
| 2010/0233731 | A1 | 9/2010 | Smith |
| 2010/0273177 | A1 | 10/2010 | Piasio et al. |
| 2011/0044936 | A1 | 2/2011 | Black et al. |
| 2011/0289824 | A1 | 12/2011 | Wu et al. |
| 2012/0072125 | A1 | 3/2012 | Sharrock et al. |
| 2013/0208114 | A1 | 8/2013 | Balsam |
| 2014/0011190 | A1 | 1/2014 | Parviainen et al. |
| 2014/0234949 | A1 | 8/2014 | Wasson et al. |
| 2015/0064727 | A1 | 3/2015 | Vaidyanathan et al. |
| 2015/0301031 | A1 | 10/2015 | Zin et al. |
| 2017/0137501 | A1 | 5/2017 | Hall et al. |
| 2020/0363405 | A1 | 11/2020 | Hall et al. |

FOREIGN PATENT DOCUMENTS

| | | | |
|---|---|---|---|
| WO | WO 2013/096817 | A2 | 6/2013 |
| WO | WO 2013/130613 | A1 | 9/2013 |
| WO | WO 2015/161291 | A1 | 10/2015 |
| WO | WO 2017/037126 | A1 | 3/2017 |
| WO | WO 2017/070594 | A1 | 4/2017 |
| WO | WO 2017/070603 | A1 | 4/2017 |

OTHER PUBLICATIONS

Lowe, C.F. and Romney M.G., "Bedbugs as Vectors for Drug-Resistant Bacteria" *Emerg. infect. Dis. 17*: 1132-1134, National Center for Infectious Diseases, United States (2011).

Mankin, R.W., et al., "Acoustic Indicators for Targeted Detection of Stored Product and Urban Insect Pests by Inexpensive Infrared, Acoustic, and Vibrational Detection of Movement," *J Econ. Entomol. 103*: 1636-1646, Entomological Society of America, United States (2010).

Prudencio, C.R., et al., "Recombinant peptides as new immunogens for the control of the bovine tick, *Rhipicephalus (Boophilus) microplus,*" *Vet Parasitol 172*(1-2):122-131, Elsevier B.V., Netherlands (2010).

Szalanski, A.L., et al., "Multiplex Polymerase Chain Reaction Diagnostics of Bed Bug (*Hemiptera: Cimicidae*)," *J. Med. Entomol. 48*: 937-940, Entomological Society of America, United States (2011).

Vaidyanathan, R., et al., "Review Article: Bed Bug Detection: Current Technologies and Future Directions," *Am. J. Trop. Med. Hyg.* 88(4), 2013, pp. 619-625, United States (2013).

Wong, M., et al., Strategies for Housing Authorities and Other Lower-Income Housing Providers to Control Bed Bugs, *Journal of Housing & Community Development* vol. 70 Issue 3, pp. 20-28, United States (2013).

International Search Report for International Patent Application No. PCT/US2013/028028, Korean Intellectual Property Office, Republic of Korea, dated Jun. 3, 2013, 3 pages.

Written Opinion of the International Searching Authority for International Patent Application No. PCT/US2013/028028, Korean Intellectual Property Office, Republic of Korea, dated Jun. 3, 2013, 5 pages.

Non-final Office Action dated Dec. 19, 2014, in U.S. Appl. No. 14/382,113, 371(c) date: Aug. 29, 2014.

Final Office Action dated Apr. 6, 2015, in U.S. Appl. No. 14/382,113, 371(c) date: Aug. 29, 2014.

Non-final Office Action dated Feb. 5, 2016, in U.S. Appl. No. 14/942,478, filed Nov. 16, 2015.

International Search Report for International Patent Application No. PCT/US2016/058290, U.S. Commissioner of Patents, United States, dated Jan. 24, 2017, 3 pages.

Written Opinion of the International Searching Authority for International Patent Application No. PCT/US2016/058290, U.S. Commissioner of Patents, United States, dated Jan. 24, 2017, 9 pages.

Janeway, C.A., et al., "The Structure of a typical antibody molecule," Immunobiology: The Immune System in Health and Disease. 5th edition. New York: Garland Science, United States (2001), Retrieved from https://www.ncbi.nlm.nih.gov/books/NBK27144/ on Dec. 13, 2016.

Rosler, E.S., et al., "An in vivo competitive repopulation assay for various sources of human hematopoietic stem cells," *Blood 96*(10): 3414-3421, The American Society of Hematology, United States (2000).

International Search Report for International Patent Application No. PCT/US2016/058300, U.S. Commissioner of Patents, United States, dated Feb. 28, 2017, 4 pages.

Written Opinion of the International Searching Authority for International Patent Application No. PCT/US2016/058300, U.S. Commissioner of Patents, United States, dated Feb. 28, 2017, 8 pages.

Extended European Search Report for European Patent Application No. 16858386.2, European Property Office, Munich, Germany, dated May 13, 2019, 7 pages.

Extended European Search Report for European Patent Application No. 16858381.3, European Patent Office, The Hague, Netherlands, dated Jun. 11, 2019, 13 pages.

Non-final Office Action dated Jun. 27, 2019, in U.S. Appl. No. 15/331,632, filed Oct. 21, 2016, 16 pages.

Rudikoff, S., et al., "Single amino acid substitution altering antigen-binding specificity," Proceedings of the National Academy of Sciences of the United States of America 79(6):1979-1983, National Academy of Sciences, United States (1982).

De Pascalis, R., et al., "Grafting of "abbreviated" complementarity-determining regions containing specificity-determining residues essential for ligand contact to engineer a less immunogenic humanized monoclonal antibody," Journal of Immunology 169(6):3076-3084, The American Association of Immunologists, Inc., United States (2002).

Casset, F., et al., "A peptide mimetic of an anti-CD4 monoclonal antibody by rational design," Biochemical and Biophysical Research Communications 307(1):198-205, Elsevier Science, United States (2003).

Van Regenmortel, M.H.V., "Molecular dissection of protein antigens and the prediction of epitopes," Chapter 1, in "Laboratory Techniques in Biochemistry and Molecular Biology," 19:1-39, Elsevier Science, United States (1988).

Lloyd, C., et al., "Modelling the Human Immune Response: Performance of a $10^{11}$ Human Antibody Repertoire Against a Broad Panel of Therapeutically Relevant Antigens," Protein Engineering, Design and Selection, 22(3):159-168, Oxford University Press, England (2009).

Brown, M., et al., "Tolerance to Single, but not Multiple, Amino Acid Replacements in Antibody $V_H$ CDR2: A Means of Minimizing B Cell Wastage from Somatic Hypermutation?," Journal of Immunology 156(9):3285-3291, American Association of Immunologists, United States (1996).

Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).

Harlow, E. and Lane, D., eds., "Antibodies: A Laboratory Manual," 3:23-24, 3:26, 4:37-47, 5:55-59, and 5:72-76, Cold Spring Harbor Laboratory, United States (1988).

Non-final Office Action dated Jul. 3, 2019, in U.S. Appl. No. 15/331,081, filed Oct. 21, 2016, 28 pages.

Extended European Search Report for European Patent Application No. 22153308.6, European Property Office, Munich, Germany, dated Aug. 30, 2022, 13 pages.

BED BUGS DETECTION DEVICE

CROSS-REFERENCE TO RELATED APPLICATION

This application is a continuation of U.S. application Ser. No. 15/331,081, filed Oct. 21, 2016, which claims the benefit of the filing date of U.S. Appl. No. 62/244,188, filed Oct. 21, 2015, each of which are hereby incorporated by reference in their entireties.

FIELD

The embodiments generally relate to detecting a presence of pests, and more particularly, to using an electronic detection device to detect household pest insects including, for example, bed bugs.

BACKGROUND

Studies and surveys in the past decade suggest that bed bug infestations have become increasingly prevalent both in the United States and worldwide. To begin treating bed bug infestations, pest control operators need effective and accurate methods for detecting and identifying the presence of bed bugs.

In a typical example, a pest control operator is called to inspect a housing unit (e.g., home, apartment, hotel, or hospital) where bed bugs may be present. Current detection options include visually inspecting a suspected room, which is ineffective and unreliable, or obtaining a sample of suspected bed bug residue to be tested at an off-site testing lab. Often, the pest control operator may need to use expensive, off-site DNA testing equipment to analyze the suspected residue for evidence of bed bugs. Additionally, bed bugs testing equipment (e.g., DNA testing equipment) often cannot be used on-site and may require 24 to 48 hours to produce a testing result.

SUMMARY

In accordance with certain disclosed embodiments of the present disclosure, there is provided a system and a method for determining, by a detection device, whether a presence of one or more insect pests is detected. The detection device can be configured to store pest profiles, each with thresholds for one or more profile characteristics. In an embodiment, the detection device detects, within a certain amount of time, a presence of a sample fluid (or test fluid) being tested during a lateral flow assay test processed within the detection device. The detection device further checks that a sufficient amount of colored particles has passed a testing zone, such that a presence of one or more pests within the sample fluid can be detected. Then, the disclosed device compares testing results to one or more pest profiles to determine whether one or more pests are present.

In an embodiment, a detection device receives a test fluid near a first end of a test strip within the detection device, wherein the test fluid flows past a reagent portion of the test strip containing colored particles and through a reaction portion of the test strip, wherein the reagent portion contains antibodies conjugated to colored particles, and wherein the conjugated antibodies are capable of binding with any bed bug antigen within the test fluid to form bed bug molecules. A first optical sensor within the detection device monitors a reaction color intensity of the reaction portion of the test strip as immobilized antibodies within the reaction portion bind with the bed bug molecules. A second optical sensor within the detection device monitors a background color intensity of a portion of the test strip near the reaction portion. The detection device determines that an initial amount of test fluid has flowed past the reaction portion based on the monitored reaction color intensity and the monitored background color intensity. The detection device determines that a given amount of colored particles from the reagent portion has flowed past the reaction portion based on the monitored reaction color intensity and the monitored background color intensity. The detection device detects that a time delay has elapsed since determining that the given amount of colored particles has flowed past the reaction portion. The detection device determines a bed bug profile result using the monitored color intensities and minimum and maximum color intensity thresholds, wherein the time delay, the minimum color intensity threshold, and the maximum color intensity threshold are stored in a memory of the detection device, and wherein the profile result indicates whether a presence of bed bugs was detected in the test fluid. Then, the detection device outputs the bed bug profile result using a visual display.

In certain embodiments, the antibody is produced by the hybridoma deposited at the American Type Culture Collection (ATCC) under Accession Number PTA-122644 [BB2], or an antigen-binding fragment thereof.

In certain embodiments, the antibody is produced by the hybridoma deposited at the ATCC under Accession Number PTA-122645 [BB7], or an antigen-binding fragment thereof.

In certain embodiments, the antibody is a monoclonal antibody or an antigen-binding fragment thereof comprising the heavy chain and light chain complementarity determining regions (CDRs) of an antibody produced by the hybridoma deposited at the ATCC under Accession Number PTA-122644 [BB2] or an antibody produced by the hybridoma deposited at the ATCC under Accession Number PTA-122645 [BB7]. In certain embodiments, the antibody or antigen-binding fragment thereof comprises the heavy and light chain variable regions of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the antibody or antigen-binding fragment thereof comprises the heavy and light chains of the antibody produced by the hybridoma deposited at the ATCC under Accession Number PTA-122644 [BB2] or the antibody produced by the hybridoma deposited at the ATCC under Accession Number PTA-122645 [BB7].

In certain embodiments, the antibody or antigen-binding fragment of any of the above embodiments is capable of binding to a bed bug antigen in a lysate of whole bed bugs or an extract of collection paper comprising bed bug waste material.

In certain embodiments, the antibody is a mutant of an antibody produced by the hybridoma deposited at the ATCC under Accession Number PTA-122644 [BB2] or a mutant of an antibody produced by the hybridoma deposited at the ATCC under Accession Number PTA-122645 [BB7], wherein the mutant is capable of binding to a bed bug antigen in a lysate of whole bed bugs or an extract of collection paper comprising bed bug waste material.

In certain embodiments, the antibody is a conjugated monoclonal antibody or a conjugated antigen binding fragment comprising any of the antibodies, antigen-binding fragments, or mutants of the above inventions or embodiments and a detection agent. In certain embodiments, the detection agent is colloidal gold. In certain embodiments, the conjugated antibody or conjugated antigen-binding fragment comprises an antibody produced by the hybridoma deposited at the ATCC under Accession Number PTA-122644 [BB2], or an antigen-binding fragment thereof, or an antibody produced by the hybridoma deposited at the ATCC under Accession Number PTA-122645 [BB7], or an antigen-binding fragment thereof.

Certain embodiments can include a composition comprising any of the above antibodies, antigen-binding fragments, mutants, or conjugated antibodies or conjugated antigen-binding fragments, or a combination thereof. In certain embodiments, the composition comprises an antibody produced by the hybridoma deposited at the ATCC under Accession Number PTA-122644 [BB2] and an antibody produced by the hybridoma deposited at the ATCC under Accession Number PTA-122645 [BB7]. In certain embodiments, the composition comprises an antibody produced by the hybridoma deposited at the ATCC under Accession Number PTA-122644 [BB2], and a conjugated antibody comprising the antibody produced by the hybridoma deposited at the ATCC under Accession Number PTA-122645 [BB7] and a detection agent. In certain embodiments, the composition comprises an antibody produced by the hybridoma deposited at the ATCC under Accession Number PTA-122645 [BB7], and a conjugated antibody comprising the antibody produced by the hybridoma deposited at the ATCC under Accession Number PTA-122644 [BB2] and a detection agent.

Certain embodiments can include a kit comprising any of the above inventions or embodiments, or a combination thereof.

Certain embodiments can include a hybridoma capable of producing an antibody, wherein the hybridoma is deposited at the ATCC under Accession Number PTA-122644 [BB2] or wherein the hybridoma is deposited at the ATCC under Accession Number PTA-122645 [BB7].

Certain embodiments can include an isolated cell producing an antibody, antigen-binding fragment, or mutant of any of the above inventions or embodiments.

Certain embodiments can include a method of making an antibody, antigen-binding fragment, or mutant of any of the above inventions or embodiments, comprising culturing an isolated cell producing the antibody, antigen-binding fragment, or mutant, and isolating the antibody, antigen-binding fragment, or mutant from the cultured cell.

Certain embodiments can include a method of detecting bed bugs, comprising contacting a sample comprising a bed bug antigen with any of the antibodies, antigen-binding fragments, mutants, conjugated antibodies or conjugated antigen-binding fragments, or compositions of the above inventions or embodiments, or a combination thereof, and detecting binding of the bed bug antigen to the antibody or antigen-binding fragment, mutant, conjugated antibody or conjugated antigen-binding fragment, composition, or combination thereof. In certain embodiments, the sample is contacted with an antibody of any of the above inventions or embodiments and a conjugated antibody of any of the above inventions or embodiments. In certain embodiments, the antibody is produced by the hybridoma deposited at the ATCC under Accession Number PTA-122644 [BB2], and the conjugated antibody comprises the antibody produced by the hybridoma deposited at the ATCC under Accession Number PTA-122645 [BB7] and a detection agent. In certain embodiments, the antibody is produced by the hybridoma deposited at the ATCC under Accession Number PTA-122645 [BB7], and the conjugated antibody comprises the antibody produced by the hybridoma deposited at the ATCC under Accession Number PTA-122644 [BB2] and a detection agent. In certain embodiments, the detecting comprises performing a lateral flow assay. In certain embodiments, the method further comprises collecting a sample comprising the bed bug antigen with a collection device and extracting antigens from the sample. In certain embodiments, the collection device is a swab.

BRIEF DESCRIPTION OF THE FIGURES

The accompanying drawings, which are included to provide a further understanding of the invention and are incorporated in and constitute a part of this specification, illustrate embodiments of the invention and together with the description serve to explain the principles of the invention.

FIGS. 20-21 show noticeable dirt and residue for less dilute samples at the bottom of the test strips associated with the higher levels of bed bug infestation.

In FIG. 22A, the x-axis "concentration" is the dilution associated with the measured swab samples, and the y-axis is the value for the "test line area" provided by the Axxin test strip reader. In FIG. 22B, the value obtained for buffer 1 as a negative control (i.e., "Bo") was divided by itself to yield a normalized value of 1. The negative control reading (Bo) was then divided by the test line area (B) for each test sample dilution in the level, where smaller values under 1 suggest larger amounts of bed bug antigen and values above 1 indicate absence of bed bug antigen.

FIG. 25 shows noticeable dirt and residue for less dilute samples at the bottom of the test strips associated with the higher levels of bed bug infestation. Labeling of the strips and interpretation of results is as described for FIGS. 16-21.

FIGS. 30-31 show noticeable dirt and residue for less dilute samples at the bottom of the test strips associated with the higher levels of bed bug infestation. Labeling of the strips and interpretation of results is as described for FIGS. 16-21.

The drawing in which an element first appears is typically indicated by the leftmost digit or digits in the corresponding reference number. In the drawings, like reference numbers may indicate identical or functionally similar elements.

DETAILED DESCRIPTION

What is needed is a portable and reliable detection device that can be used on-site to identify and detect the presence of bed bugs within minutes. In accordance with certain disclosed embodiments of the present disclosure, there is provided a system and a method for determining, by a detection device, whether a presence of one or more insect pests is detected. The detection device can be configured to store pest profiles, each with thresholds for one or more pest profile characteristics. In an embodiment, the detection device detects, within a certain amount of time, a presence of a sample fluid being tested during a lateral flow assay test processed within the detection device. The detection device further checks that a sufficient amount of colored particles has passed a testing zone, such that a presence of one or more pests within the sample fluid can be detected. Then, the disclosed device compares testing results to one or more pest profiles to determine whether one or more pests are present.

System Implementation

Figure 1:
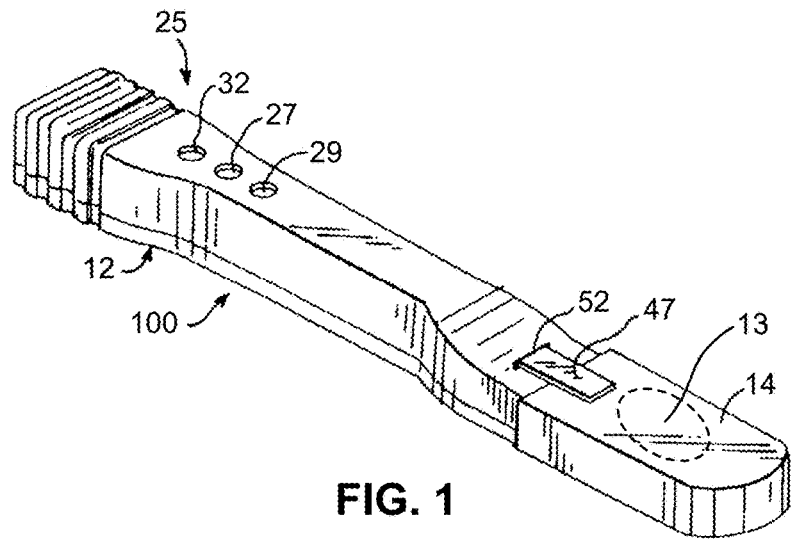
FIG. 1 is a diagram of a detection device for detecting a presence of bed bugs, according to an example embodiment.

FIG. 1 is a diagram illustrating a detection device 100 for detecting a presence of bed bugs, according to an example embodiment. Detection device 100 may be implemented similarly to an assay test device described in U.S. Pat. No. 7,220,597, titled "Assay Test Device and Method of Making Same," and U.S. Pat. No. 7,214,542, "Method of Processing Assay Test Results," both of which are incorporated by reference herein in their entireties. As shown, detection device 100 can include an elongated housing 12 adapted to be held in the hand of a user, such as a pest control operator. In an embodiment, housing 12 may include removable cap 14 further attached to switch actuator 47 extending through opening 52. As further detailed in FIG. 5 below, when removable cap 14 is removed, detection device 100 can be activated (e.g., turned on) to start executing a detection software program to identify and detect a presence of bed bugs. In an embodiment, instead of removable cap 14, detection device 100 may include opening 13 such that detection device 100 can be activated when light entering opening 13 is detected. In an embodiment, detection device 100 can include a switch or button for activating detection device 100.

Figure 2:
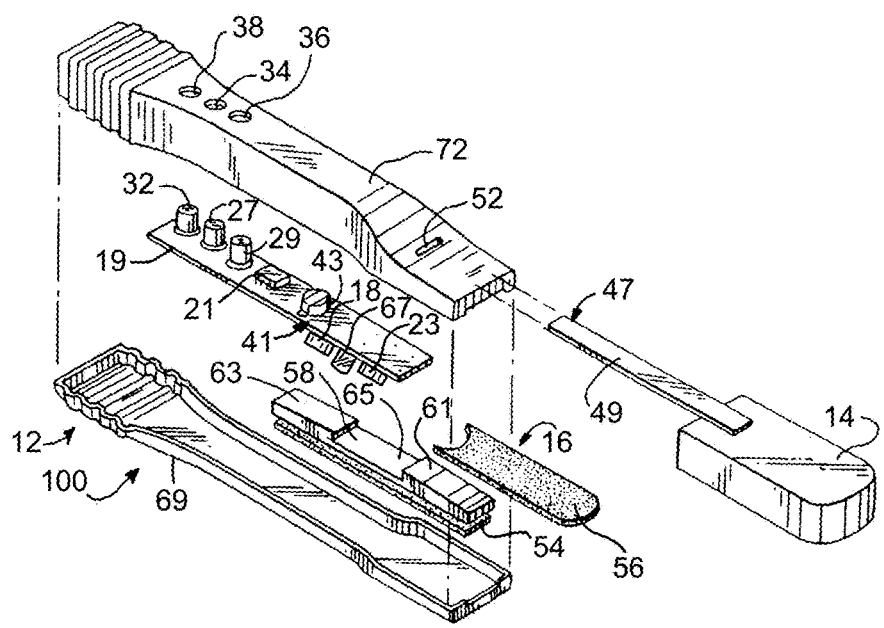
FIG. 2 is an exploded view of the detection device of FIG. 1, according to an example embodiment.

Result display 25 can include yellow light emitting diode (LED) 27, green LED 29 and red LED 32 disposed in a row on the top surface of housing 12 and positioned within corresponding holes 34, 36 and 38 of FIG. 2. A specific one or more of LEDS 27, 29, and 32 can be controlled by processor 21 of FIG. 2 to indicate, for example, by turning on, whether a detection result indicates bed bugs are present, or whether the detection result is indeterminate. In an embodiment, an LED display, an LCD display, or other display electronics can be used instead to display the detection result.

Figure 3:
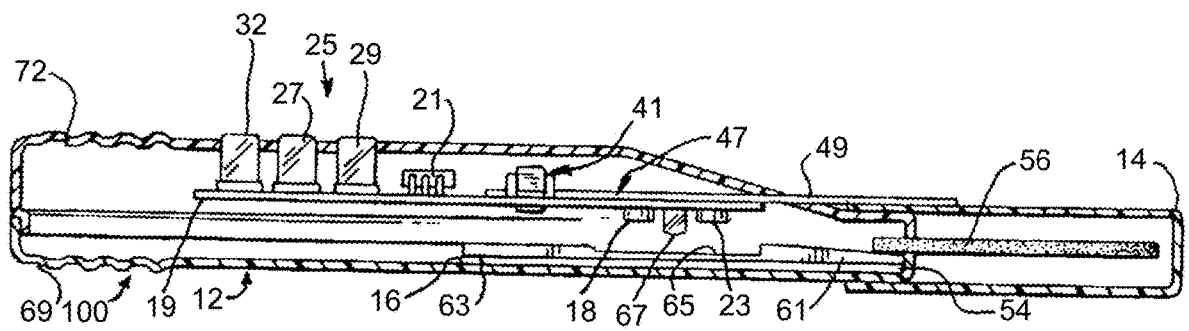
FIG. 3 is an enlarged sectional elevational view of the detection device of FIG. 1, according to an example embodiment.

FIG. 2 is a diagram illustrating an example exploded view of detection device 100 from FIG. 1, according to an example embodiment. FIG. 3 further illustrates an enlarged elevational view of detection device 100 from FIG. 1. Housing 12 can include bottom portion 69 that is secured to top portion 72 for enclosing printed circuit board 19 and elongated test strip 16 disposed longitudinally within housing 12. Also shown is removable cap 14 connected to switch actuator 47 including insulator strip 49, which can be in the form of a rigid strip of suitable materials such as thermal plastic or other such material. Detection device 100 can be activated when insulator strip 49 is removed from and through opening 52.

Test strip 16 can be in the form of the test strip disclosed in European patent application No. EP0,962,771A1, incorporated by reference herein in its entirety. In an embodiment, test strip 16 provides an environment for performing a lateral flow assay or immunoassay test used by detection device 100 to determine whether bed bugs are present or detected. Depending on a type of test strip 16 and materials/components incorporated on or within test strip 16, device detector 100 may also detect a presence of other types of insect pests (e.g., cockroaches or termites) or whether multiple pests, including bed bugs, are present.

To perform a lateral flow assay, test strip 16 includes a backing strip 54 that has a sample pad or wick 56 for receiving and absorbing a sample fluid potentially containing bed bug antigens. For example, the sample fluid may be an extract produced from a sample potentially comprising bed bug residues such as wastes and/or tissues. In an embodiment, to obtain the sample fluid, a pest control operator may first use a swabbing material (e.g., a cotton swab) to swab bed bug hot spots at a given location. Example bed bug hot spots can include bed sheets, mattress frames, mattress legs, outlets, window sills, furniture surfaces, or other regions proximate to a sleeping area (e.g., mattress, futon, or couch). Upon swabbing bed bug hotspots, the pest control operator can then dip the swabbing material, potentially containing bed bug residue, into an extract buffer (i.e., a liquid that can extract bed bug antigens from a sample) within a vial or other containers to produce a sample fluid. Then, the pest control operator can drip portions of the buffer liquid onto a sample pad or wick 56, which receives the buffer liquid-swab mixture as sample fluid.

In an embodiment where detection device 100 includes removable cap 14, test strip 16 can extend out of housing 12 and be covered by removable cap 14 or a lid portion when it is assembled to housing 12. When removable cap 14 is removed from housing 12, wick 56 is exposed so that the sample fluid can be applied as described. In an embodiment without removable cap 14, wick 56 can instead receive sample fluid applied through opening 13 as depicted in FIG. 1.

Test strip 16 includes porous carrier strip 58 that has reagent section or pad 61 affixed to wick 56, and a fluid absorption section or absorption pad 63 at the opposite end portion of test strip 16 from wick 56. Porous carrier strip 58 enables the sample fluid from wick 56 to flow through reagent pad 61 and line forming zone 65 to absorption pad 63 where excess sample fluid is absorbed.

A catching section or line forming zone 65 on the upper surface of an intermediate portion of porous carrier strip 58 is disposed opposite a reaction sensor or front sensor 23. At line forming zone 65, a line of specific color intensity and coloration is formed once a reaction involving bed bug antigens occurs if a sufficient amount of bed bug antigen is present in the sample fluid indicating that bed bugs are present within a room suspected of hosting bed bugs. In an embodiment, detection device 100 can read a measurement of front sensor 23 to determine whether bed bug presence is detected. In an embodiment, to increase accuracy and to reduce (or eliminate) calibration timing, detection device 100 can use measurements from more than one sensor, such as front sensor 23 and rear sensor 18.

In an embodiment, reagent pad 61 can contain a solubilizable mixture of anti-bed bug antibodies conjugated to colored particles. Example colored particles can include, for example, colloidal gold, latex microspheres, or fluorescent labels. A colored particle is used as a detection agent such that the more colored particles detected by detection device 100 during profile evaluation (to be further described with respect to FIG. 7), the higher the likelihood that a presence of a pest, such as bed bugs, are present in the sample. As sample fluid received on wick 56 migrates through reagent pad 61 to an intermediate portion of carrier strip 58, the sample fluid can mix with the solubilizable mixture at reagent pad 61 to form a sample-conjugate mixture. Bed bug antigens present in the sample fluid can bind to the conjugated anti-bed bug antibodies to form sample-conjugate molecules. When the sample fluid dissipates or solubilizes the solubilizable mixture, the sample-conjugate fluid flows towards absorption pad 63 until a background sensor or rear sensor 18 disposed opposite the intermediate portion of the carrier strip 58 detects the presence of the sample-conjugate fluid due to the change in color of the wetted porous carrier strip 58. In an embodiment, to increase accuracy and reduce (or eliminate) calibration, detection device 100 determines a relationship between measurements by more than one sensor, including front sensor 23 and rear sensor 18, to determine whether the sample-conjugate fluid is present.

To enable sensor measurements to be taken, an illuminating light-emitting diode (LED) 67 can be disposed or mounted on the underside of printed circuit board 19 between rear sensor 18 and front sensor 23 to illuminate the intermediate portion of porous carrier strip 58 to reflect light therefrom to the sensors. Illuminating LED 67 can produce light in the visible range of the electromagnetic spectrum. A white LED may provide more accurate measurements, but another colored LED, such as a green LED, can also be used as illuminating LED 67, depending on the color of the line formed in line forming zone 65. In an embodiment, detection device 100 can trigger illuminating LED 67 to light whenever a measurement from rear sensor 18 or front sensor 23 is to be read.

Line forming zone 65 can include a region (e.g. a line) of one or more types of immobilized antibodies that can bind with bed bug antigens of sample-conjugate molecules within the sample-conjugate fluid flowing past line forming zone 65. In an embodiment, the immobilized antibodies can include the anti-bed bug antibody portion of the conjugated anti-bed bug antibodies on or within reagent pad 61. As the sample-conjugate fluid from reagent pad 61 flows through line forming zone 65 towards absorption pad 63, a greater amount of sample-conjugated molecules can further react with (or bind to) the immobilized antibodies. In an embodiment where the conjugated particle is a colored particle like colloidal gold, as more reaction occurs within line forming zone 65 due to a greater presence of bed-bug antigens within sample fluid, the coloration within line forming zone 65 can intensify at a greater rate. In an embodiment, depending on the type of conjugated particle, a luminescence or fluorescence level may intensify instead.

Rear sensor 18 (background sensor) and front sensor 23 (reaction sensor) can be mounted on the underside of printed circuit board 19. Front sensor 23 can be disposed directly opposite line forming zone 65 of test strip 16 to capture a colorimetric reflectance of the reaction, i.e., a color intensity of line forming zone 65. Rear sensor 18 can be disposed near line forming zone 16 (but not directly over line forming zone 16) between line forming zone 16 and absorption pad 63. In an embodiment, rear sensor 18 can instead be disposed between line forming zone 16 and reagent pad 61. Rear sensor 18 similarly measures or captures a color intensity of the test strip region disposed opposite rear sensor 18. Though detection device 100 may use only readings from rear sensor 18 to detect a presence of the sample-conjugate fluid as it flows along test strip 16, in an improved embodiment, detection device may use measurement readings from both rear sensor 18 and front sensor 23. Similarly, detection device 100 may use readings from front sensor 23 or both rear sensor 18 and front sensor 23 to determine whether a presence of bed bugs are detected from line forming zone 65.

Each of rear sensor 18 and front sensor 23 can be a photo-optic sensor including, for example, a photo conductive cell or light dependent resistor that varies resistance depending on a detected and measured incident light intensity due to colorimetric diffuse reflectance within line forming zone 65. A measured colorimetric diffuse reflectance can be representative of the color intensity within line forming zone 65. For example, as the color within line forming zone 65 intensifies, more light can be absorbed by line forming zone 65, i.e. less light can be reflected by line forming zone 65, and a photoconductive cell can output an increased resistance due to a lower incident light intensity. In an embodiment, the photo-optic sensor may include a photodiode that produces a leakage current that is directly proportional to the incident light intensity. Depending on the conjugated particle, other types of sensors, such as a Hall effect sensor for capturing magnetic flux density, may be used.

Power supply generally indicated at power region 41 is mounted on the top surface of printed circuit board 19. Power region 41 can include battery 43 electrically powering printed circuit board 19 and its components including, for example, yellow LED 27, green LED 29, red LED 32, rear sensor 18, illuminating LED 65, front sensor 23, and processor 21.

Processor 21 can be mounted on the top surface of printed circuit board 19 and programmed to start detecting a presence of bed bugs when detection device 100 is activated or turned on. Processor 21 can include input ports for receiving power and reading measurements from front sensor 23 and rear sensor 18 and include output ports for controlling illuminating LED 65 and LEDS 32, 27, and 29 of result display 25. In an embodiment, processor 21 may be a microprocessor (e.g., an 8-bit or 16-bit microcontroller) having limited processing and memory capabilities due to size, power, and cost constraints of detection device 100. To efficiently detect a presence of bed bugs given limited hardware, processor 21 can include stored algorithms for efficient calibration processing and accurate bed bug detection results. In an embodiment, processor 21 can detect different types of insect pests or a presence of more than one type of insect pest, including bed bugs.

Figure 4:
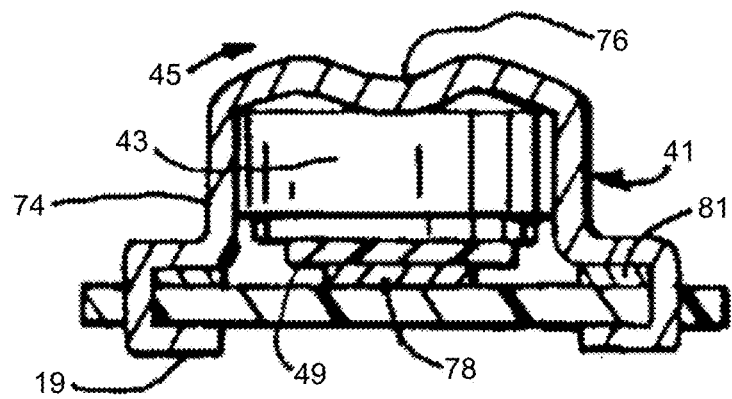
FIG. 4 is an enlarged sectional view of the detection device of FIG. 3 before a cap portion is removed, according to an example embodiment.
Figure 5:
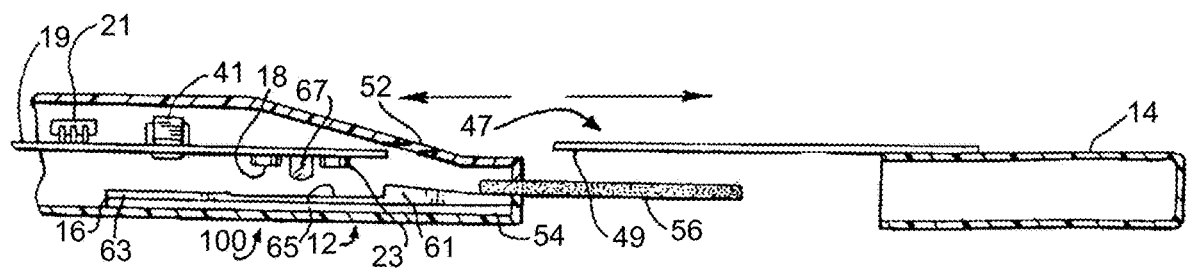
FIG. 5 is a fragmentary sectional elevational view of the device of FIG. 3 when the cap portion is being removed, according to an example embodiment.
Figure 6:
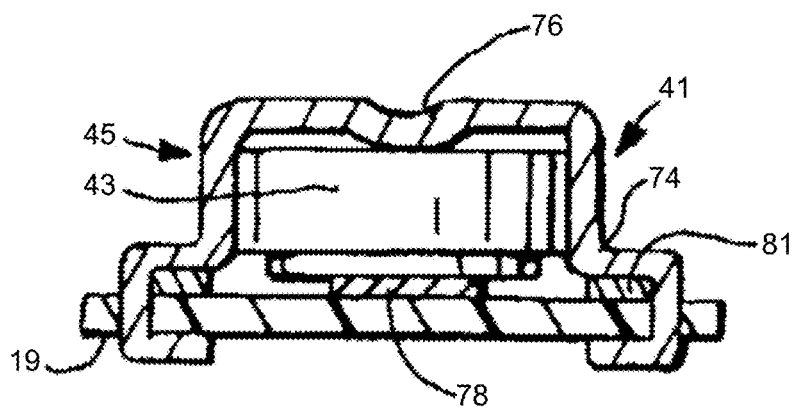
FIG. 6 is an enlarged sectional view of FIG. 5 after a cap portion is removed, according to an example embodiment.

FIGS. 4-6 are diagrams illustrating configurations within detection device 100, according to an example embodiment. As depicted, FIG. 4 is an enlarged sectional view of the detection device of FIG. 3 before removable cap 14 is removed and detection device 100 is powered, according to an example embodiment. FIG. 5 illustrates a fragmentary sectional elevational view of the device of FIG. 3 when removable cap 14 is being removed, according to an example embodiment. FIG. 6 illustrates an enlarged sectional view of FIG. 5 after removable cap 14 has been removed, according to an example embodiment.

In an embodiment, switch actuator 47 in the form of insulator strip 49 extends through an opening 52 in an angular wall portion of the housing 12 to switch 45 when removable cap 14 is assembled to housing 12 as shown in FIGS. 1 and 3. When removable cap 14 is removed from housing 12 as indicated in FIG. 5, switch actuator 47 can be pulled away from switch 45 as indicated in FIGS. 4 and 6 to cause battery 43 to be connected electrically to printed circuit board 19 for energizing or powering on detection device 100.

Though detection device 100, as shown, can be a single-use device that is accurate and speedy in its bed bugs presence determination, in an embodiment, detection device 100 can be employed as a multiple-use device. For example, a multiple-use detection device 100 can include housing 12 that can be disassembled as indicated in FIG. 2 to permit test strip 16 to be replaced by a fresh test strip for performing additional lateral flow test assays. Insulator strip 49 of switch actuator 47 can be in the form of a rigid strip of suitable materials such as thermal plastic or other such material. In this regard, insulator strip 49 can be reinserted through opening 52 and under battery 43 to disengage battery 43 electrically from printed circuit board 19.

Figure 7:
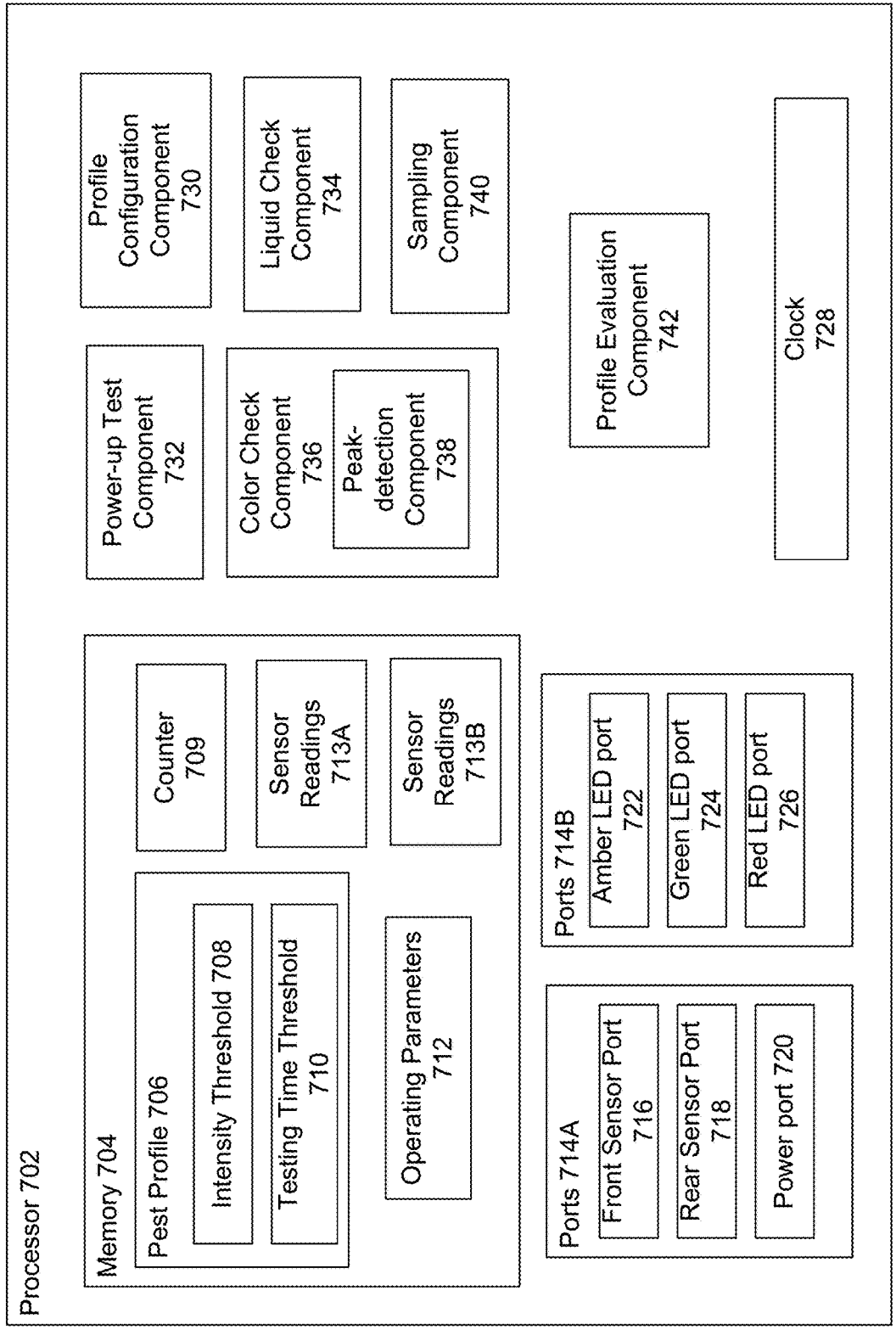
FIG. 7 is a block diagram illustrating components within a processor of a detection device according to an example embodiment.

FIG. 7 is a block diagram 700 illustrating components within processor 700 of a detection device, such as detection device 100 from FIGS. 1-3, according to an example embodiment. In an embodiment, processor 700 can be an example implementation of processor 21 from FIGS. 2, 3, and 5. Processor 702 can include memory 704, ports 714A and B, clock 728, and components 730-742.

Ports 714A can be input ports including power port 720, which powers processor 702 from a power source, such as battery 43 of printed circuit board 19 from FIG. 2. Input ports 714A can further include front sensor port 716 and rear sensor port 718, which receive sensor measurements from front sensor 23 and rear sensor 18 of FIG. 2, respectively. Ports 714B can include output ports for outputting a result indicating whether processor 702 encountered an error and whether processor 702 determined a presence of one or more pests including, for example, bed bugs. As shown, output ports 714B may include yellow LED port 722, green LED port 724, and red LED port 726 to control yellow LED 27, green LED 29, and red LED 32 of FIG. 2, respectively. In an embodiment, a single LED port may control more than one LED.

Memory 704 can include registers, RAM, ROM, cache, or other types of memory storage. Memory 704 stores pest profile 706, operating parameters 712, counter 709, and sensor readings 713A and B. Operating parameters 712 can include a liquid threshold, a color threshold, and minimum and maximum thresholds for each of front sensor 23 and rear sensor 18. The liquid threshold can be representative of a minimum initial amount or concentration of sample-conjugate fluid flowing past line forming zone 65 that may be needed before processor 702 continues to determine whether bed bugs are detected. The color threshold can be representative of a color intensity value proportional to a minimum amount or concentration of sample-conjugate fluid flowing past line forming zone 65 that may be needed to validate any final detection determination made by processor 702. Other operating parameters 712 can include a range of power values (e.g., minimum and maximum power voltages) such that any power values outside the range indicates that processor 702 is not being properly powered via power port 720, and a range of sensor values (e.g., minimum and maximum sensor values) such that sensor values outside the sensor range are invalid. Depending on a type of sensor used or measurement methodology, sensor range values may be, for example, resistances, currents, or voltages. For example, a sensor may be a photodiode (i.e., a device that converts received light to current) or a photoconductive cell (i.e., a device that converts received light to resistance). The measured sensor value for each type of sensor may be, for example, a voltage value.

Counter 709 can be a register that is incremented by clock 728 of processor 702. A counter value of counter 709 can be representative of a period of time or clock cycles since counter 709 was activated or initialized. In an embodiment, the counter value may be representative of a period of time since counter 709 was cleared or reset to 0 by processor 702.

Pest profile 706 can include thresholds or parameters configured for profile characteristics of a specific insect pest, such as bed bugs, associated with pest profile 706. In an embodiment, profile characteristics can include a testing time period and a measured color intensity range. As shown, configured thresholds include intensity threshold 708 and testing time threshold 710, such that processor 702 determines a presence of a pest when processor 702 calculates a result value exceeding intensity threshold 708 after a counter value of counter 709 exceeds testing time threshold 710. In an embodiment, intensity threshold 708 can include a range of intensity thresholds, such as a minimum threshold and a maximum threshold, such that processor 702 indicates a detected presence of the pest only when a calculated result value exceeds or meets the maximum threshold. If the calculated value falls below the minimum threshold, processor 702 can indicate an absence of the pest. But, if the calculated value falls between the minimum and maximum thresholds, processor 702 may indicate or output an indeterminate result to reduce the number of false positives, i.e., incorrectly determining a presence of the pest. Similarly, testing time threshold 710 can include a range of testing time thresholds, such as a minimum testing time threshold and a maximum testing time threshold. In an embodiment, a testing result determined by processor 702 may only be accurate if using measurements between the minimum and maximum testing time thresholds.

In an embodiment, pest profile 706 can include two or more pest profiles for respective insect pests. Each pest profile can include, for at least one profile characteristic, a threshold range that does not overlap or intersect with a corresponding threshold range (i.e., threshold range of the same profile characteristics) of any other pest profile. For example, pest profile 706 can include a bed bug profile and a cockroach profile. The bed bug profile may be configured to include, for example, testing time thresholds 710 of 3 min and 5 min and intensity thresholds 708 ranging from 18 to 100. In contrast, the cockroach profile may include intensity thresholds 708 from 15 to 30 that overlap the bed bug profile's intensity thresholds between 18 and 30. But, the cockroach profile may also include testing time thresholds 710 from 9 min to 10 min that does not overlap any of the testing time thresholds 710 of all other pest profiles 706, including the bed bug profile (e.g., 9-10 min does not overlap 3-5 min in the bed bug profile).

Sensor readings 713A and 713B can store sensor readings from front sensor 23 and rear sensor 18, respectively. In an embodiment, sensor readings 713A and sensor readings 713B can each include respective initial sensor readings and respective subsequent sensor readings from front sensor 23 and rear sensor 18, respectively. In an embodiment, an initial sensor reading of each front sensor 23 and rear sensor 18 can be updated depending on when processor 702 executes color check component 740 (to be further described). By tracking subsequent sensor readings in association with a tracked time throughout the pest detection process, processor 702 can determine and detect whether two or more pest profiles 706 have been met, and indicate or output respective determination results. In an embodiment, one pest profile 706 is met or satisfied if each configured threshold within that same pest profile 706 is met.

Processor 702 can include various components 730-742 to implement the detection functionality of detection device 100. For ease of understanding, descriptions of the components of FIG. 7 will refer to FIGS. 1-3, which illustrate example structures or physical components of detection device 100. A component of processor 702 can include a selection of stored operations that, when executing in processor 702, causes processor 702 to perform the operations of the component.

Figure 8:
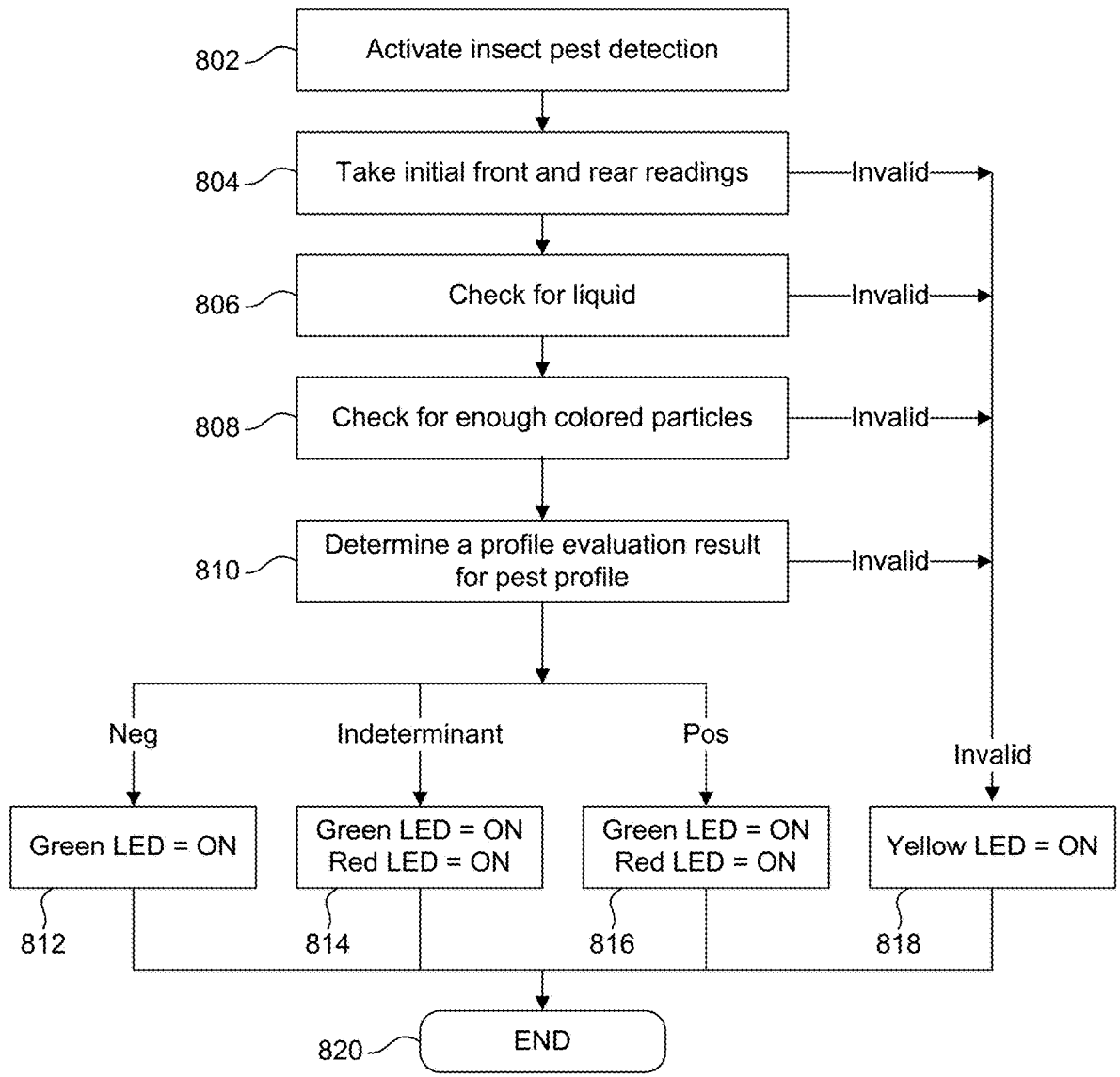
FIGS. 8-13 are flow charts illustrating methods performed by a detection device, according to an example embodiment.

FIG. 8 is a flow chart of a method 800 for a generalized algorithm for detecting whether one or more insect pests are present, according to an example embodiment. Method 800 can be performed by processing logic within one or more components, such as components 730-742 of processor 702 from FIG. 7, that may comprise hardware (e.g., circuitry, dedicated logic, programmable logic, microcode, etc.), software (e.g., instructions running on a processing device), or a combination thereof. For ease of reference, descriptions of the following steps may refer to components of FIG. 7 and structures within FIG. 2.

In step 802, power-up test component 732 activates detection device 100. Once activated, detection device 100 starts analyzing a lateral flow assay test for a presence of one or more insect pests, including bed bugs. Power-up test component 732 may activate detection device 100 when, for example, detection device 100 is turned on or powered. Power-up test component 732 may additionally launch a self-testing sequence to verify an operation status of detection device 100, further described with respect to FIG. 7 below. In an embodiment, power-up test component 732 lights up or blinks one or more LEDs to indicate that step 802 is being performed. For example, power-up test component 732 may blink green LED 29 and blink yellow LED 27.

In step 804, upon completing step 802, power-up test component 732 takes (or request sampling component 740 to take) an initial front sensor reading and an initial back sensor reading. These initial readings may be stored in sensor readings 713A and B.

In step 806, liquid check component 734 checks for an initial amount of detected liquid flowing past line forming zone 65. The liquid may be a sample-conjugate fluid flowing from reagent pad 61 towards absorption pad 63, described with regards to FIG. 2 above. Since peak detection and profile evaluation (as explained with respect to FIG. 7 below) may be time-critical, detection device 100 should only start tracking an elapsed time when a lateral flow assay test is detected to be occurring. For example, based on the specific conjugated anti-bed bugs antibody and concentration thereof in reagent pad 61, a bed bugs presence determination made by processor 700 may only be valid within a certain range of elapsed time since the lateral flow assay test has started.

In step 808, color check component 736 checks whether enough colored particles within a sample-conjugate fluid have passed line forming zone 65. In an embodiment where colloidal gold is used, this may be referred to as checking the "gold migration." In an embodiment, if too little of the sample-conjugate fluid has migrated past line forming zone 65, then any subsequent profile-evaluation results may be invalid. In an embodiment, this is because processor 702 determines a presence of bed bugs, i.e., a test result satisfies the bed bugs profile, based on at least a detected color intensity of line forming zone 65. Therefore, in an example, although bed bug residue may be present in the sample-conjugate fluid, a color intensity of line forming zone 65 may not reach a minimum intensity threshold if not enough, for example, colloidal gold has flowed past line forming zone 65. In an embodiment, color check component 736 may light up or blink one or more LEDs to indicate that step 808 is being performed. For example, color check component 736 may blink red LED 32 and blink yellow LED 27.

In step 810, profile evaluation component 742 determines a profile evaluation result for pest profile 706, such as a bed bug profile. In an embodiment, only one profile exists for evaluation. In another embodiment, more than one profile may be configured in pest profile 706, and profile evaluation component 742 determines a profile evaluation result for each insect pest having a configured pest profile. The profile evaluation result may be one of three possibilities: a presence of insect pest detected, an absence of insect pest detected, and an indeterminate result.

In an embodiment, if any of steps 804 to 810 returns an invalid result, method 800 proceeds to step 818. In step 818, processor 702 may control one or more LEDs to indicate that an error has occurred. For example, processor 702 may turn on yellow LED 27. In an embodiment, the turned on LED may continue to stay lit until battery 43 of detection device 100 dies.

In an embodiment, steps 812-816 include possible LED outputs that indicate a valid pest profile result from step 810. In an embodiment, profile evaluation component 742 may indicate a pest profile result using a variety of output transducers, including one or more LEDs, LCDs, speakers, or haptic feedback motors. In step 812, when the profile evaluation result from step 810 is negative or an absence of insect pest was detected, profile evaluation component 742 turns on green LED 29. In step 814, when the profile evaluation result from step 810 is indeterminate, profile evaluation component 742 turns on green LED 29 and red LED 32. And in step 816, when the profile evaluation result from step 810 is positive or a presence of insect pest was detected, profile evaluation component 742 turns on red LED 32. Method 800 ends in step 820.

FIGS. 9-13 are flow charts that detail various steps of method 800. Methods 900-1300 can be performed by processing logic within one or more components, such as components of processor 702 of FIG. 7, that may comprise hardware (e.g., circuitry, dedicated logic, programmable logic, microcode, etc.), software (e.g., instructions running on a processing device), or a combination thereof. For ease of reference, descriptions of the following steps may refer to components of FIG. 7 and structures within FIG. 2.

Figure 9:
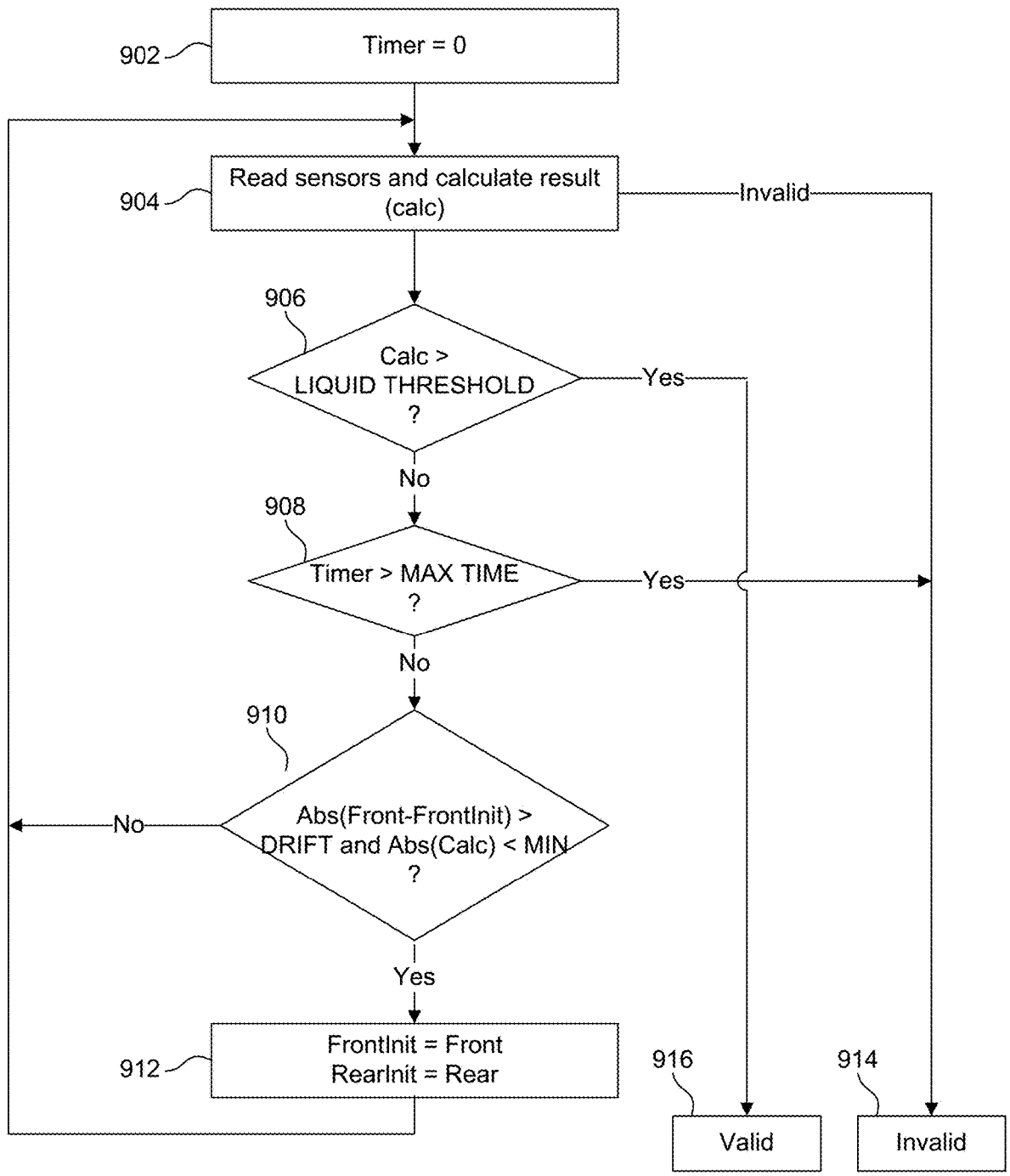

FIG. 9 is a flow chart of a method 900. Method 900 details operations of step 806, which checks for liquid, according to an example embodiment. In step 902, liquid check component 734 initializes, sets to 0, resets, or clears counter 709.

In step 904, liquid check component 734 invokes sampling component 740 to read measurements from rear sensor 18 and front sensor 23. Liquid check component 734 receives a calculated result (Calc) or an indication that an error occurred, i.e., the calculated result is invalid. If an error occurred, liquid check component 734 returns an invalid result in step 914.

In step 906, liquid check component 734 determines whether the received calculated result exceeds a liquid threshold within operating parameters 712. If the liquid threshold has been exceeded, liquid check component 734 returns a valid result in step 916. A calculated result exceeding the liquid threshold may indicate that a lateral test assay for, for example, bed bug detection is taking place.

In step 908, liquid check component 734 determines whether a maximum time (e.g., 24 hours) has elapsed. If so, liquid check component 734 returns an invalid result in step 914.

In step 910, liquid check component 734 determines whether initial front and back sensor readings need to be retaken. In an embodiment, liquid check component 734 determines whether the following inequality is satisfied: "|Front reading—initial front reading|>DRIFT and |Calc|<MIN." A current front sensor reading that drifts too far from the stored initial front reading, e.g., exceeds a DRIFT value of 20, should be recalibrated if the calculated result (Calc), is below MIN, such as 3. A calculated result below a specified minimum, e.g., 3, may indicate that the calculated result is caused by noise in sensor measurements.

In step 912, liquid check component 734 recalibrates front and rear sensors by setting the initial front and initial rear readings to a current front and a current rear reading, respectively.

Figure 10:
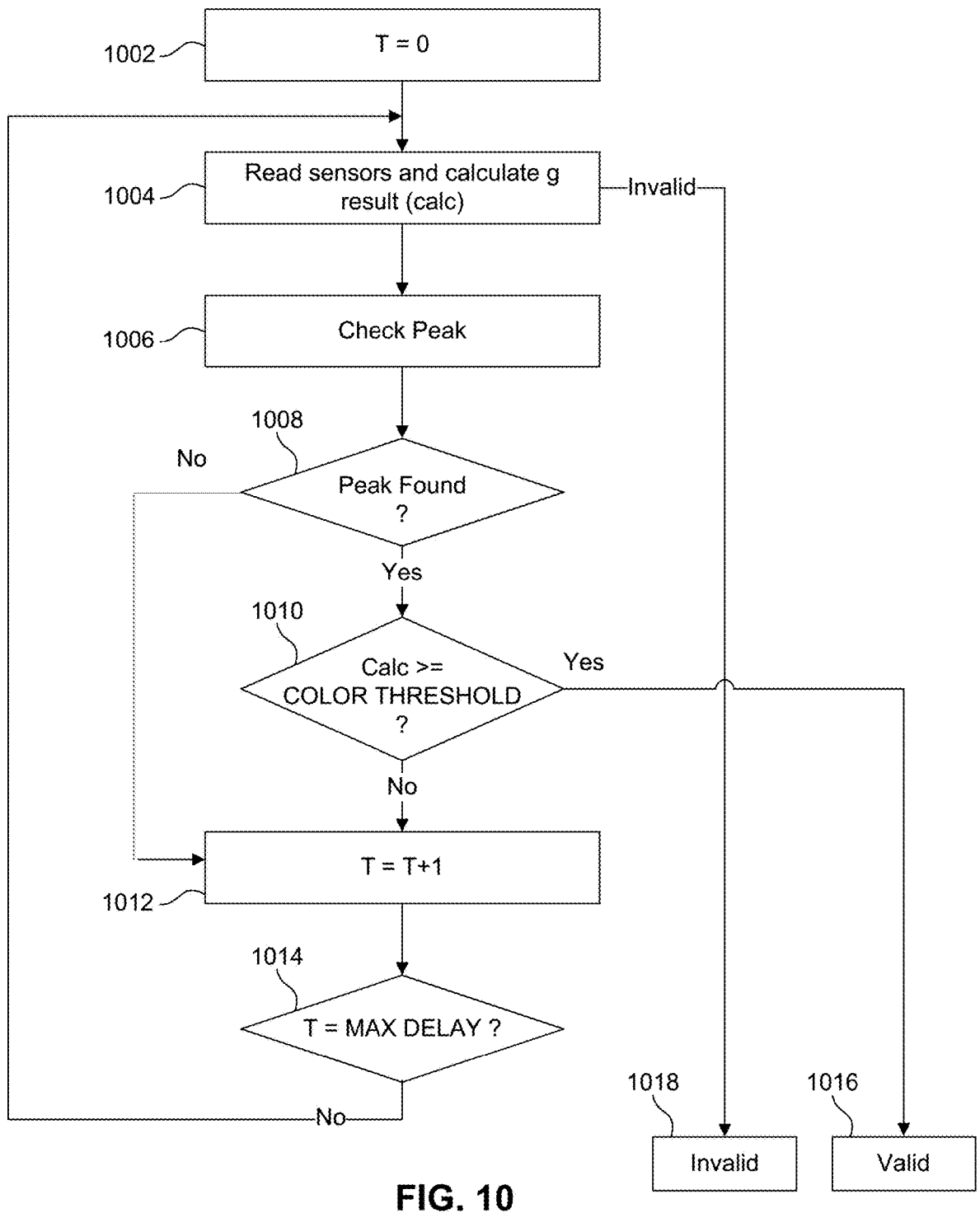

FIG. 10 is a flow chart of a method 1000. Method 1000 details the operation of step 808 of checking for enough colored particles such as colloidal gold, according to an example embodiment. In step 1002, liquid check component 734 initializes, sets to 0, resets, or clears counter 709.

In step 1004, color check component 736 invokes sampling component 740 to read measurements from rear sensor 18 and front sensor 23. Color check component 736 receives a calculated result (Calc) or an indication that an error occurred, i.e., the calculated result is invalid. If an error occurred, color check component 736 returns an invalid result in step 1018.

In step 1006, color check component 736 invokes peak-detection component 738. Peak-detection component 738 checks for a peak, and color check component 736 receives a peak-detection result from peak-detection component 738. Peak detection is further described below with respect to FIG. 12.

In step 1008, if the peak-detection result indicates that no peak was found, method 1000 proceeds to step 1012. Otherwise, method 1000 proceeds to step 1010.

In step 1010, color check component 736 determines whether the calculated result (Calc) exceeds the COLOR THRESHOLD parameter from operating parameters 712. The COLOR THRESHOLD may indicate that a sufficient amount or concentration of colored particles have been detected within the flowing sample-conjugate fluid as the lateral flow assay test progresses. When the calculated result exceeds the COLOR THRESHOLD, color check component 736 returns a valid result in step 1016. Otherwise, method 1000 proceeds to step 1012 where counter 709 is incremented. In an embodiment, instead of step 1012, counter 709 may be incremented by clock 728 while color check component 736 performs steps 1004-1010 and 1014-1018.

In step 1014, color check component 736 checks whether a value of counter 709 exceeds a MAX DELAY, e.g., 172 seconds or a corresponding number of clock cycles.

Figure 11:
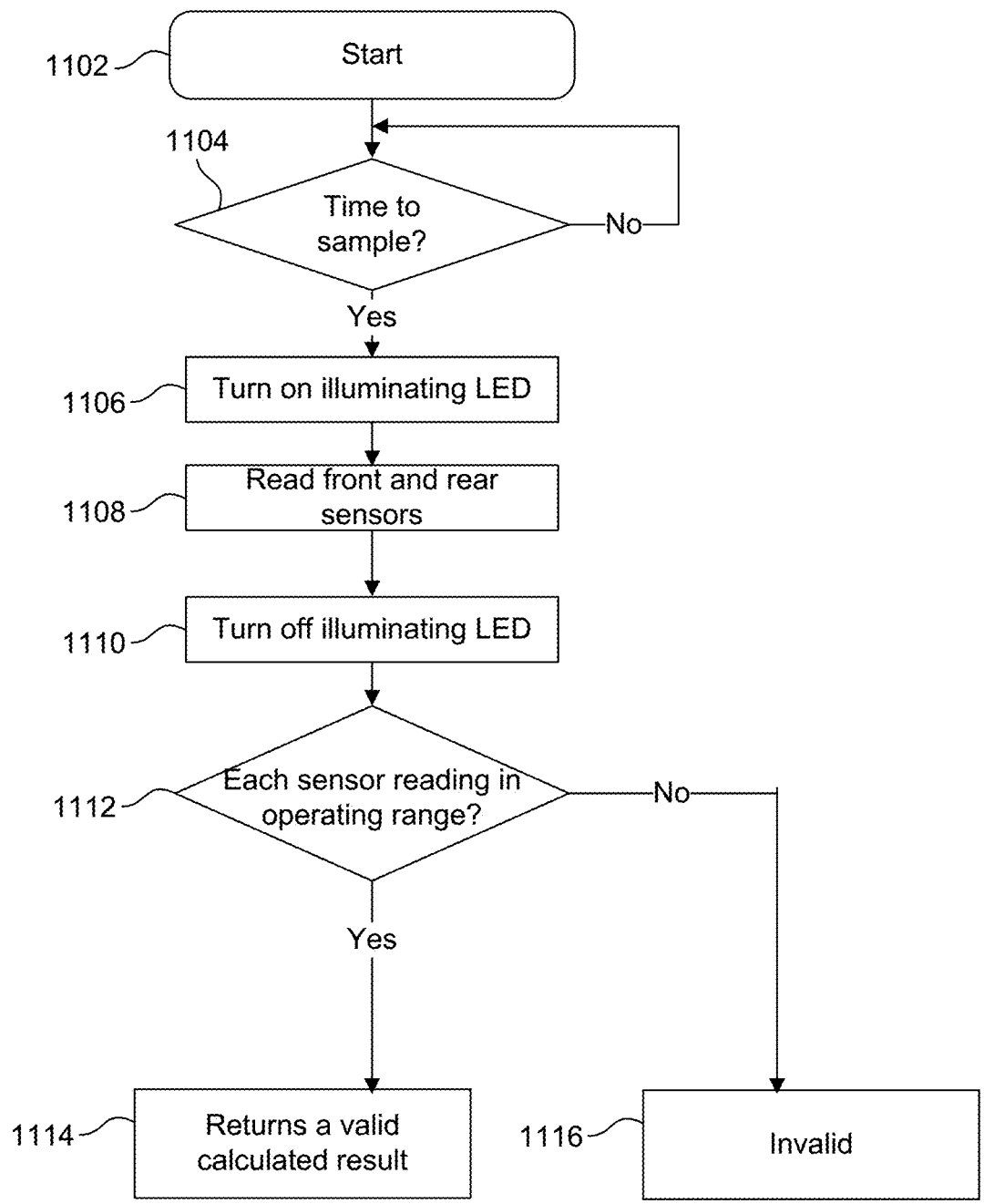

FIG. 11 is a flow chart of a method 1100. Method 1100 that details the operation of sampling component 740 (invoked by one or more steps of method 800 from FIG. 8) to read sensor values and calculate results, according to an example embodiment. Method 1100 starts at step 1102.

In step 1104, sampling component 740 determines whether a sampling time has elapsed before taking readings from rear sensor 18 and front sensor 23. In an embodiment, a sampling counter (not shown) in memory 704 may increment every clock cycle and resets in step 1106 after the sampling time has been reached or exceeded.

In step 1106, sampling component 740 turns on illuminating LED 67 so that an optical reflectance measurement may be read by front sensor 23 and rear sensor 18. In step 1108, sampling component 740 reads front sensor 23 and rear sensor 18, and stores read measurements in sensor readings 713A and B. Upon reading or storing the measurements, sampling component 740 turns off illuminating LED 67. In an embodiment, method 1100 may omit steps 1106 and 1110 to save on processing speed. But, more power may be required to keep illuminating LED 67 on for a longer period of time.

In step 1112, sampling component 740 checks whether each reading of front sensor 23 and rear sensor 18 are in a valid operating range as configured in operating parameters 712. For example, sampling component 740 may check whether all of the following conditions are met: front sensor reading>MIN FRONT SENSOR, rear sensor reading>MIN REAR SENSOR, front sensor reading<MAX FRONT SENSOR, and rear sensor reading<MAX REAR SENSOR. The capitalized variables indicate minimum and maximum threshold values for reading measurements of the front and rear sensors. In an embodiment, if one or more conditions fail, method 1100 proceeds to step 1116 and returns an error or an invalid result.

In step 1114, sampling component 740 returns a valid calculated result calculated using measurement readings from both rear sensor 18 and front sensor 23. For example, sampling component 740 may calculate the result using the following result equation: result=[(Ri/R)−(Fi/F)]*SF where, Fi=initial reading from front sensor 23;
F=current reading from front sensor 23;
Ri=initial reading from rear sensor 18;
R=current reading from rear sensor 18; and
SF=scaling factor, where the scaling factor is a large positive integer (e.g., 666) and is used to avoid values less than one in the calculated result.

Figure 12:
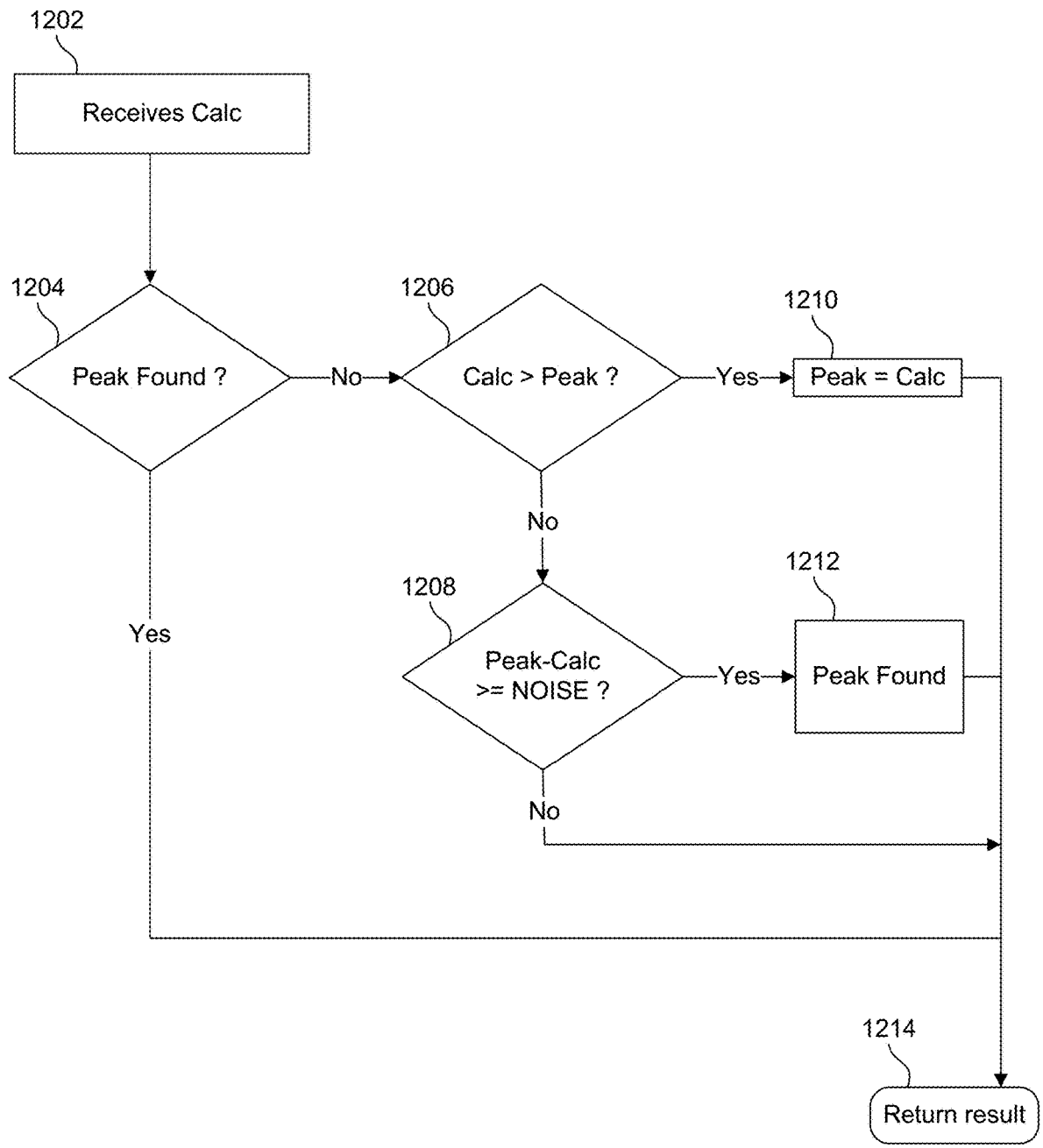

FIG. 12 is a flow chart of a method 1200. Method 1200 details the operation of step 1006 of method 1000, which determines whether a peak has been found, according to an example embodiment. In an embodiment, the peak may represent a maximum color intensity of line forming zone 65 as most of the sample-conjugate fluid has flowed past line forming zone 65 towards absorption pad 63. As described above, determining whether a pest, such as bed bugs, is present within the sample-conjugate fluid may be a time critical process. In an embodiment, a determined test or profile-evaluation result may only be valid within a specific range of elapsed time since the peak was detected.

In step 1202, peak-detection component 738 receives a calculated result (Calc) from color check component 736. Additionally, during a first iteration of step 1202, a peak value (Peak) may be initialized to 0.

In step 1204, peak-detection component 738 determines whether a peak has been found in a previous iteration of method 1200. In an embodiment, during a first iteration of step 1204, method 1200 may proceed to step 1206.

In step 1206, peak-detection component 738 compares the calculated result with Peak. If the calculated result exceeds Peak, method 1200 proceeds to step 1210, where peak-detection component 738 assigns Peak to the current calculated result.

In step 1208, peak-detection component 738 detects whether a difference between Peak and the calculated result exceeds a NOISE value, e.g., 9. Peak-detection component 738 may need to implement a noise filtering step such as step 1208 to eliminate a false-positive peak detection, i.e., detecting a peak that has not been reached.

In step 1212, if the difference between Peak and the calculated result exceeds NOISE, then peak-detection component 738 may be more confident that a peak has been found. In subsequent iterations of method 1200, step 1204 may indicate that a peak was previously found, i.e., in step 1212 of a previous iteration of method 1200.

In step 1214, peak-detection component 738 returns whether a peak was found.

Figure 13:
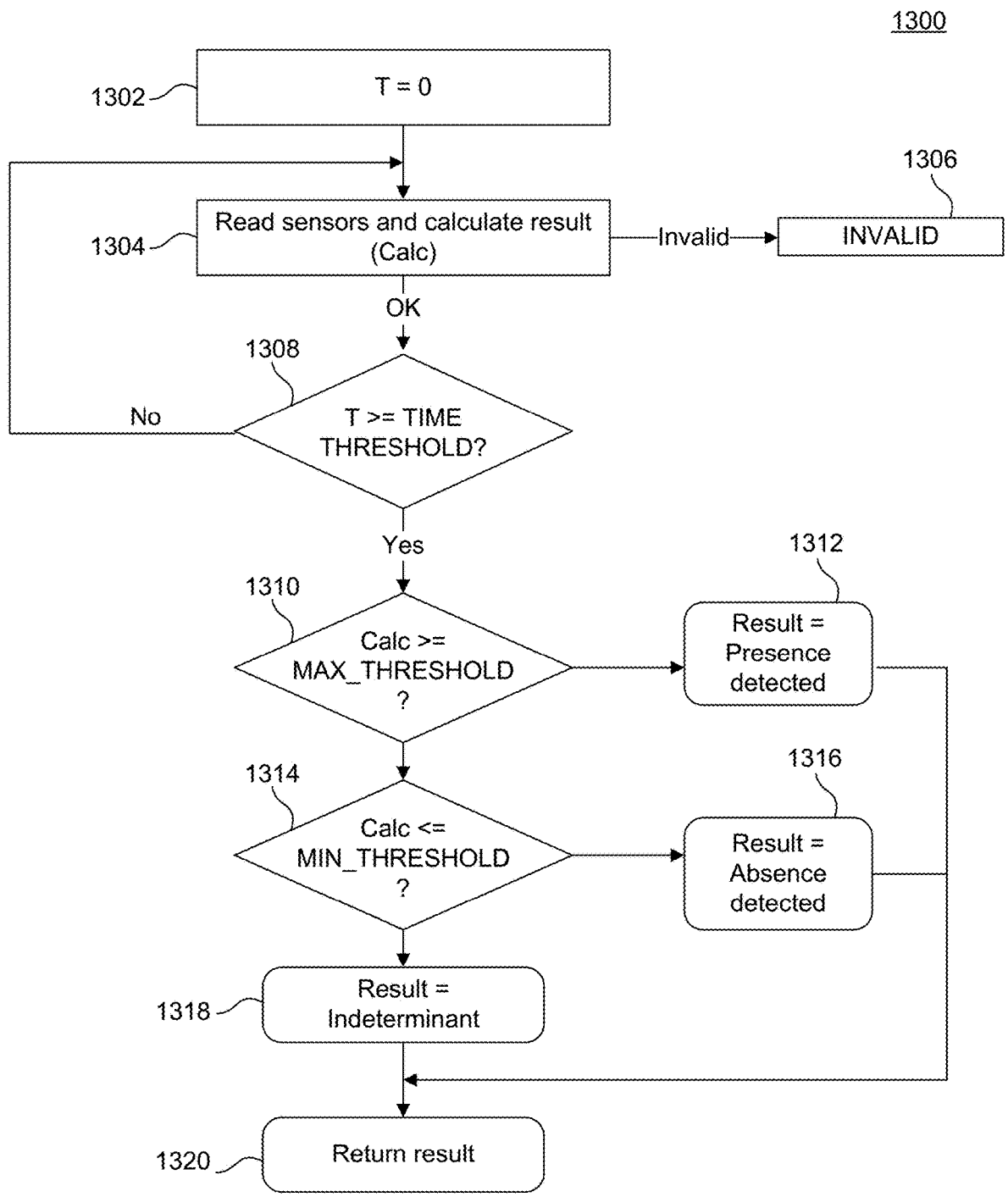

FIG. 13 is a flow chart of a method 1300. Method 1300 details the operations of step 810 of method 800, which determines a test result or a profile evaluation result for a pest profile, according to an example embodiment. In step 1302, profile evaluation component 742 initializes, sets to 0, resets, or clears counter 709.

In step 1304, profile evaluation component 742 invokes sampling component 740 to read measurements from rear sensor 18 and front sensor 23. Profile evaluation component 742 receives a calculated result (Calc) or an indication that an error occurred, i.e., the calculated result is invalid. If an error occurred, profile evaluation component 742 returns an invalid result in step 1306.

In step 1308, profile evaluation component 742 determines whether counter 709 has reached or exceeded a TIME THRESHOLD parameter, such as testing time threshold 710, for pest profile 706. In an embodiment, the TIME THRESHOLD parameter is a predetermined time period that is specific to a particular pest profile 706. If testing time threshold 710 has not been reached, method 1300 proceeds to step 1304, where sensor values are resampled.

In step 1310, profile evaluation component 742 determines whether the received calculated result from step 1304 has exceeded a MAX_THRESHOLD parameter, such as a max intensity threshold of testing threshold 708 for pest profile 706. If the calculated result exceeds the MAX_THRESHOLD, in step 1312, profile evaluation component 742 determines that pest profile 706 has been satisfied, and a presence of the pest associated with pest profile 706 was detected.

In step 1314, profile evaluation component 742 determines whether the received calculated result from step 1304 falls below a MIN_THRESHOLD parameter, such as a min intensity threshold of testing threshold 708 for pest profile 706. If the calculated result does not exceed or reaches the MIN_THRESHOLD, in step 1316, profile evaluation component 742 determines that pest profile 706 was not satisfied, and an absence of the pest associated with pest profile 706 was detected.

In step 1318, profile evaluation component 742 determines that due to the calculated result falling between MIN_THRESHOLD and MAX_THRESHOLD, the profile-evaluation result is indeterminate. By returning an indeterminate output, though method 1300 may not always produce a definitive result, i.e., detected presence or absence, method 1300 reduces false positives in pest detection.

In step 1320, the determined result of step 1312, 1316, or 1318 is returned.

In an embodiment, though method 1300 has been described with respect to one pest profile, method 1300 may be adapted to determine whether multiple pest profiles (e.g., from pest profile 706) are satisfied. In an embodiment, profile evaluation component 742 may be configured to perform method 1300 for each configured pest profile in pest profile 706, such that a profile-evaluation result is determined for each configured profile.

Returning to FIG. 7, each component of components 730-742 is further described below in turn:

Profile configuration component 730 configures the one or more pest profiles 706 to include specific thresholds for profile characteristics within pest profiles 706. The thresholds may be provided, for example, by a manufacturer of detection device 100. Profile configuration component 730 may be an optional component. In an embodiment, detection device 100 is simply pre-loaded or pre-configured with one or more pest profiles 706. Therefore, detection device 100 may run a single lateral flow assay test and detect a presence of more than one pest.

In an embodiment, detection device 100 can include a communication interface (e.g., a USB port or network port) for receiving new pest profiles 706 or updates to pest profiles 706. For example, detection device 100 may include a Bluetooth network chip (not shown) coupled to a network port of processor 702 (i.e., processor 21 of FIG. 1) such that a user or device manufacturer can add or program new profiles to pest profiles 706, add profile characteristics to existing pest profiles 706, or update one or more threshold values within existing pest profiles 706. Therefore, pest profile 706 can be dynamically configured via profile configuration component 730 to analyze a current incorporated test strip 16 in a specific lateral flow assay test.

Power-up test component 732 can determine when to activate processor 702 to start detecting for a presence of one or more pests. In an embodiment, power-up test component 732 can activate processor 702 when an activation signal is detected. For example, an activation signal can be detected when processor 702 is being powered (e.g., power port 720 receives power) or when ambient light is being detected by at least one sensor (e.g., readings from front sensor port 716 or rear sensor port 718). In an embodiment, during start-up of processor 702, power-up test component can initialize ports 714 and registers or data within memory 704.

Upon initialization, power-up test component 732 can launch a self-test sequence to verify that operating parameters 712 are being met. For example, power-up test component 732 may cycle through each LED, controlled by processor 702, to determine whether each of the LEDs are functioning. In an embodiment, upon start-up or initialization, the self-test sequence can include determining whether a detected ambient light is above a threshold stored in operating parameters 712. Power-up test component 712 can control one or more LEDs to blink or light up to indicate a current progress or self-test result. When self-test ends, sampling component 740 can be requested to take an initial reading of front sensor 23 and an initial reading of rear sensor 18.

Liquid check component 734 can detect whether a lateral flow assay test is currently being performed on test strip 16 of FIG. 2 based on measurements read from front sensor port 716 or rear sensor port 718. As described with respect to FIG. 2, a reading from a sensor can be a voltage value representative of an optical reflectance of incident light, e.g., color intensity, detected by the senor. In an embodiment, liquid check component 734 can call or invoke sampling component 740. Sampling component 740 reads from one or more sensors to obtain measurement readings used to calculate a result used by liquid check component 734 to calibrate front sensor 23 and back sensor 18, further explained above with respect to FIG. 9.

In a typical operation of the lateral flow assay test on test strip 16, sample fluid can flow from wick 56, through reagent pad 61, and past line forming zone 65 towards absorption pad 63. In an embodiment, liquid check component 734 receives a calculated result from sampling component 740. Sampling component 734 can then compare the calculated result with a liquid threshold in operating parameters 712 before determining to proceed with the detection algorithm or process. When the calculated result exceeds the liquid threshold, at least a portion of the sample fluid has reached the portion of test strip 16 opposite front sensor 23 or back sensor 18. Liquid check component 734 can further use the received calculated result to calibrate initial front and rear sensor readings (e.g., re-initialize initial sensor readings) if a current front sensor reading drifts from the previous initial front reading and the calculated result is near 0 indicating that no fluid liquid is being detected.

Color check component 736 can detect whether a sufficient amount of colored particles within reagent pad 61 has flowed past line formation zone 65 opposite front sensor 23. In an embodiment, if not enough colored particles migrate or flow past line formation zone 65, not enough sample-conjugate molecules may be captured. As a result, processor 702 may detect a false negative (i.e., detect an absence of one or more insect pests though an insect pest might be present). Color check component 736 can invoke or call sampling component 740. Sampling component 740 reads from front sensor 23 and rear sensor 18 to obtain sensor readings. The readings are needed by color check component 736 to determine whether a sufficient amount of colored particles has been detected. In an embodiment, color check component 736 can be called to start executing when liquid check component 734 detects the sample fluid.

In a typical operation of the lateral flow assay test, as more sample-conjugate fluid flows past line forming zone 65, the colored particles (e.g., colloidal gold) within the sample-conjugate fluid can intensify the coloration detected by front sensor 23 opposite line forming zone 65. When most of the sample-conjugate fluid has migrated to absorbent pad 63, fewer and fewer colored particles passing line forming zone 65 can be detected. Color check component 736 can use a calculated result from invoked sampling component 740 to determine a peak intensity in coloration, which indicates that most of the sample-conjugate fluid has migrated past line forming zone 65. Color check component 736 can invoke or call peak-detection component 736 to perform the peak detection.

Sampling component 740 can verify that each of front sensor 23 and rear sensor 18 are operating correctly before reading from the sensors to calculate a result. In an embodiment, after a sampling delay, sampling component 740 can sample and store readings from front sensor 23 and rear sensor 18 in sensor readings 713A and B, respectively. Sampling component 740 can also store a calculated result in memory 704. In an embodiment, sampling component 740 can determine whether a sensor is operating correctly by verifying that a sensor reading value is between operating thresholds for the sensor defined in operating parameters 712.

In an embodiment, sampling component 740 can calculate a result according to the following equation:

$$\text{result} = [(Ri/R) - (Fi/F)] * \text{SF where,}$$

Fi=initial reading from front sensor 23;
F=current reading from front sensor 23;
Ri=initial reading from rear sensor 18;
R=current reading from rear sensor 18; and
SF=scaling factor, where the scaling factor is a large positive integer (e.g., 666) and is used to avoid values less than one in the calculated result.

In an embodiment, the provided equation "result=[(Ri/R)−(Fi/F)]*SF" may be used by liquid check component 734, color check component 736, as well as profile evaluation component 742.

In an embodiment, by taking into account the relationship between initial and current sensor readings of both front sensor 23 and rear sensor 18 prior to testing, the calculated result accounts for environmental conditions to provide a more accurate testing result. Embodiments describing usage of and advantages provided by the above equation are described by U.S. Pat. No. 7,499,170 B2 titled "System and Method for Reading a Test Strip," herein incorporated in its entirety. Depending on the type of sensors being used, the calculated result may use a modified equation. For example, in an embodiment where a sensor is a photodiode, the following equation may be used instead: result=[(R/Ri)−(F/Fi)]*SF.

For example, during initializing and prior to testing, both front sensor 23 and rear sensor 18 can provide a proportional response or measurement readings, and both sensors can track in a similar fashion, because both sensors are exposed to the same environmental conditions and both sensors are exposed to a similar light source, i.e., illuminating LED 67. To clarify what is meant by the phrases "proportional response" and "track in a similar fashion," assume both sensors are exposed to a light source of a particular wavelength and intensity. Also assume that the spacing between both sensors and the light source are similar. The light would cause each sensor to produce an output response or reading measurement within each sensor's particular operating range. One output response could be greater than or less than the other output response without affecting the testing result. Now take the same two sensors and expose them to a light source with the same wavelength but with a lower intensity. The output response of each sensor can be smaller than the previous output response, which means they track in a similar fashion.

Profile evaluation component 742 can compare or match a calculated or stored calculated result against pest profile 706 to determine whether one or more pest profiles within pest profile 706 have been satisfied. Profile evaluation component 742 can call or invoke sampling component 740 to calculate or obtain the calculated result. In an embodiment, for each profile configured in pest profile 706, profile evaluation component 742 can wait for a minimum time within testing time threshold 710 before comparing the calculated result against each profile. This produces a profile-evaluation result for each insect pest. The time delay may be necessary for enough sample-conjugate molecules to react with immobilized antibodies in line forming zone 65 such that profile evaluation component 742 can determine a valid result.

In an embodiment, profile evaluation component 742 can compare the calculated result with, for example, a maximum intensity threshold within pest profile 706. This determines whether a presence of an insect pest associated with pest profile 706 is detected. Other comparisons can be made depending on profile characteristics stored in pest profiles 708. For example, a profile characteristic may include a rate of change of light intensity.

Upon determining whether one pest profile of pest profiles 706 has been met, profile evaluation component 742 can cause output ports 714 to light up one or more LEDs. This indicates a profile-evaluation result. For example, profile evaluation component 742 can power or light up red LED 32 to indicate a detected presence of bed bugs. That is, the profile-evaluation result is positive indicating that pest profile 506 of bed bugs has been met. In contrast, profile evaluation component 742 can light up green LED 29 when detecting an absence of bed bugs, i.e., the profile-evaluation result is negative. In an embodiment, profile evaluation component 742 can output a result (e.g., lighting up both green LED 29 and red LED 32) to indicate that the profile-evaluation result was indeterminate.

In an embodiment, profile evaluation component 742 can indicate a profile-evaluation result for each configured pest profile within pest profile 706. For example, result display 25 may include an LED-based device for each configured profile that is controlled to light up or change to a specific color to indicate each specific profile-evaluation result. In an embodiment, profile evaluation component 742 can display a severity of the detected presence of an insect pest based on an intensity of the coloration of line forming zone 65.

Figure 14:
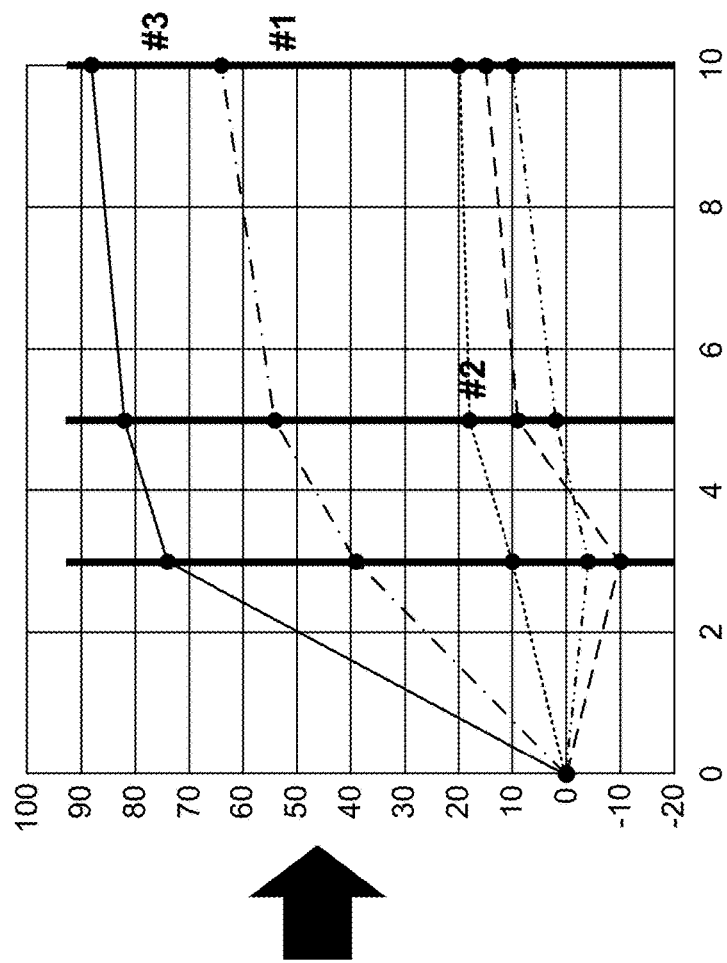
FIG. 14 is a diagram illustrating example results obtained for sample lateral flow assay tests analyzed by a detection device, according to an example embodiment.

FIG. 14 is a diagram illustrating example results obtained for sample lateral flow assay tests analyzed by the components of detection device 100 of FIG. 1, according to an example embodiment. As shown, the infestation intensity value table on the left shows calculated results for six sample lateral flow assay tests run on the same detection device, such as detection device 100 of FIG. 1. For each assay test, sampling component 740 can store calculated results at three sampling times: 3 min, 5 min, and 10 min.

In an embodiment, pest profile 706 can include a bed bugs profile including, for example, a min intensity threshold of 9, a max intensity threshold of 15, and a testing time threshold between 4 minutes and 6 minutes. For example, the testing time threshold may be 5 minutes. This testing time threshold is a predetermined time specific to the bed bugs profile. Sample results of assay tests 1-3 exceed the max intensity threshold at the 5 minute mark. Sample result of assay test 6 falls between the min and max intensity thresholds. And, calculated result of assay test 5 falls below the min intensity threshold. Therefore, profile evaluation component 742 can control LEDs to indicate a presence of bed bugs for assay tests 1-3, an absence of bed bugs for assay test 5, and an indeterminate result for assay test 6. In an embodiment, a bed bug profile can include severity thresholds such that profile evaluation results for assay tests 1-3 indicate a medium severity, a low severity, and a high severity, respectively. One or more LEDs can be controlled to indicate the severity of infestation levels by, for example, lighting up, blinking at a specific rate, or emitting light at a specific intensity.

In an embodiment, pest profile 706 can include the described bed bugs profile and a cockroach profile including, for example, a min intensity threshold of 11, a max intensity threshold of 14, and a testing time threshold between 9 minutes and 11 minutes. Although at sampling time 10 min, assay tests 1-3 and 6 may each exceed the max intensity threshold of 14, profile evaluation component 742 may only indicate a detected presence of cockroaches for assay test 6. Therefore, in an embodiment, processor 702 can be a prioritized insect pest detector. The types of possibly detected pests can be prioritized based on testing time thresholds from the least delay to the most delay. For example, processor 702 can be configured to first detect whether bed bugs are present at the 5 min sampling time before second detecting whether cockroaches are present at the 10 min sampling time.

To field test the effectiveness of detection device 100 of FIG. 1, having processor 702 of FIG. 7 and operating according to the methods of FIGS. 8-13, 17 bed bugs-infested beds were tested. In this field test, each of the 17 beds was visually confirmed to have at least 10 live bed bugs. In this example field test, a sample fluid was created for each of the 17 beds and applied to detection device 100 for detecting prior or present bed bugs infestation. Briefly, as described with respect to FIG. 1, the sample fluid was created by first using a swabbing material and a standardized collection procedure to swab each bed and then dipping the swabbing material into an extract buffer.

In this example field test, the bed bugs detection result for each of the 17 beds was generated and displayed after 10 minutes. As discussed above with respect to pest profile 706, this testing time of 10 minutes is an example time period specific to bed bugs. Implementing the methods of FIGS. 8-13, detection device 100 detected prior or present bed bugs infestation in 13 of the 17 bed bugs-infested beds. Thus, this example field test shows that by using detection device 100, a pest control operator can determine bed bugs infestations on site and within a short time span, e.g., within 10 minutes, with high accuracy. The pest control operator would not need to rely on current detection methods such as obtaining a sample of suspected bed bug residue to be tested at an off-site testing lab, which often requires 24 to 48 hours to produce a test result.

Any of the above embodiments can include the following monoclonal anti-bed bug antibodies or antigen-binding fragments thereof, mutants, conjugated antibodies or conjugated antigen-binding fragments, compositions, kits, hybridomas, polynucleotides, polypeptides, vectors, cells, or methods, as disclosed in U.S. Provisional Patent Application No. 62/244, 189 filed on Oct. 21, 2015, titled "Anti-bed bug monoclonal antibodies and methods of making and uses thereof," which is incorporated by reference herein in its entirety.

Terminology

As used herein, the term "bed bug" refers to any *Cimex* species or strain thereof.

The terms "antibody" and "antibodies" are terms of art and can be used interchangeably herein to refer to a molecule or molecules with an antigen-binding site that specifically binds an antigen.

The term "monoclonal antibody" refers to a homogeneous antibody population involved in the specific recognition and binding of a single antigenic determinant, or epitope. This is in contrast to polyclonal antibodies that typically include different antibodies directed against different antigenic determinants. Furthermore, "monoclonal antibody" refers to such antibodies made in any number of manners, including, but not limited to, by hybridoma, phage selection, recombinant expression, and transgenic animals.

The term "antigen-binding fragment" refers to a portion of an antibody that is capable of specifically binding to an antigen. Examples of antibody fragments include, but are not limited to heavy chain variable region fragments, light chain variable region fragments, Fab, Fab', F(ab')2, scFv fragments, Fv fragments, linear antibodies, single chain antibodies, multispecific antibodies, minibodies, diabodies, triabodies, and tetrabodies.

The terms "variable region" or "variable domain" are terms of art and can be used interchangeably herein to refer to a portion of an antibody that differs extensively in sequence among antibodies and is used in the binding and specificity of a particular antibody for its particular antigen. The variable regions of the heavy and light chain each consist of four framework regions (FR) connected by three complementarity determining regions (CDRs) also known as hypervariable regions. The CDRs in each chain contribute to the formation of the antigen-binding site of antibodies.

The term "specifically binds" refers to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art.

As used herein, the term "detecting" encompasses quantitative and qualitative detection.

As used herein, the term "effective amount" refers to the amount of that achieves a desired effect.

As used herein, the terms "host cell" and "cell" can be used interchangeably and can refer to any type of cell, e.g., a primary cell, a cell in culture, or a cell from a cell line, including a hybridoma.

An antibody, antigen-binding fragment, host cell, and cell as referred to herein includes "isolated" forms that have been separated or recovered from a component of their native environment, such as separation or removal from contaminants that would interfere with uses of the antibody, antigen-binding fragment, host cell, or cell, in which such contaminants may include enzymes, hormones, and other proteinaceous or nonproteinaceous materials.

The embodiments can include an antibody produced by the hybridoma deposited at the American Type Culture Collection (ATCC) under Accession Number PTA-122644, or an antigen-binding fragment thereof. The anti-bed bug monoclonal antibody designated herein as BB2 is produced by the hybridoma deposited at the ATCC under Accession Number PTA-122644.

The embodiments can include an antibody produced by the hybridoma deposited at the ATCC under Accession Number PTA-122645, or an antigen-binding fragment thereof. The anti-bed bug monoclonal antibody designated herein as BB7 is produced by the hybridoma deposited at the ATCC under Accession Number PTA-122645

The embodiments can include a monoclonal antibody or an antigen binding fragment thereof comprising the heavy chain and light chain complementarity determining regions (CDRs) of the antibody produced by the hybridoma deposited at the ATCC under Accession Number PTA-122644 [BB2] or the antibody produced by the hybridoma deposited at the ATCC under Accession Number PTA-122645 [BB7] (see, e.g., the discussion of CDRs in Kabat et al., U.S. Dept. of Health and Human Services, "Sequences of Proteins of Immunological Interest" (1983), and Chothia et al., *J. Mol. Biol.* 196:901-917 (1987)). Methods for determining CDRs are well-known, including an approach based on cross-species sequence variability (i.e., Kabat et al. Sequences of Proteins of Immunological Interest, (5th ed., 1991, National Institutes of Health, Bethesda, MD)), and an approach based on crystallographic studies of antigen-antibody complexes (Al-lazikani et al., *J. Molec. Biol.* 273:927-948 (1997)). In addition, combinations of these two approaches can be used to determine CDRs. CDRs also can be determined according to Lefranc M-P, *The Immunologist* 7: 132-136 (1999); Lefranc M-P, et al., *Nucleic Acids Res* 27: 209-212 (1999); MacCallum R M et al., *J. Mol. Biol.* 262: 732-745 (1996); Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001); and Oxford Molecular's AbM antibody modeling software (Oxford Molecular Group, Inc.).

The embodiments can include an antibody or antigen-binding fragment thereof that comprises the heavy and light chain variable regions of the antibody produced by the hybridoma deposited at the ATCC under Accession Number PTA-122644 [BB2] or the antibody produced by the hybridoma deposited at the ATCC under Accession Number PTA-122645 [BB7]. Generally, a variable region is located at about the amino-terminal 110 to 120 amino acids in the mature heavy chain and about the amino-terminal 90 to 115 amino acids in the mature light chain.

The embodiments can include an antibody or antigen-binding fragment thereof that comprises the heavy and light chains of the antibody produced by the hybridoma deposited at the ATCC under Accession Number PTA-122644 [BB2] or the antibody produced by the hybridoma deposited at the ATCC under Accession Number PTA-122645 [BB7]. Each heavy chain comprises a heavy chain variable region and a heavy chain constant region. The heavy chain constant region comprises three domains, CH1, CH2 and CH3. Each light chain comprises a light chain variable region and a light chain constant region. The light chain constant region comprises one domain (CL1).

The monoclonal antibodies included in the embodiments can be, but are not limited to, recombinantly produced antibodies, human antibodies, humanized antibodies, chimeric antibodies, multispecific antibodies such as bispecific antibodies, fusion proteins comprising an antigen determination portion of an antibody, and any other modified immunoglobulin molecule comprising an antigen recognition site so long as the antibodies exhibit the desired activity. Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclass (e.g., $IgG_{2a}$ or $IgG_{2b}$) of immunoglobulin molecule. Techniques for the production of antibodies will be apparent to the skilled practitioner.

Monoclonal antibodies can be prepared, for example, using hybridoma methods, such as those described by Kohler and Milstein, *Nature* 256:495 (1975). Using the hybridoma method, a mouse, a hamster, or another appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells.

Monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which allow for generation of monoclonal antibodies when transfected into host cells, including, but not limited to, *E. coli* cells, simian COS cells, Chinese hamster ovary (CHO) cells, or myeloma cells. Also, recombinant monoclonal antibodies or fragments thereof of the desired species can be isolated from phage display libraries expressing CDRs of the desired species (see, e.g., McCafferty et al., *Nature* 348:552-554 (1990); Clackson et al., *Nature* 352:624-628 (1991); and Marks et al., *J. Mol. Biol.* 222:581-597 (1991)).

Antigen-binding fragments in the embodiments can be produced by any known method and include a portion of an antibody that is capable of specifically binding to an antigen. Examples of antibody fragments include, but are not limited to, heavy chain variable region fragments, light chain variable region fragments, Fab, Fab', F(ab')2, scFv fragments, Fv fragments, linear antibodies, single chain antibodies, multispecific antibodies, minibodies, diabodies, triabodies, and tetrabodies (see, e.g., Hudson and Souriau, *Nature Med.* 9: 129-134 (2003) and U.S. Pat. No. 5,641,870). Traditionally, these fragments are derived via proteolytic digestion of intact antibodies (see, e.g., Morimoto et al., *Journal of Biochemical and Biophysical Methods* 24:107-117 (1993); Brennan et al., *Science* 229:81 (1985)). In certain embodiments, antibody fragments are produced recombinantly. For example, antibody fragments can be expressed in and secreted from *E. coli* or other host cells, thus allowing the production of large amounts of the fragments. Such antibody fragments can also be isolated from the antibody phage libraries. Other techniques for the production of antibody fragments will be apparent to the skilled practitioner.

In certain embodiments, any of the antibodies or antigen-binding fragments thereof in the embodiments can be capable of binding to a bed bug antigen in a lysate of whole bed bugs or an extract of collection paper comprising bed bug waste material. The methods for producing lysates of whole bed bugs and extracts of collection paper comprising bed bug waste material will be apparent to the skilled practitioner based on known extraction techniques and the methods disclosed herein. Whole bed bugs include nymphs, males, and/or females can be obtained from an area of infestation or an experimentally or commercially maintained bed bug colony, and can include any *Cimex* species or strain, including, but not limited to, *Cimex lectularius* and the Harlan strain. Collection paper comprising bed bug waste material can include bed bug excreta and/or tissues, for example, and can be obtained from commercial sources (e.g., i2LResearch USA Inc., Baltimore, Maryland, USA).

The embodiments can include a mutant of the antibody produced by the hybridoma deposited at the ATCC under Accession Number PTA-122644 [BB2] or the antibody produced by the hybridoma deposited at the ATCC under Accession Number PTA-122645 [BB7]. Mutants can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art. Mutations can also include deletions, insertions, inversions, and repeats. Mutations can be introduced by general molecular biology methods known in the art including, but not limited to, error-prone PCR, oligonucleotide-directed mutagenesis, site-directed mutagenesis, and heavy or light chain shuffling.

The embodiments can include a monoclonal antibody or antigen-binding fragment thereof having one or more characteristics that are substantially similar to those of the antibody produced by the hybridoma deposited at the ATCC under Accession Number PTA-122644 [BB2] or the antibody produced by the hybridoma deposited at the ATCC under Accession Number PTA-122645 [BB7]. The phrase "substantially similar" as used herein denotes a sufficiently high degree of similarity between two characteristics such that one of skill in the art would consider the difference to be of little or no biological and/or statistical significance. In certain embodiments, the difference between two numerical values can be less than about 15%, 10%, 5%, 2%, or 1%. The characteristics of the deposited antibodies can include one or more properties, such as, but not limited to, binding specificity (e.g., Kd value), antigenic determinants/epitope, and polynucleotide or polypeptide sequences. In certain embodiments, the monoclonal antibody or antigen-binding fragment thereof has a polynucleotide or polypeptide sequence that is at least 90%-99%, at least 95%-99%, at least 90%, at least 95%, at least 96%, at least 97%, at least 98%, or at least 99% identical to the polynucleotide or polypeptide sequence of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the monoclonal antibody or antigen-binding fragment thereof has one or more of the same characteristics as the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the monoclonal antibody or antigen-binding fragment thereof binds to the same antigenic determinant/epitope as the antibody produced by the hybridoma deposited at the ATCC under Accession Number PTA-122644 [BB2] or the antibody produced by the hybridoma deposited at the ATCC under Accession Number PTA-122645 [BB7].

The term "epitope" or "antigenic determinant" can be used interchangeably herein to refer to that portion of an antigen capable of being recognized and specifically bound by a particular antibody. An epitope typically includes at least 3, and more usually, at least 5 or 8-10 amino acids in a unique spatial conformation. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). The epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

The embodiments can include a conjugated monoclonal antibody or conjugated antigen-binding fragment comprising any of the antibodies, antigen binding fragments, or mutants described herein and a detection agent, including detection agents described above. The detection agent can be conjugated directly or indirectly to the antibody, antigen-binding fragment, or mutant. The detection agent can be detectable by itself or, in the case of an enzymatic label, can catalyze chemical alteration of a substrate compound or composition which is detectable. The detection agent includes, but is not limited to, a radiolabel, a fluorophore, a chromophore, an imaging agent, or a metal, including a metal ion. In certain embodiments, the detection agent is colloidal gold or gold nanoparticles. In certain embodiments, the colloidal gold or gold nanoparticles is comprised of gold particles having a size of 1-300 nm, 1-250 nm, 10-200 nm, 20-150 nm, 20-100 nm, 20-80 nm, 20-60 nm, 20-50 nm, 20 nm, 30 nm, 40 nm, 50 nm, 60 nm, 70 nm, 80 nm, 90 nm, 100 nm, 150 nm, 200 nm, 250 nm, or 300 nm. In certain embodiments, the conjugated antibody or conjugated antigen-binding fragment comprises the antibody produced by the hybridoma deposited at the ATCC under Accession Number PTA-122644 [BB2], or an antigen-binding fragment thereof, or the antibody produced by the hybridoma deposited at the ATCC under Accession Number PTA-122645 [BB7], or an antigen-binding fragment thereof.

The embodiments can include a composition comprising any of the antibodies or antigen binding fragments thereof, mutants, or conjugated antibodies or conjugated antigen-binding fragments herein, or a combination thereof. In certain embodiments, the composition comprises the antibody produced by the hybridoma deposited at the ATCC under Accession Number PTA-122644 [BB2] and the antibody produced by the hybridoma deposited at the ATCC under Accession Number PTA-122645 [BB7]. In certain embodiments, the composition comprises the antibody produced by the hybridoma deposited at the ATCC under Accession Number PTA-122644 [BB2], and a conjugated antibody comprising the antibody produced by the hybridoma deposited at the ATCC under Accession Number PTA-122645 [BB7] and a detection agent. In certain embodiments, the composition comprises the antibody produced by the hybridoma deposited at the ATCC under Accession Number PTA-122645 [BB7], and a conjugated antibody comprising the antibody produced by the hybridoma deposited at the ATCC under Accession Number PTA-122644 [BB2] and a detection agent.

The embodiments can include a kit comprising any of the antibodies or antigen binding fragments thereof, mutants, conjugated antibodies or conjugated antigen-binding fragments, or compositions herein, or a combination thereof. In certain embodiments, a kit comprises at least one component in one or more containers. In some embodiments, the kit comprises components necessary and/or sufficient to perform a detection assay, including controls, directions for performing assays, any necessary device, and/or software for analysis and presentation of results. Suitable devices include those disclosed in U.S. Pat. Nos. 7,220,597 and 7,214,542, both of which are incorporated by reference herein in their entireties.

The embodiments can include a hybridoma capable of producing an antibody, wherein the hybridoma is deposited at the ATCC under Accession Number PTA-122644 [BB2] or wherein the hybridoma is deposited at the ATCC under Accession Number PTA-122645 [BB7].

The embodiments can include an isolated polypeptide comprising an amino acid sequence at least 90%-99%, at least 95%-99%, at least 90%, at least 95%, at least 96%, at least 97%, at least 98% or at least 99% identical to an amino acid sequence of a heavy or light chain variable region, or a heavy or light chain, of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polypeptide comprises the amino acid sequences of the CDRs of a heavy or light chain variable region of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polypeptide comprises the amino acid sequences of the heavy or light chain variable region, or heavy or light chain, of the antibody produced by the hybridoma deposited at the ATCC under Accession Number PTA-122644 [BB2] or the antibody produced by the hybridoma deposited at the ATCC under Accession Number PTA-122645 [BB7].

The embodiments can include an isolated polynucleotide comprising a nucleic acid sequence at least 90%-99%, at least 95%-99%, at least 90%, at least 95%, at least 96%, at least 97%, at least 98% or at least 99% identical to a nucleic acid sequence encoding a heavy or light chain variable region, or a heavy or light chain, of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polynucleotide comprises nucleic acid sequences encoding the CDRs of a heavy or light chain variable region of the antibody produced by the hybridoma deposited at the ATCC under Accession Number PTA-122644 [BB2] or the antibody produced by the hybridoma deposited at the ATCC under Accession Number PTA-122645 [BB7]. In certain embodiments, the polynucleotide comprises a nucleic acid sequence encoding the heavy or light chain variable region, or heavy or light chain, of the antibody produced by the hybridoma deposited at the ATCC under Accession Number PTA-122644 [BB2] or the antibody produced by the hybridoma deposited at the ATCC under Accession Number PTA-122645 [BB7].

The embodiments can include a vector comprising one or more of the isolated polynucleotides of the invention. In certain embodiments, the vector is an expression vector.

The embodiments can include an isolated cell producing an antibody, antigen-binding fragment, or mutant of the invention. In certain embodiments, the cell is a hybridoma. In certain embodiments, the cell comprises one or more vectors of the invention. In certain embodiments, the cell comprises one or more polynucleotides of the invention.

The embodiments can include a method of making an antibody, antigen-binding fragment, or mutant of the invention, comprising culturing an isolated cell producing the antibody, antigen-binding fragment, or mutant, and isolating the antibody, antigen-binding fragment, or mutant from the cultured cell.

Cells include, but are not limited to, hybridomas, prokaryotes, yeast, insect, or higher eukaryotic cells. Hybridomas that produce monoclonal antibodies can be propagated either in vitro culture using standard methods (Goding, Monoclonal Antibodies: Principles and Practice, Academic Press, 1986) or in vivo as ascites tumors in an animal. Prokaryotes include gram negative or gram positive organisms, for example E. coli or bacilli. Higher eukaryotic cells include, but are not limited to, established cell lines of mammalian origin. Examples of suitable mammalian cell lines include COS-7, L, C127, 3T3, Chinese hamster ovary (CHO), HeLa, and BHK cell lines. In certain embodiments, any of the antibodies, antigen-binding fragments, or mutants of the invention are produced by isolated cells following transfection of the cells with vectors comprising polynucleotides encoding the sequences of the antibodies, antigen-binding fragments, or mutants of the invention. Appropriate cloning and expression vectors for use with bacterial, fungal, yeast, and mammalian cellular hosts are described by Pouwels et al. (Cloning Vectors: A Laboratory Manual, Elsevier, N.Y., 1985). Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The antibodies, antigen-binding fragments, or mutants of the invention can be isolated from the cells or culture medium, or from ascites fluid for in vivo propagation of hybridomas. Isolation of the antibodies, antigen-binding fragments, or mutants can be according to any suitable method. Such standard methods include chromatography (e.g., ion exchange, affinity and sizing column chromatography), centrifugation, differential solubility, or by any other standard technique for protein purification. Methods known in the art for purifying antibodies and other proteins include, for example, those described in U.S. Patent Publication Nos. 2008/0312425, 2008/0177048, and 2009/0187005.

The embodiments can include a method of detecting bed bugs, comprising contacting a sample comprising a bed bug antigen with any of the antibodies, antigen-binding fragments, mutants, conjugated antibodies or conjugated antigen-binding fragments, or compositions of the invention, or a combination thereof, and detecting binding of the bed bug antigen to the antibody or antigen-binding fragment, mutant, conjugated antibody or conjugated antigen-binding fragment, composition, or combination thereof. "A sample" includes, but is not limited to, whole bed bugs, bed bugs parts, bed bug waste material, lysates or extracts thereof, extracts of collection paper comprising bed bug waste material, and fluids containing the same.

The contacting can be by any suitable method. In certain embodiments, the contacting is by application of a sample comprising the bed bug antigen to an antibody, antigen-binding fragment, mutant, conjugated antibody or conjugated antigen-binding fragment, or composition of the invention, or a combination thereof that is immobilized or otherwise located on a surface. Any acceptable surface can be used, as will be appreciated by the skilled practitioner, including, but not limited to, a nitrocellulose membrane or a pad composed of a suitable material, and can include a sandwich, well, or lateral flow design. In certain embodiments, the sample is contacted with an antibody of the invention and a conjugated antibody of the invention. In certain embodiments, the antibody is produced by the hybridoma deposited at the ATCC under Accession Number PTA-122644 [BB2], and the conjugated antibody comprises the antibody produced by the hybridoma deposited at the ATCC under Accession Number PTA-122645 [BB7] and a detection agent. In certain embodiments, the antibody is produced by the hybridoma deposited at the ATCC under Accession Number PTA-122645 [BB7], and the conjugated antibody comprises the antibody produced by the hybridoma deposited at the ATCC under Accession Number PTA-122644 [BB2] and a detection agent. In certain embodiments, the contacting further comprises contacting the antibody, antigen-binding fragment, mutant, conjugated antibody or conjugated antigen-binding fragment, or composition of the invention, or a combination thereof with a control sample for comparison with the test sample.

The detecting can be by any suitable method and can include quantitative or qualtitative detection. Such methods include, but are not limited to, antigen-binding assays that are well known in the art, such as lateral flow assays, radioimmunoassays, ELISA (enzyme linked immunosorbent assay), "sandwich" immunoassays, immunoprecipitation assays, fluorescent immunoassays, protein A immunoassays, and immunohistochemistry (IHC). The detection can include visual analysis of a colorimetric, fluorescent, or luminescent reaction, for example, or can include use of a device that measures such reactions. Suitable devices include those disclosed in U.S. Pat. Nos. 7,220,597 and 7,214,542, both of which are incorporated by reference herein in their entireties, as well as a device disclosed herein. In certain embodiments, the detecting comprises performing a lateral flow assay. In certain embodiments, the detecting occurs in 1-20 minutes, 1-15 minutes, 1-10 minutes, 1-5 minutes, 20 minutes or less, 15 minutes or less, 10 minutes or less, 5 minutes or less, within 20 minutes, within 15 minutes, within 10 minutes, or within 5 minutes.

The amount of the antibody, antigen-binding fragment, mutant, conjugated antibody or antigen-binding fragment, composition of the invention, or a combination thereof can include any effective amount, which will be apparent to a skilled practitioner based on known detection methods and the methods disclosed in the examples. The sample can be diluted or undiluted.

In certain embodiments, the method further comprises collecting a sample comprising the bed bug antigen with a collection device and extracting antigens from the sample. The sample can be collected from any surface associated with bed bug infestation, including, but not limited to, bedding, mattresses, upholstery, carpets, rugs, and furniture. The collection device can be any suitable device, including but not limited to a swab, such as a cotton swab, a vacuum, or any material that can be used to collect residue including, but not limited to, a wipe, tissue, or towelette. In certain embodiments the collection device is a swab. In certain embodiments, extracting antigens from the sample comprises solubilizing antigens in the sample with an extraction buffer. Suitable extraction buffers will be apparent to the skilled practitioner in view of well-known extraction buffers and those disclosed in the examples.

Properties of the BB2 and BB7 antibodies are disclosed in the following examples, which are offered by way of illustration, and not by way of limitation.

EXAMPLE 1

Generation of Anti-Bed Bug Monoclonal Antibodies

Mice were immunized with whole bed bug lysates and bed bug paper extracts (i.e., extracts from bed bug collection paper containing waste material from a bed bug colony).

Whole bed bug lysates were produced from nymphs, males, and females from a bed bug colony (Harlan strain, i2LResearch USA Inc., Baltimore, Maryland, USA) that were frozen and triturated in 1× phosphate buffered saline (PBS). The lysates were clarified by 0.45 micron syringe filter. Protein concentration was determined by a standard Bradford protein assay. The clarified, quantified extracts were aliquoted into 1.5 mL Eppendorf tubes and stored at −80° C.

Bed bug collection paper (i2LResearch USA Inc., Baltimore, Maryland, USA) was cut into approximately 1 cm$^2$ pieces and placed into 2 mL plastic centrifuge tubes. Extraction was performed by adding 1.0 mL of 50 mM PBS (pH 7.4) and mixing the tubes for 30 minutes on a tube rocker. After 30 minutes, the extract was fully extracted by passing the mixture through a 5 mL syringe. This collected extract was then used to obtain more extract from fresh collection paper by serially adding the extract to the newly cut paper and repeating the process. The final extract was then centrifuged at 12,000 rpm for 10 minutes to remove particulates. The supernatant was removed and retained, and the pelleted material was discarded. The protein concentration of the supernatant was determined by Bradford assay to be 0.6 mg/mL. The final solution (i.e., "bed bug paper extract") was stored at −20° C.

Four 4-5 week old Balb/c mice (Harlan Laboratories, Inc., Indianapolis, Indiana, USA) were immunized subcutaneously in the back with 50 μg whole bed bug lysate mixed with 100 μl of adjuvant. The adjuvant used for two of the mice was a traditional adjuvant (Freund's Adjuvant, Sigma-Aldrich Co. LLC, St. Louis, Missouri, USA) and the adjuvant used for the remaining two mice was a water-soluble adjuvant (ImmuQuik®, KCH Scientific, San Jose, California, USA).

At Day 14 after the initial immunization, the immunized mice were boosted with 50 μg whole bed bug lysate mixed with 100 μl of an adjuvant as originally used for each mouse. At Day 37, sera from the mice were titer-tested using a standard enzyme immunoassay, using goat anti-mouse horseradish peroxidase conjugated antibody as the secondary antibody/enzyme conjugate and 3,3',5,5'-Tetramethylbenzidine as the chromogenic substrate, and 10 μg/ml whole bed bug lysate as the source of antigen. The two mice immunized with whole bed bug lysate in the water-soluble adjuvant produced higher titers. However, since the titers were not strong overall, all four immunized mice were boosted with double the amount of whole bed bug lysate (i.e., 100 μg) at Day 51 and then again at Day 78. At Day 107, the four mice were boosted with 15 μl of bed bug paper extract. At Day 117, the mouse with the highest previous titer was titer-tested using whole bed bug lysate or bed bug paper extract as the source of antigen. A weak reaction was observed for bed bug paper extract. At Day 134, all four mice were boosted with 100 μl of bed bug paper extract using ImmuQuik® as the adjuvant. At Day 151, the mice were titer tested using bed bug paper extract as the source of antigen, and the highest titer mouse was boosted with 100 μl bed bug paper extract.

Spleen cells were collected from the two highest titer mice, one at Day 154 and the other at Day 216, and fused with murine SP 2/0 myeloma cells by using polyethylene glycol. The fused cells were cultured in selection medium for 10 days, followed by screening with bed bug paper extract as the source of antigen. About 41 positive clones were identified from primary screening, and about 25 positive clones were confirmed in secondary screening. Stable cell lines were subcloned, ascites were produced for more than 25 clones, and antibodies were purified (e.g., in amounts of 2-5 mg). Two antibodies referred to herein as the BB2 and BB7 antibodies were determined by enzyme immunoassay to have a strong reaction with bed bug paper extract as compared to antibodies from other clones and were selected for further study. Hybridomas producing the BB2 and BB7 antibodies were deposited under the Budapest Treaty at the American Type Culture Collection, Patent Depository, 10801 University Boulevard, Manassas, VA 20110-2209, on Oct. 8, 2015, and given ATCC Accession No. PTA-122644 and ATCC Accession No. PTA-122645, respectively.

EXAMPLE 2

Sandwich Capture Assay of Anti-Bed Bug Monoclonal Antibodies

A sandwich capture assay was performed using the BB2 or BB7 antibody as a capture antibody and either gold-conjugated BB2 or gold-conjugated BB7 as a detector antibody. Bed bug paper extract as described in Example 1 was used as the source of bed bug antigen. A rabbit polyclonal anti-bed bug antibody as described in U.S. Publication No. 2015-0064727 was used as a positive control capture antibody and PBS was used as a negative control for the antigen.

Figure 15:
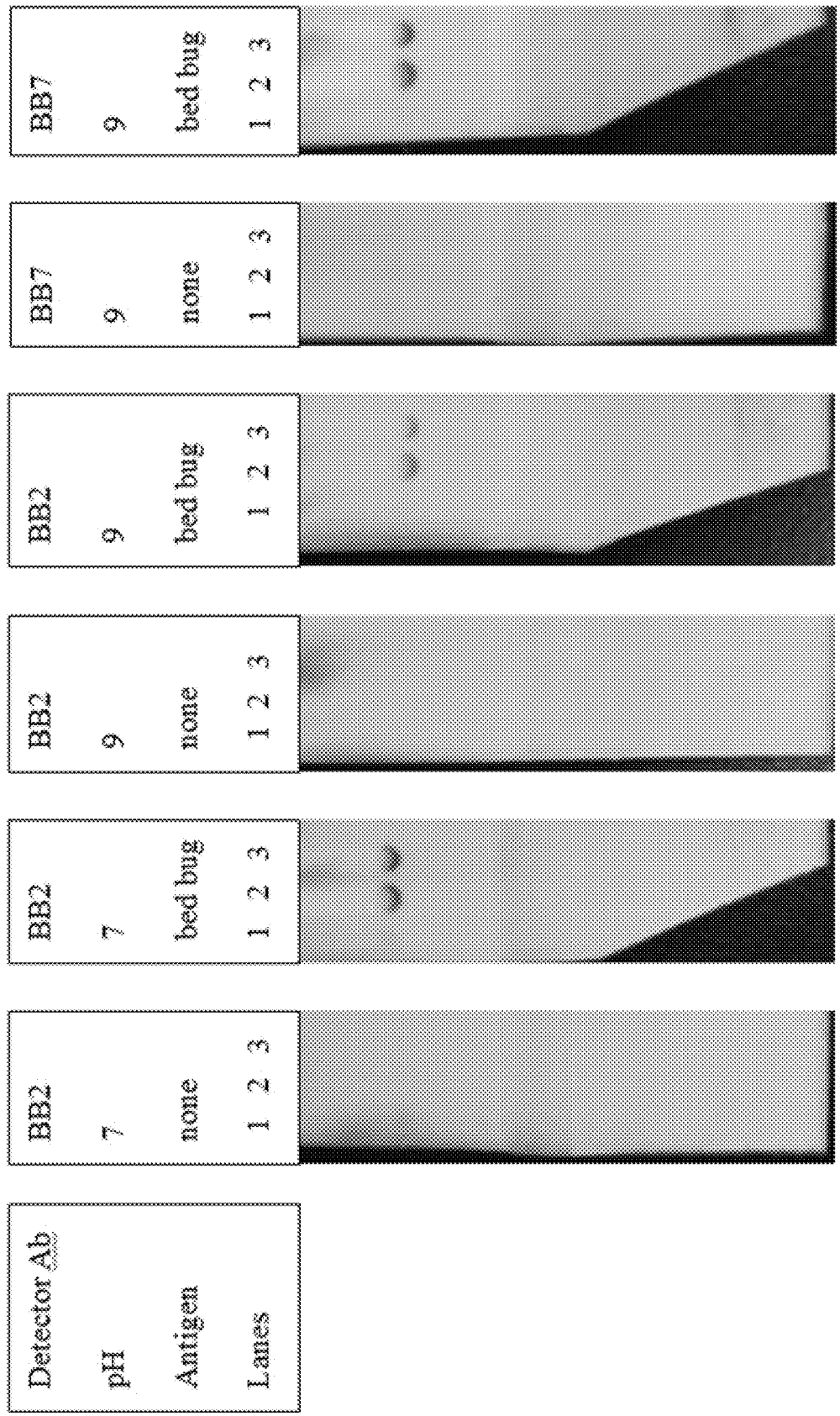
FIG. 15 shows the results of a sandwich capture assay using the BB2 and BB7 anti-bed bug monoclonal antibodies. Nitrocellulose strips are shown with binding of bed bug antigen indicated by dots associated with the presence of gold-conjugated BB2 or BB7 monoclonal antibody ("Detector Ab"), with the pH of the gold-conjugated antibody as indicated. Test strips are indicated by "bed bug" for the antigen. Negative control strips are indicated by "none" for the antigen, with PBS added to the strips instead of bed bug antigen. The capture antibodies associated with lanes 1-3 were rabbit polyclonal anti-bed bug antibody (lane 1), the BB2 monoclonal antibody (lane 2), and the BB7 monoclonal antibody (lane 3).

Capture antibodies at concentrations of 2.0 mg/ml were spotted as 0.3 µl dots onto nitrocellulose paper strips. Bed bug paper extract was added to test strips and PBS was added to negative control strips. Gold-conjugated BB2 antibody (at pH 7 or 9) or gold-conjugated BB7 antibody (at pH 9) was added as the detector antibody to the strips as shown in FIG. 15. The negative control strips showed an absence of binding by detector antibodies. Test strips showed red staining of the capture dots that indicated binding of the gold-conjugated detector antibodies to bed bug antigen immobilized on the nitrocellulose by the capture antibodies. As summarized in Table 1, strong reactions were observed with use of either the BB2 or BB7 antibody as the capture antibody. In contrast, very weak (i.e., "+") or uncertain (i.e., "+/−") reactions were observed with use of the rabbit polyclonal anti-bed bug antibody as the capture antibody.

TABLE 1

Observed Intensities in Sandwich Capture Assay

| Gold-conjugated detector antibody (pH) | Rabbit polyclonal anti-bed bug antibody | BB2 | BB7 |
|---|---|---|---|
| BB2 (7) | + | ++++ | +++ |
| BB2 (9) | + | +++ | ++ |
| BB7 (9) | +/− | ++++ | +++ |

EXAMPLE 3

Lateral Flow Immunoassay to Detect Bed Bug Antigens

An example lateral flow immunoassay was designed to detect bed bug antigens from samples taken by swabbing areas of differing levels of bed bug infestation. Extraction buffers were prepared and tested for efficient extraction of bed bug antigen from swabs, proper flow on nitrocellulose test strips, and low to no non-specific binding. Swab samples were extracted and serially diluted to investigate the sensitivity of the assay. Precision of the assay was investigated by testing replicates and reading signal intensities using a test strip reader.

Nitrocellulose membrane preparation: Nitrocellulose membranes (CN 140, 25 mm, Sartorius Corp., Bohemia, New York, USA) were sprayed with 1.0 mg/mL of the BB7 anti-bed bug antibody as the test line and 0.5 mg/mL of goat anti-mouse antibody (Lampire Biological Laboratories, Pipersville, Pennsylvania, USA) as the control line using a Biodot Air Jet (Biodot, Irvine, California, USA) for striping the nitrocellulose membranes. Striping Buffer was 1×PBS, 0.2% Sucrose, pH 7.4. The test line and control line were sprayed 7 mm apart, with the test line located 10 mm from the bottom of the membrane. Membranes were striped at a rate of 1.0 µl/cm. The membranes were dried at 37° C. for 1 hour and stored in a desiccated foil pouch. Striped membranes were kept desiccated overnight before blocking.

Nitrocellulose membrane blocking: After drying overnight, striped membranes were placed into a blocking solution (25 mM $KPO_4$, 0.2% Casein, 0.5% Boric Acid, 0.02% Sucrose, 0.1% Surfactant 10G, 0.5% PVA) with the orientation of the test line at the bottom of the nitrocellulose and the control line on the top of the nitrocellulose. The blocking solution was allowed to wick to the top of the membrane. The membranes were removed from the blocking solution and placed in a finger rack to dry at 37° C. for 1 hour. Blocked membranes were kept desiccated in a plastic bag and stored in a dry room.

Antibody gold conjugation: A Slide-A-Lyzer™ disalysis cassette (10000 molecular weight cutoff, Thermo Fisher Scientific Inc., Carlsbad, California, USA) was used to dialyze the BB2 anti-bed bug antibody overnight in 10 mM $KPO_4$, pH 7.4. The final concentration of the BB2 antibody after dialyzing was 0.875 mg/ml. A colloidal gold solution containing 40 nm particles and an optical density (OD) of 2.28 at 525 nm was adjusted at room temperature to pH 8.6 with freshly made 0.1 M $K_2CO_3$. The dialyzed BB2 antibody was added to the colloidal gold solution while vortexing. The solution was incubated for 30 minutes on a rotator at room temperature. The conjugate was blocked with 10 µl (for every 1 ml of OD 2 colloidal gold) of gold conjugate blocking buffer (25 mM KP04, 0.2% Bioterge, 6% BSA, 0.3% Sucrose) on a rotator at room temperature for 10 minutes. The gold conjugate was centrifuged at 12000 RPM, 4° C. for 20 minutes and the supernatant was discarded. The conjugate pellet was re-suspended with 0.2 ml (for every 1 ml of OD 2 colloidal gold) re-suspension buffer (1:5 dilution of gold conjugate blocking buffer in 25 mM $KPO_4$, 0.05% Sodium Azide). The OD of the gold conjugated BB2 antibody was checked using a spectrophotometer and adjusted to 10. The gold conjugated BB2 antibody was stored at 4° C.

Gold conjugate pad preparation: A P-1000 pipette was used to saturate 300 mm Ahlstrom 8950 glass fiber conjugate pads (Ahlstrom, Helsinki, Finland) with blocking buffer (25 mM $KPO_4$, 0.2% Casein, 0.5% Boric Acid, 0.02% Sucrose, 0.1% Surfactant 10G, 0.5% PVA). After 15 minutes, the saturated conjugate pads were transferred to a paper towel for a minute. Then, the conjugate pads were placed on a finger rack to dry at 37° C. for 1 hour. Blocked conjugate pads were put in a plastic bag with desiccators and stored in a dry room. The OD10 gold-conjugated BB2 antibody was prepared by adding 10% Sucrose and 5% Trehalose to the conjugate. The gold-conjugated antibody was dispensed onto the conjugate pads by an automatic striper (Matrix 160, Kinematic Automation, Inc., Twain Harte, California, USA)

at a dispensing rate of 10 µl/cm. The conjugate pads were dried at 37° C. for 1 hour, packed in a desiccated foil pouch, and stored in a dry room.

Test strip lamination and cutting: The nitrocellulose membrane striped with the test BB7 antibody and control goat anti-mouse antibody was laminated onto a vinyl backing card (G&L Precision Die Cutting, San Jose, California, USA). A wick pad (30250, EMI Specialty Papers, Redding, Connecticut, USA) was placed on the top portion of the backing, overlapping the membrane by 2 mm. A 10 mm conjugate pad was overlapped onto the membrane by 2 mm. A sample pad (Surewick C048 cellulose pad, Millipore, Darmstadt, Germany) was placed on top of the conjugate pad with a 15 mm overlap from the bottom of the backing card. Assembled cards were cut into 4 mm strips using a cutter (CM4000, Biodot, Irvine, California, USA).

Extraction of test swabs: Swab samples were obtained from test sites having different levels of bed bug infestations, designated as levels of 0, 2, 3, 4, 5, 7, and 8, with level 0 having the lowest level (i.e., no bed bugs) and 8 the highest level. Swabs were extracted in 350 µl of extraction buffer for 15 minutes at room temperature in an Eppendorf tube. Three extraction buffers were tested: extraction buffer 1 contained 1× Tris-HCl (pH 7.6), 0.05% NaN$_3$, 0.1% BSA, and 0.1% Tween-20; extraction buffer 2 contained 1× Tris-HCl (pH 7.6), 0.05% NaN$_3$, 0.1% BSA, and 0.2% Tween-20; and extraction buffer 3 contained 1× Tris-HCl (pH 7.6), 0.05% NaN$_3$, 0.25% BSA, and 0.1% Tween-20. Serial dilutions of the swab extracts were performed from 1/2 to 1/4096.

Assay testing method: 70 µl of extraction buffer (negative control) or bed bug swab sample in extraction buffer was pipeted onto the sample pad. The test line intensity was read at 15 minutes by eye.

Figure 16:
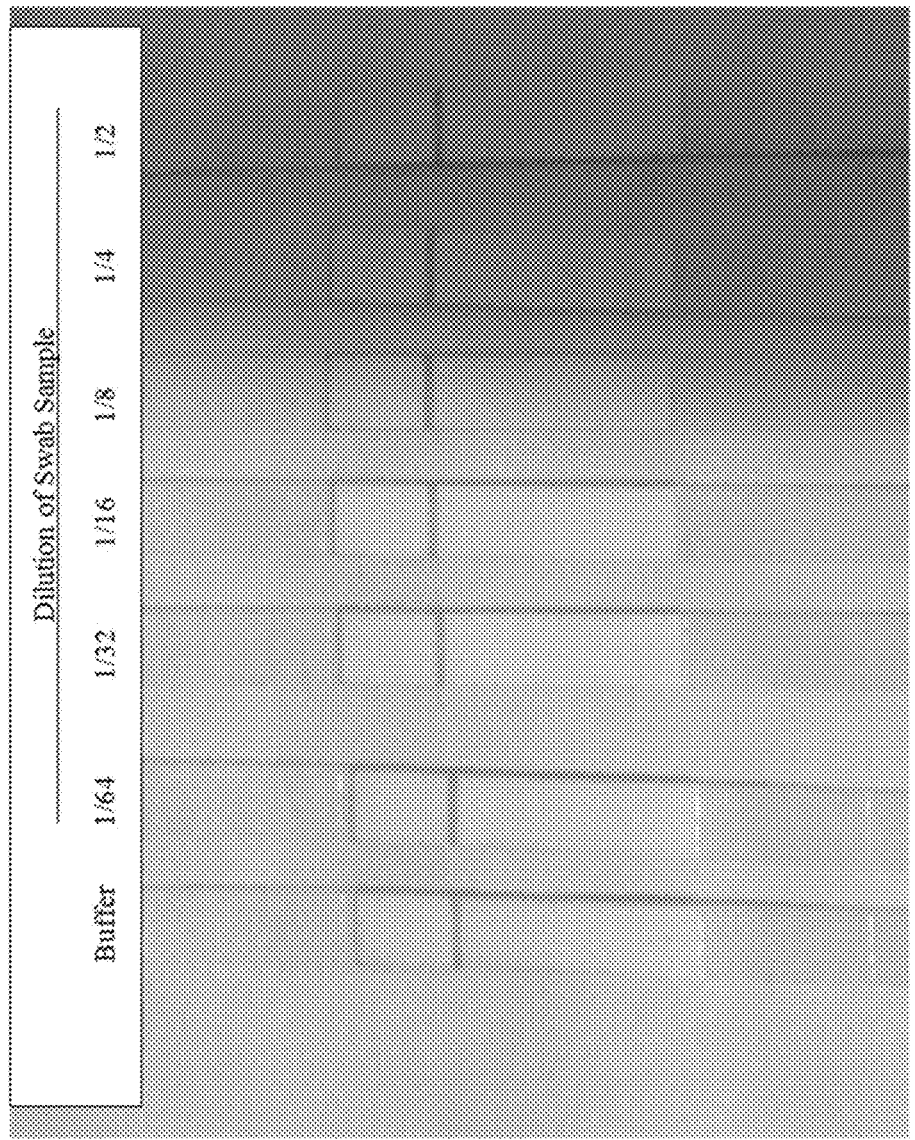
FIGS. 16-21 show the results of a lateral flow immunoassay for swab samples obtained from the noted levels of bed bug infestation, with level 0 containing no bed bugs and level 8 containing the highest level of bed bugs. Swab samples were extracted in extraction buffer 1 containing 1× Tris-HCl (pH 7.6), 0.05% $NaN_3$, 0.1% BSA, and 0.1% Tween-20 and the noted dilutions were applied to test strips. "Buffer" indicates a negative control test strip in which buffer 1 was applied instead of a swab sample. All of the strips contain a positive control stripe of goat anti-mouse antibody, which is located above a BB7 capture antibody stripe for binding bed bug antigen. The stripes become visually detectable only upon binding of the gold-conjugated mouse monoclonal BB2 antibody to the goat anti-mouse positive control stripe or to immobilized bed bug antigen captured by the BB7 stripe. The line on the "Buffer" strip and the corresponding lines on the test strips are the positive controls that indicate binding of the goat anti-mouse antibody to the gold-conjugated BB2 detector antibody. Only positive controls are detectable in FIG. 16 due to the absence of antigen. The lines beneath the positive control lines in FIGS. 17-21 indicate binding of the gold-conjugated BB2 antibody to immobilized bed bug antigen captured by the BB7 stripe.
Figure 17:
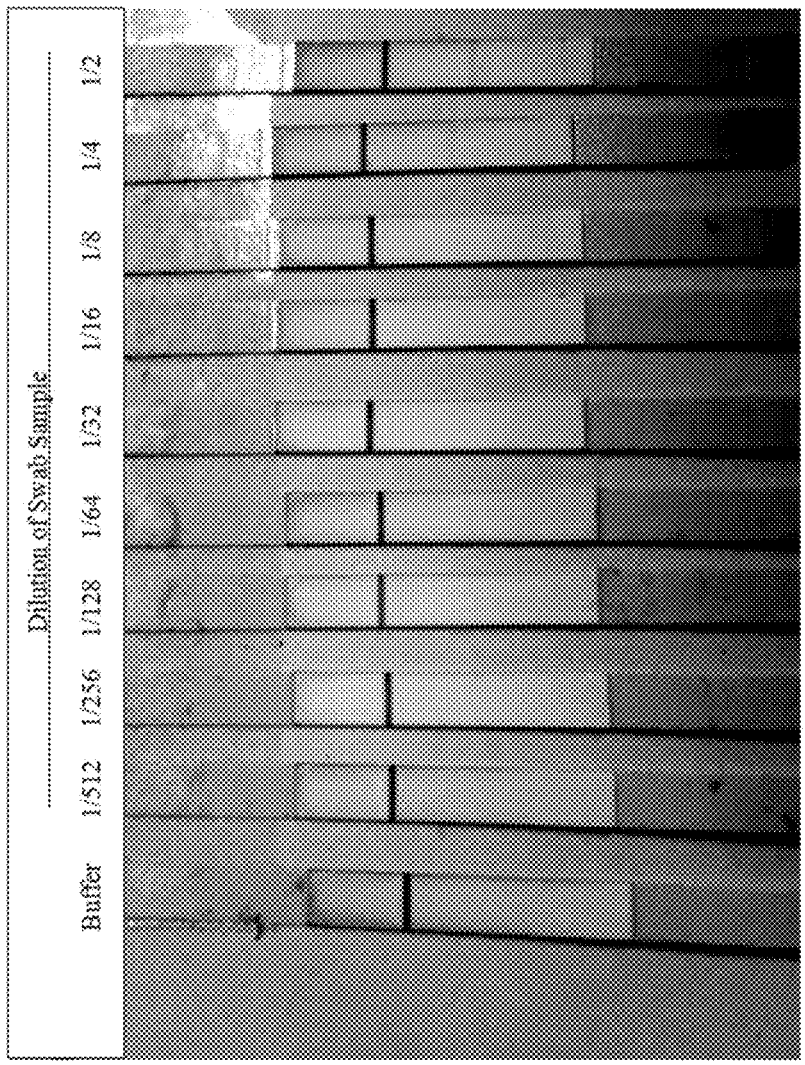
Figure 18:
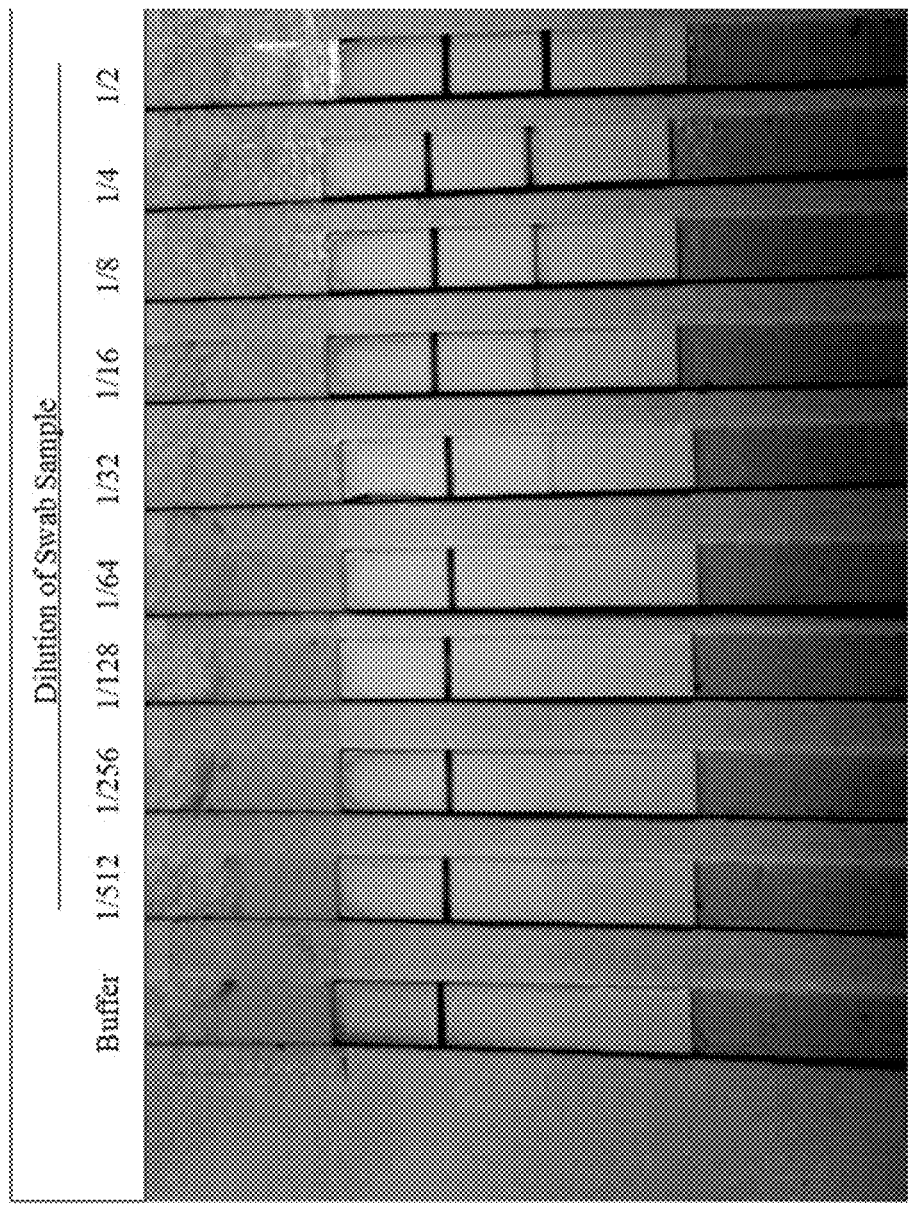
Figure 19:
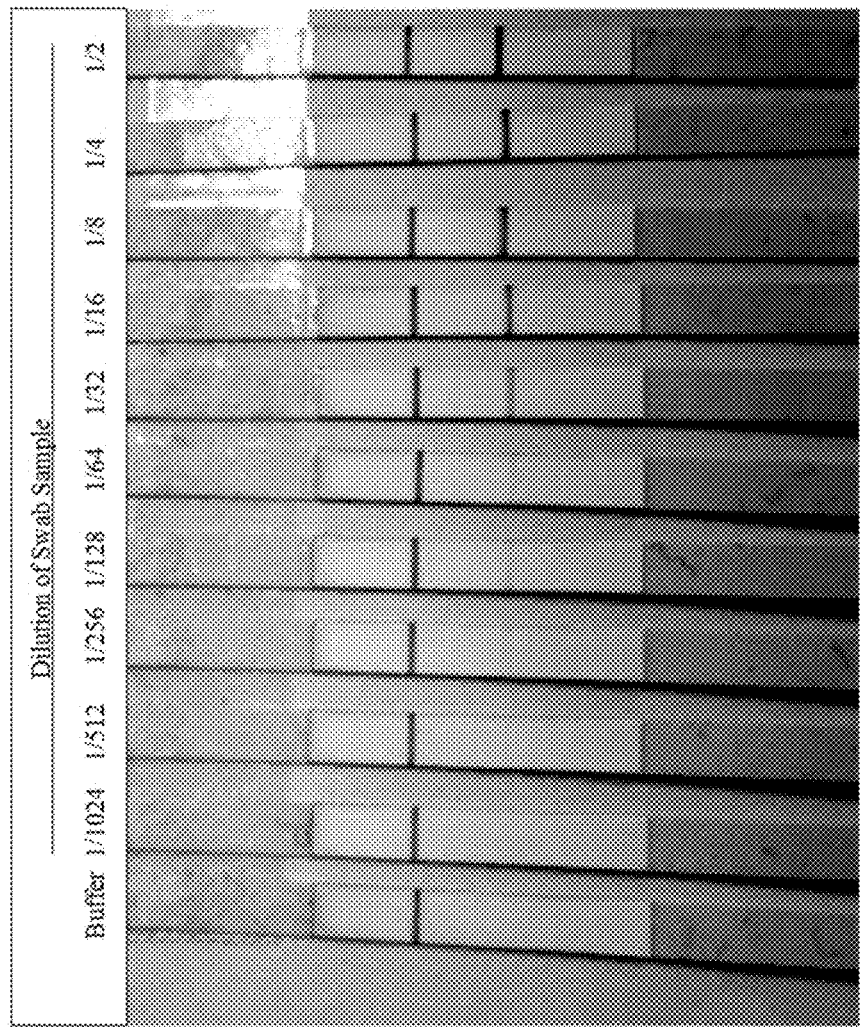
Figure 20:
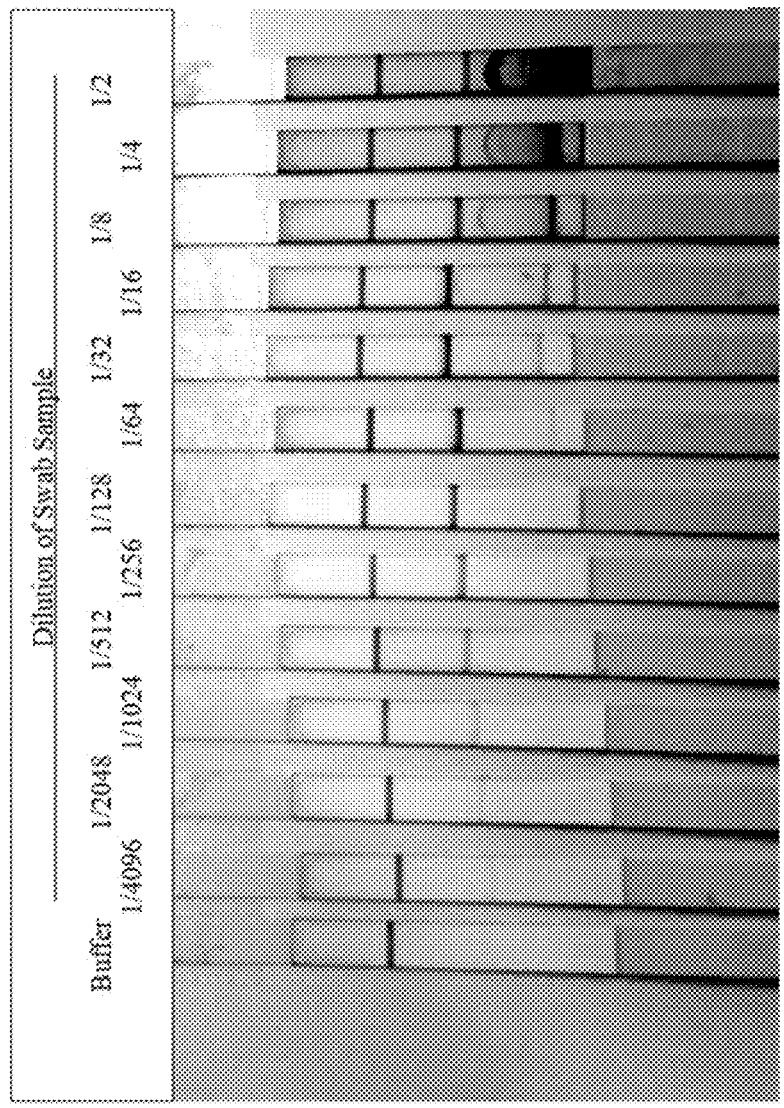
Figure 21:
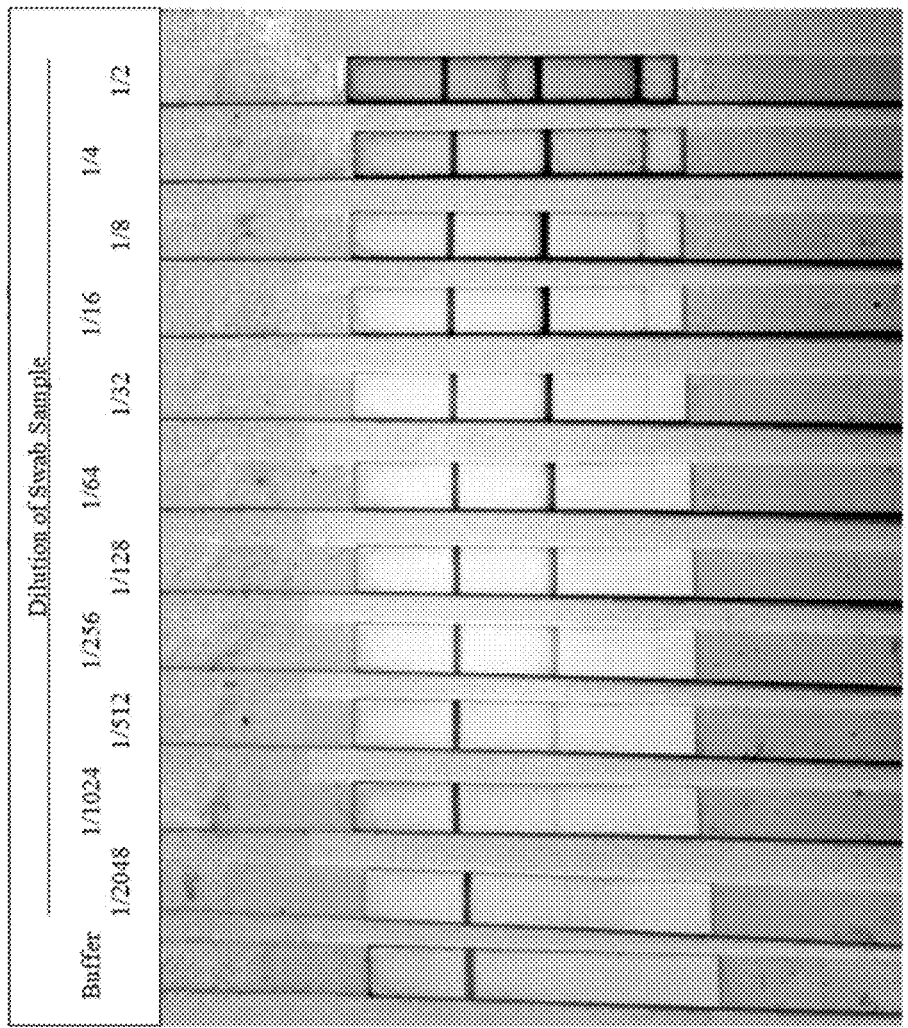

Extraction buffer 1 results: As shown in FIGS. 16-21, all strips showed positive control lines for the binding of the goat anti-mouse antibody to the gold-conjugated BB2 antibody. All strips showed the absence of test lines for the negative control strip in which extraction buffer was added instead of a swab sample. FIG. 16 only shows positive control lines for the level 0 swab sample dilutions since bed bug antigen was not present. In FIGS. 17-21, the positive control lines are the top lines, and any test lines showing the presence of bed bug antigen are beneath the positive control lines. Dirt or insoluble particles from the swabs were present near the bottom of the membranes for level 3, 5, 7, and 8 test strips. The level 2 swab sample (FIG. 17) had visible test lines from the 1/16 dilution to the 1/2 dilution. The level 3 swab sample (FIG. 18) had visible test lines from the 1/128 dilution to the 1/2 dilution. The level 4 swab sample (FIG. 19) had visible test lines from the 1/1024 dilution to the 1/2 dilution. The level 7 swab sample (FIG. 20) had visible test lines from the 1/4096 dilution to the 1/2 dilution. The level 8 swab sample (FIG. 21) had visible test lines from the 1/2048 dilution to the 1/2 dilution. Although visually observed, some of the noted test lines are not readily apparent for certain dilutions in FIGS. 17-21 due to photographic limitations. All test lines were without smears. The signal intensity of the 1/2 dilution from the level 2 swab was approximately equal to that of the 1/32 dilution from the level 3 swab, the 1/64 dilution from the level 4 swab, the 1/1024 dilution from the level 7 swab, and the 1/512 dilution from the level 8 swab. Therefore, visible signal intensity of the 1/2 dilution from the level 2 swab was weakest, compared to that of the 1/2 dilutions from the level 3, 4, 7 and 8 swabs. The signal of the 1/2 dilution from the level 8 swab was the strongest.

Signal intensities were also determined using an Axxin test strip reader (Axxin, Fairfield, Victoria, Australia) to measure the test line areas for different concentrations (1/2048 to 1/2) of level 0, 2, 3, 4, 7, and 8 swab samples extracted in 350 µl of buffer 1. The results are shown in Table 2.

TABLE 2

Test Line Areas from Different Concentrations of Swab Samples (Buffer 1)

| Concentration | Test Line Areas | | | | | |
| --- | --- | --- | --- | --- | --- | --- |
| | Level 8 | Level 7 | Level 4 | Level 3 | Level 2 | Level 0 |
| 0 | 253 | 397 | 232 | 267 | 237 | 362 |
| 1/2048 | 654 | 1187 | — | — | — | — |
| 1/1024 | 1013 | 1978 | 359 | — | — | — |
| 1/512 | 1936 | 3291 | 443 | 336 | 297 | — |
| 1/256 | 3388 | 5356 | 681 | 526 | 284 | — |
| 1/128 | 5373 | 7348 | 990 | 526 | 285 | — |
| 1/64 | 7662 | 10522 | 840 | 743 | 326 | 327 |
| 1/32 | 9341 | 11385 | 3024 | 1199 | 310 | 296 |
| 1/16 | 11420 | 12550 | 4609 | 2095 | 411 | 265 |
| 1/8 | 12066 | 8830 | 7500 | 3309 | 392 | 433 |
| 1/4 | 9793 | 7765 | 7980 | 6161 | 574 | 316 |
| 1/2 | 8693 | 6279 | 8550 | 8516 | 967 | 448 |

For each level, a reading was obtained for buffer as a negative control (i.e., concentration "0"). The negative control reading (Bo) was divided by itself to yield a normalized value of 1. The negative control reading (Bo) was then divided by the test line area (B) for each dilution in the level, where smaller values under 1 suggest larger amounts of bed bug antigen and values above 1 indicate absence of bed bug antigen. The data expressed as Bo/B is provided in Table 3.

TABLE 3

Bo/B Calculated from Test Line Areas from Different Concentrations of Swab Samples (Buffer 1)

| Concentration | Bo/B | | | | | |
| --- | --- | --- | --- | --- | --- | --- |
| | Level 8 | Level 7 | Level 4 | Level 3 | Level 2 | Level 0 |
| 0 | 1 | 1 | 1 | 1 | 1 | 1 |
| [1/2048] | 0.3869 | 0.3345 | — | — | — | — |
| [1/1024] | 0.2498 | 0.2007 | 0.6462 | — | — | — |
| [1/512] | 0.1307 | 0.1206 | 0.5237 | 0.7946 | 0.798 | — |
| [1/256] | 0.0747 | 0.0741 | 0.3407 | 0.5076 | 0.8345 | — |
| [1/128] | 0.0471 | 0.054 | 0.2343 | 0.5076 | 0.8316 | — |
| [1/64] | 0.033 | 0.0377 | 0.2762 | 0.3594 | 0.727 | 1.107 |
| [1/32] | 0.0271 | 0.0349 | 0.0767 | 0.2227 | 0.7645 | 1.223 |
| [1/16] | 0.0222 | 0.0316 | 0.0503 | 0.1274 | 0.5766 | 1.366 |
| [1/8] | 0.021 | 0.045 | 0.0309 | 0.0807 | 0.6046 | 0.836 |
| [1/4] | 0.0258 | 0.0511 | 0.0291 | 0.0433 | 0.4129 | 1.146 |
| [1/2] | 0.0291 | 0.0632 | 0.0271 | 0.0314 | 0.2451 | 0.808 |

Figure 22A:
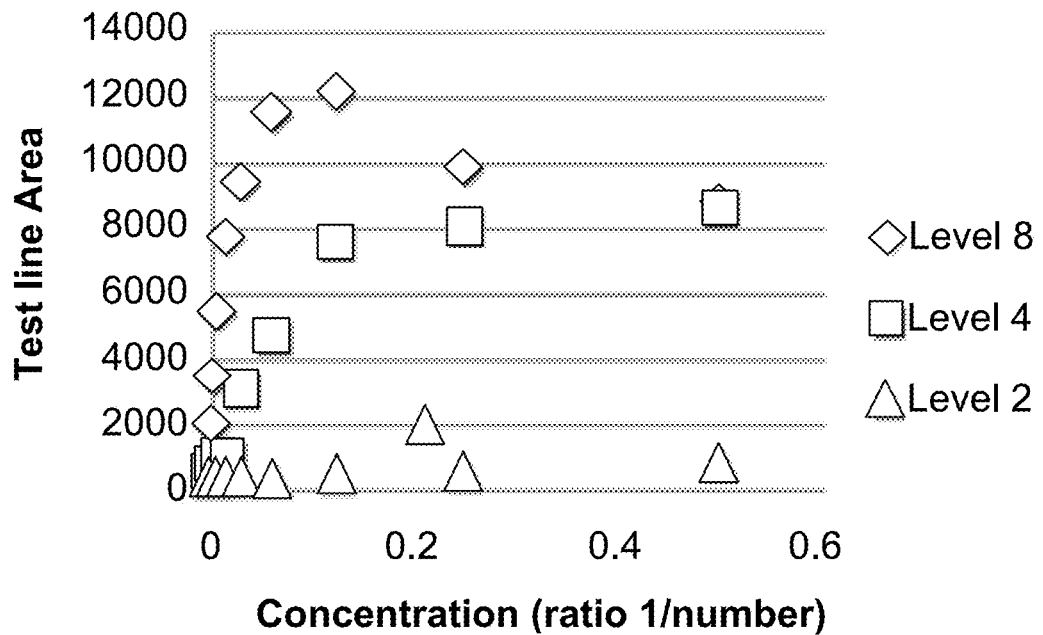
FIGS. 22A and 22B are graphs based on measurements made by the Axxin test strip reader of swab samples for levels 2, 4, and 8 extracted in buffer 1.
Figure 22B:
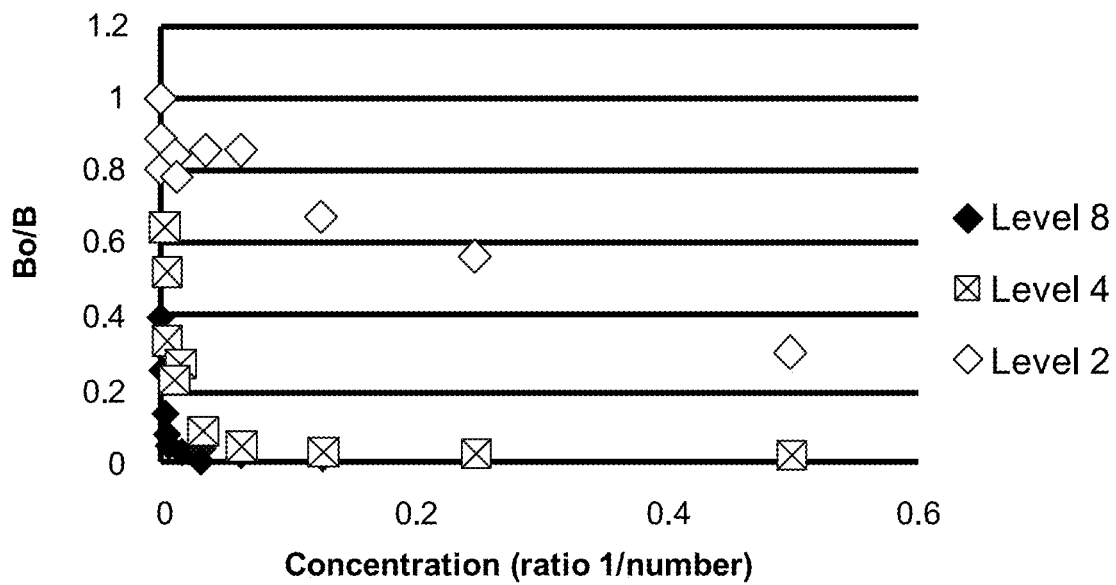

Tables 2-3 and FIG. 22A show, in general, that the measured values of concentrations from level 8 swabs (corresponding to the greatest level of bed bug infestation) were highest and values of concentrations from level 2 swabs (corresponding to the smallest level of bed bug infestation) were lowest. Table 2 and FIG. 22B show that level 8 swabs produced better signal intensities than level 2 and level 4 swabs. Table 3 suggests that level 8 swabs contained more bed bug antigen than other levels.

Figure 23:
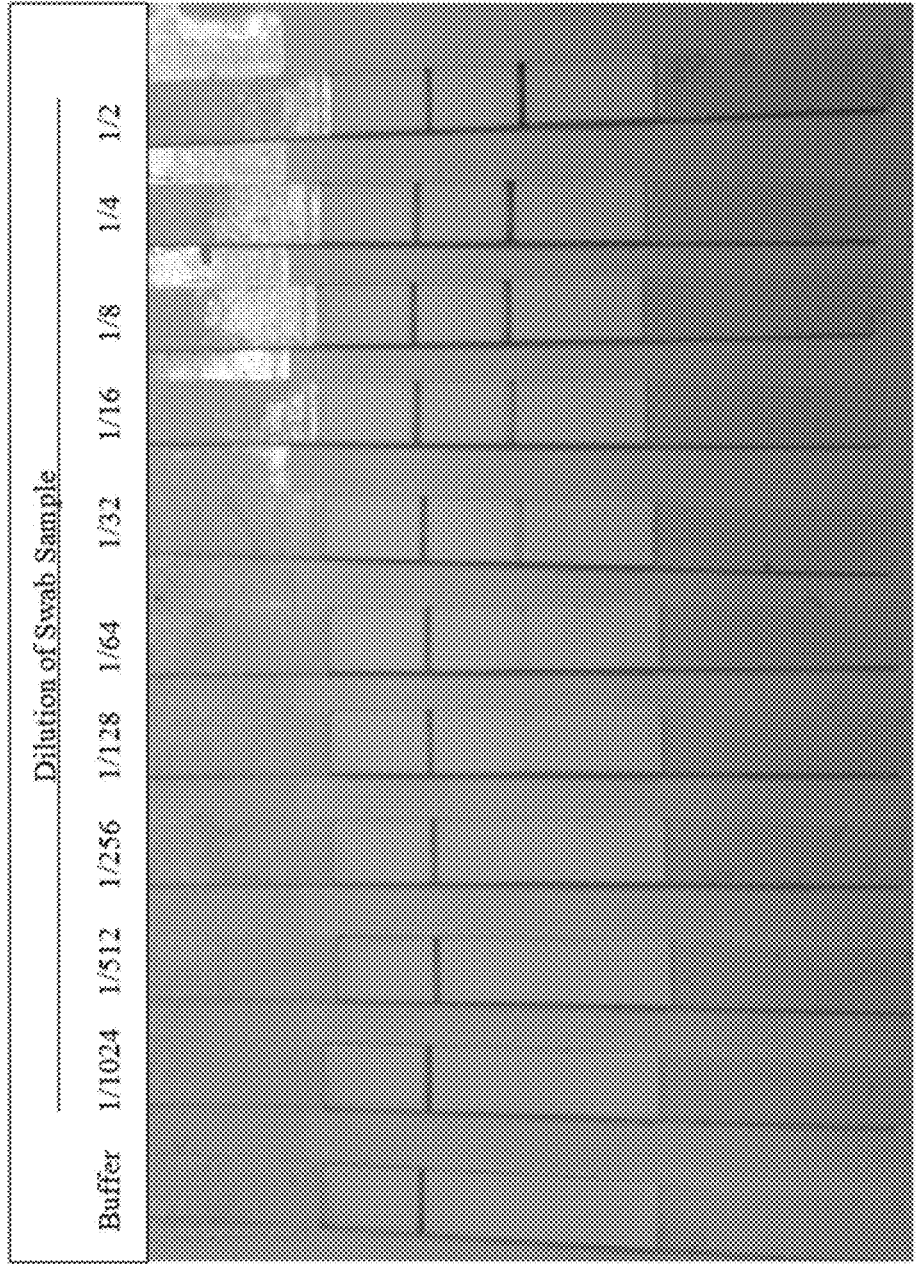
FIGS. 23-25 show the results of a lateral flow immunoassay for swab samples obtained from the noted levels of bed bug infestation. Swab samples were extracted in extraction buffer 2 containing 1× Tris-HCl (pH 7.6), 0.05% $NaN_3$, 0.1% BSA, and 0.2% Tween-20 and the noted dilutions were applied to test strips.
Figure 24:
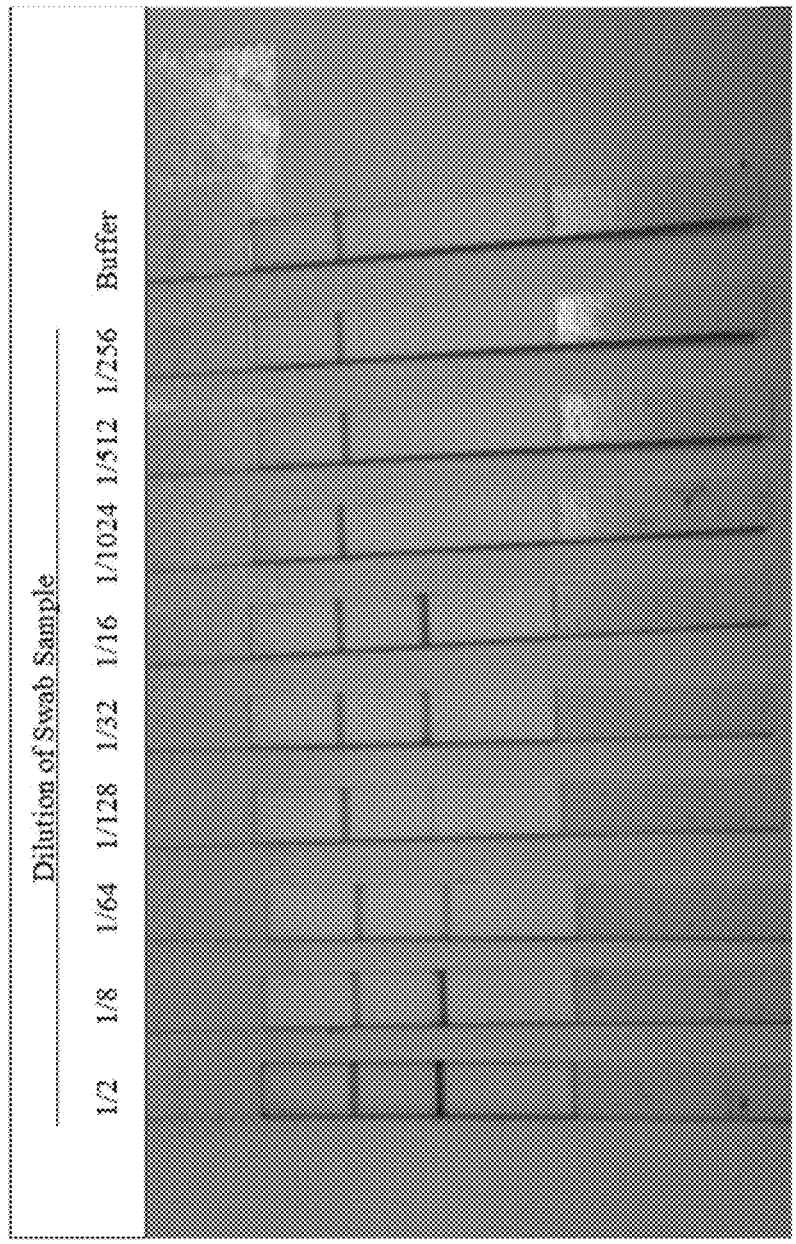
Figure 25:
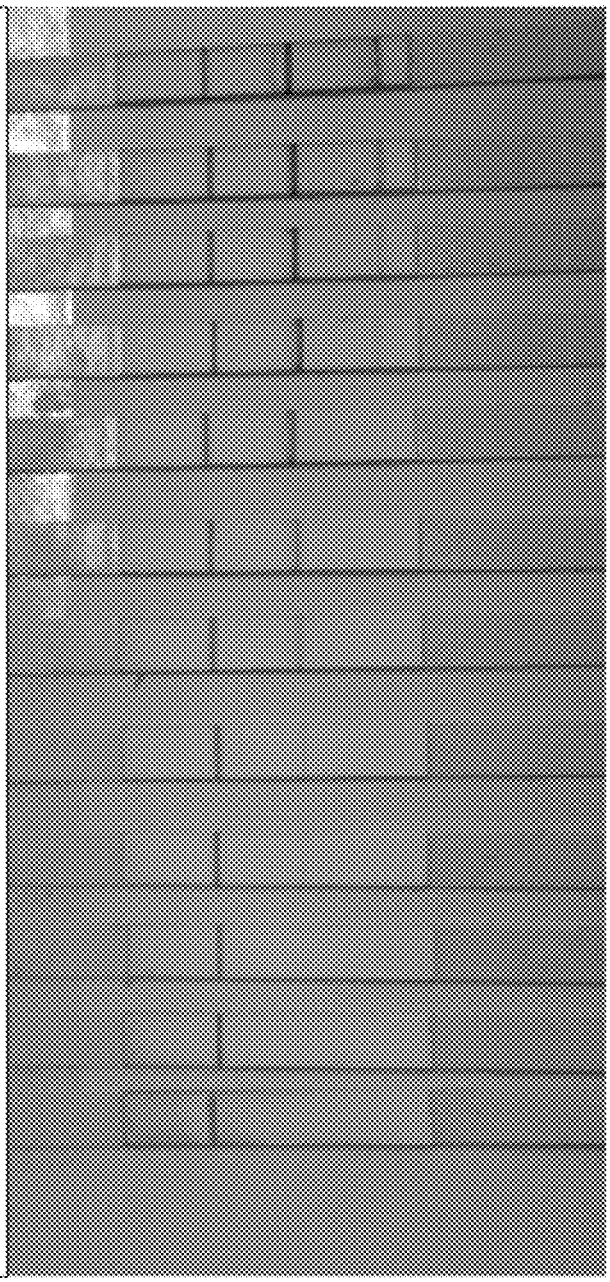

Extraction buffer 2 results: As shown in FIGS. 23-25, all strips showed positive control lines for the binding of the goat anti-mouse antibody to the gold-conjugated BB2 antibody. All strips showed the absence of test lines for the negative control strip in which extraction buffer was added instead of a swab sample. In FIGS. 23-25, the positive control lines are the top lines, and any test lines showing the presence of bed bug antigen are beneath the positive control lines. Dirt or insoluble particles from the swabs were present near the bottom of the membranes for level 4, 5, and 8 test strips. The level 4 swab sample (FIG. 23) had visible test lines from the 1/512 dilution to the 1/2 dilution. The level 5 and 8 swab samples (FIGS. 24 and 25, respectively) had visible test lines from the 1/1024 dilution to the 1/2 dilution. Although visually observed, some of the noted test lines are not readily apparent for certain dilutions in FIGS. 23-25 due to photographic limitations. All test lines were smeared. The signal intensity of the 1/16 dilution from the level 4 swab was approximately equal to that of the 1/64 dilution from the level 5 and 8 swabs. Signal intensity was weakest for the level 4 swab and similar between the level 5 and 8 swabs.

Signal intensities were also determined using an Axxin test strip reader (Axxin, Fairfield, Victoria, Australia) to measure the test line areas for different concentrations (1/2048 to 1/2) of level 4, 5, and 8 swab samples extracted in 350 µl of buffer 2. The results are shown in Table 4.

TABLE 4

Test Line Areas from Different Concentrations of Swab Samples (Buffer 2)

| | Test Line Areas | | |
|---|---|---|---|
| Concentration | Level 8 | Level 5 | Level 4 |
| 0 | 195 | 230 | 217 |
| 1/2048 | 365 | — | — |
| 1/1024 | 693 | 542 | 356 |
| 1/512 | 961 | 810 | 446 |
| 1/256 | 1787 | 1395 | 527 |
| 1/128 | 3250 | 2143 | 959 |
| 1/64 | 5225 | 4157 | 1623 |
| 1/32 | 7927 | 6696 | 2692 |
| 1/16 | 9306 | 9766 | 4413 |
| 1/8 | 10647 | 10173 | 6685 |
| 1/4 | 11489 | — | 8605 |
| 1/2 | 9818 | 12250 | 10150 |

The data expressed as Bo/B calculated from test line areas is provided in Table 5.

TABLE 5

Bo/B Calculated from Test Line Areas from Different Concentrations of Swab Samples (Buffer 2)

| | Bo/B | | |
|---|---|---|---|
| Concentration | Level 8 | Level 5 | Level 4 |
| 0 | 1 | 1 | 1 |
| [1/2048] | 0.5342 | — | — |
| [1/1024] | 0.2814 | 0.4244 | 0.6096 |
| [1/512] | 0.2029 | 0.2840 | 0.4865 |
| [1/256] | 0.1091 | 0.1649 | 0.4118 |
| [1/128] | 0.06 | 0.1073 | 0.2263 |
| [1/64] | 0.0373 | 0.0553 | 0.1337 |
| [1/32] | 0.0246 | 0.0343 | 0.0806 |
| [1/16] | 0.0210 | 0.0236 | 0.0492 |
| [1/8] | 0.0183 | 0.0226 | 0.0325 |
| [1/4] | 0.0170 | — | 0.0252 |
| [1/2] | 0.0199 | 0.0188 | 0.0214 |

Figure 26A:
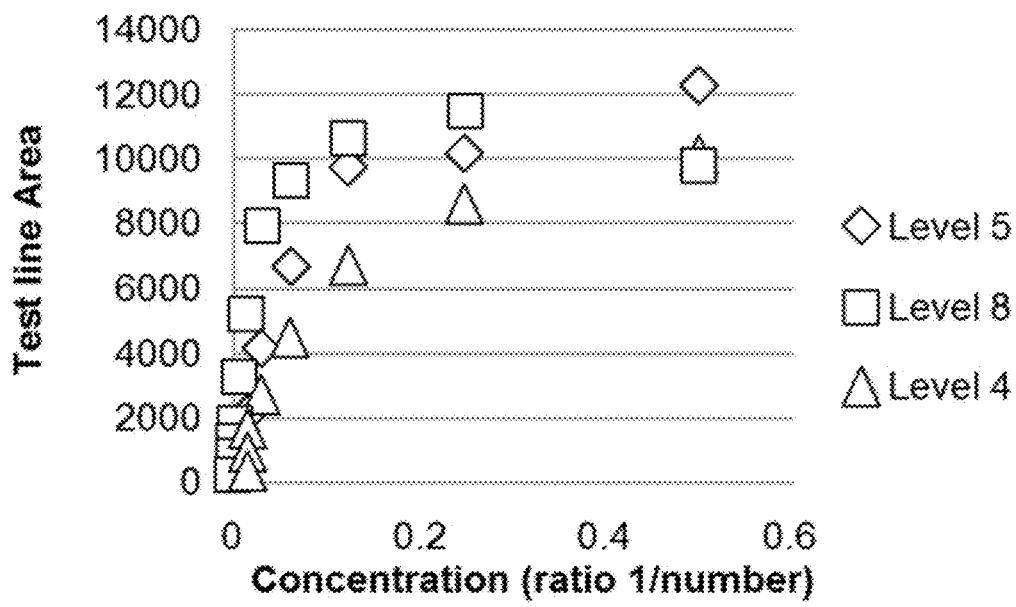
FIGS. 26A and 26B are graphs based on measurements made by the Axxin test strip reader of swab samples for levels 4, 5, and 8 extracted in buffer 2. Labeling of the graphs is as described for FIGS. 22A and 22B.
Figure 26B:
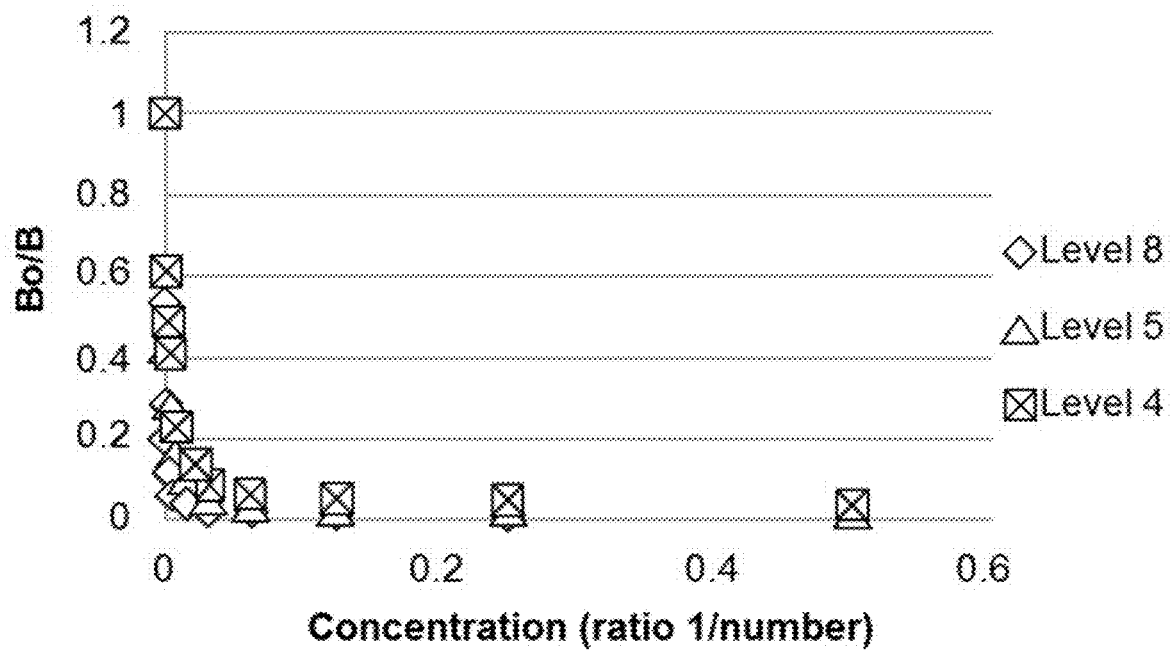
Figure 27:
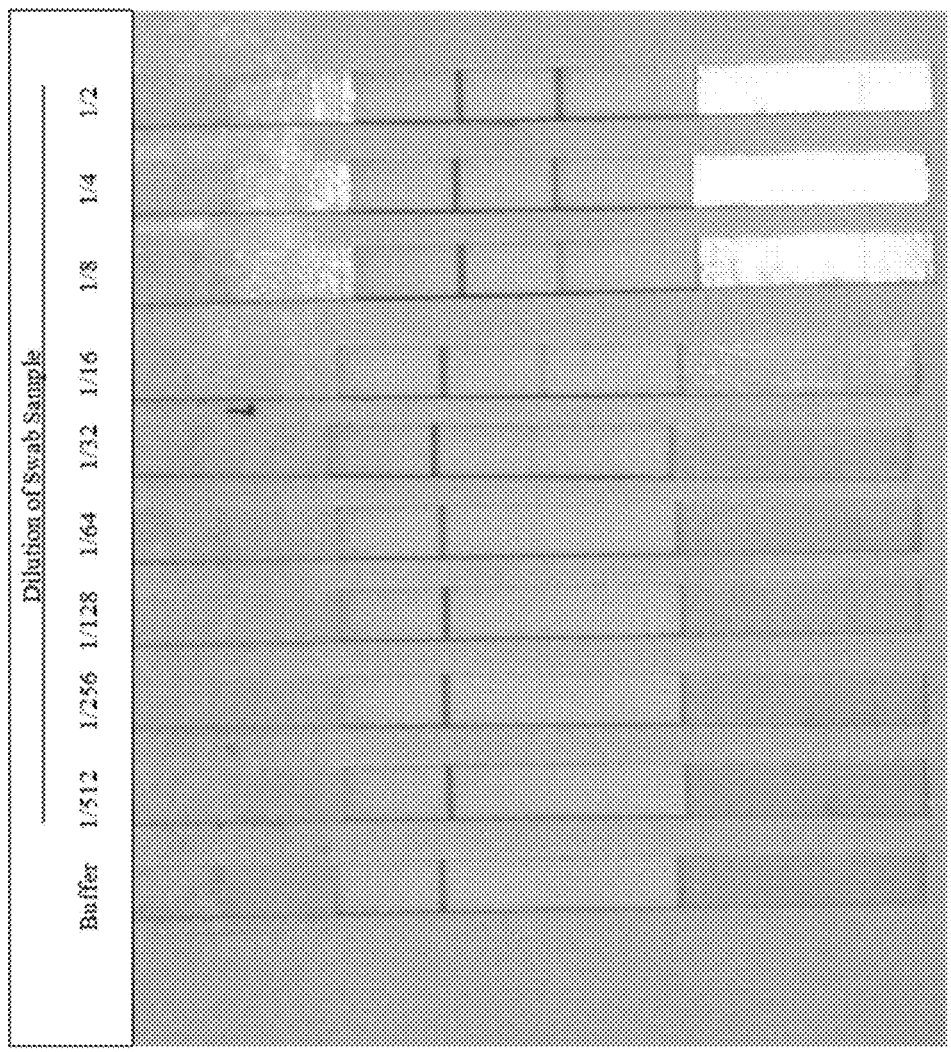
FIGS. 27-31 show the results of a lateral flow immunoassay for swab samples obtained from the noted levels of bed bug infestation. Swab samples were extracted in extraction buffer 3 containing 1× Tris-HCl (pH 7.6), 0.05% $NaN_3$, 0.25% BSA, and 0.1% Tween-20 and the noted dilutions were applied to test strips.
Figure 28:
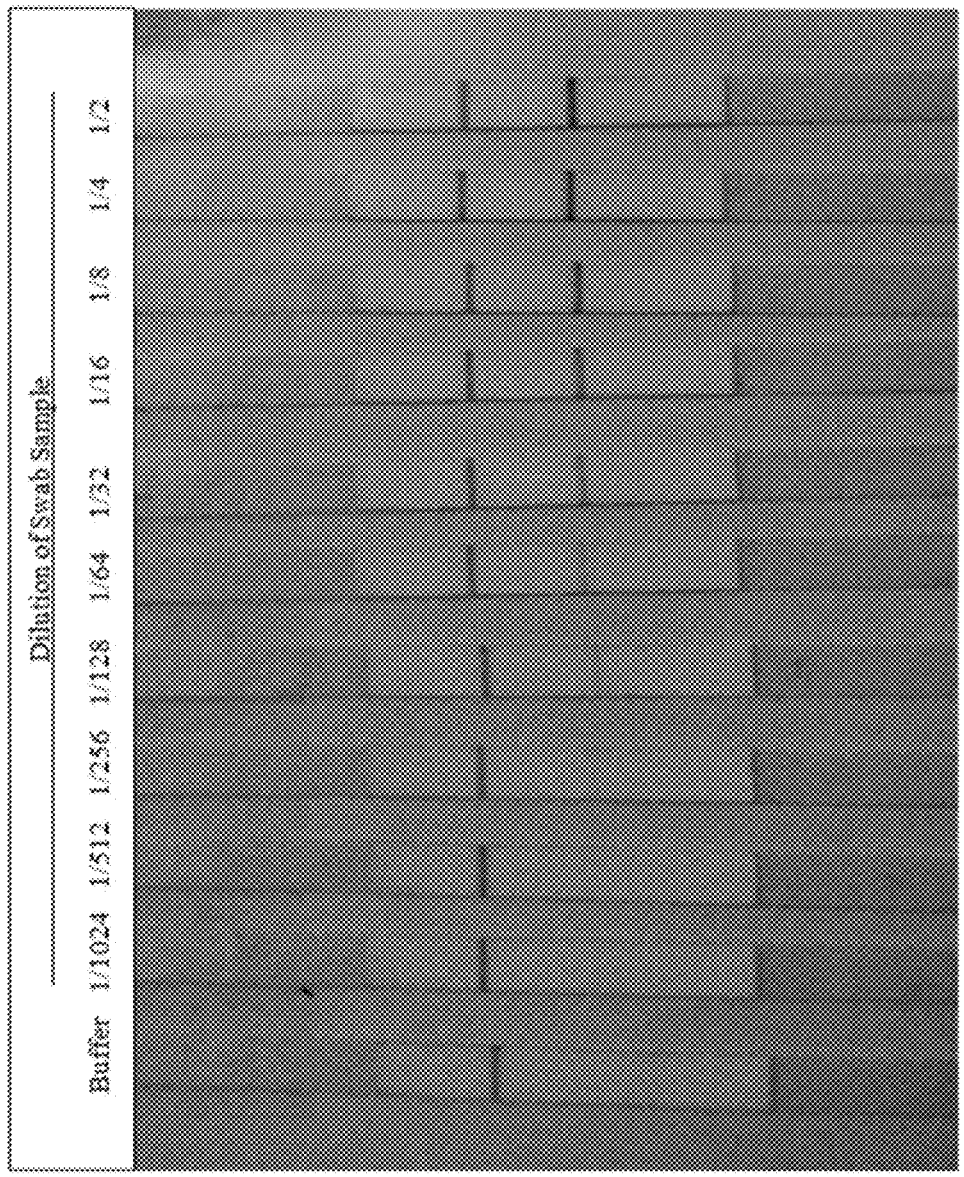
Figure 29:
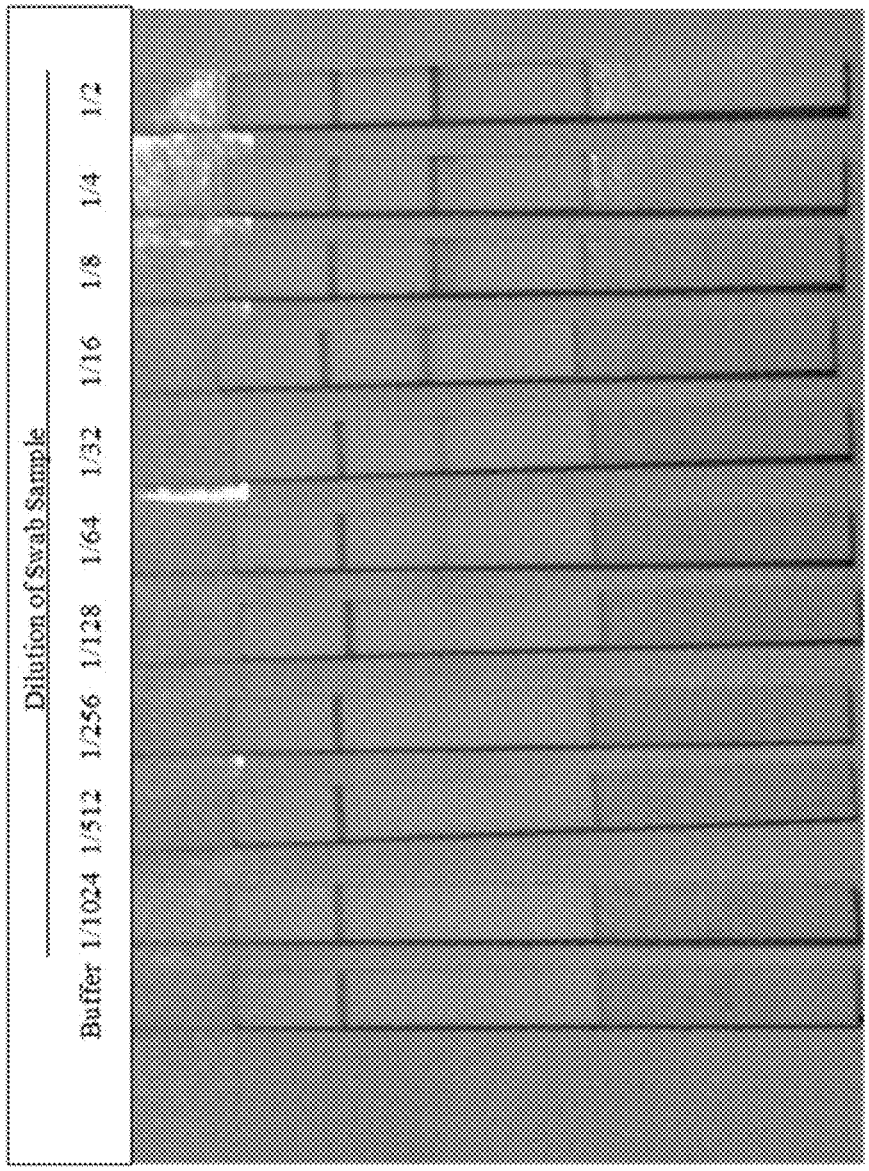
Figure 30:
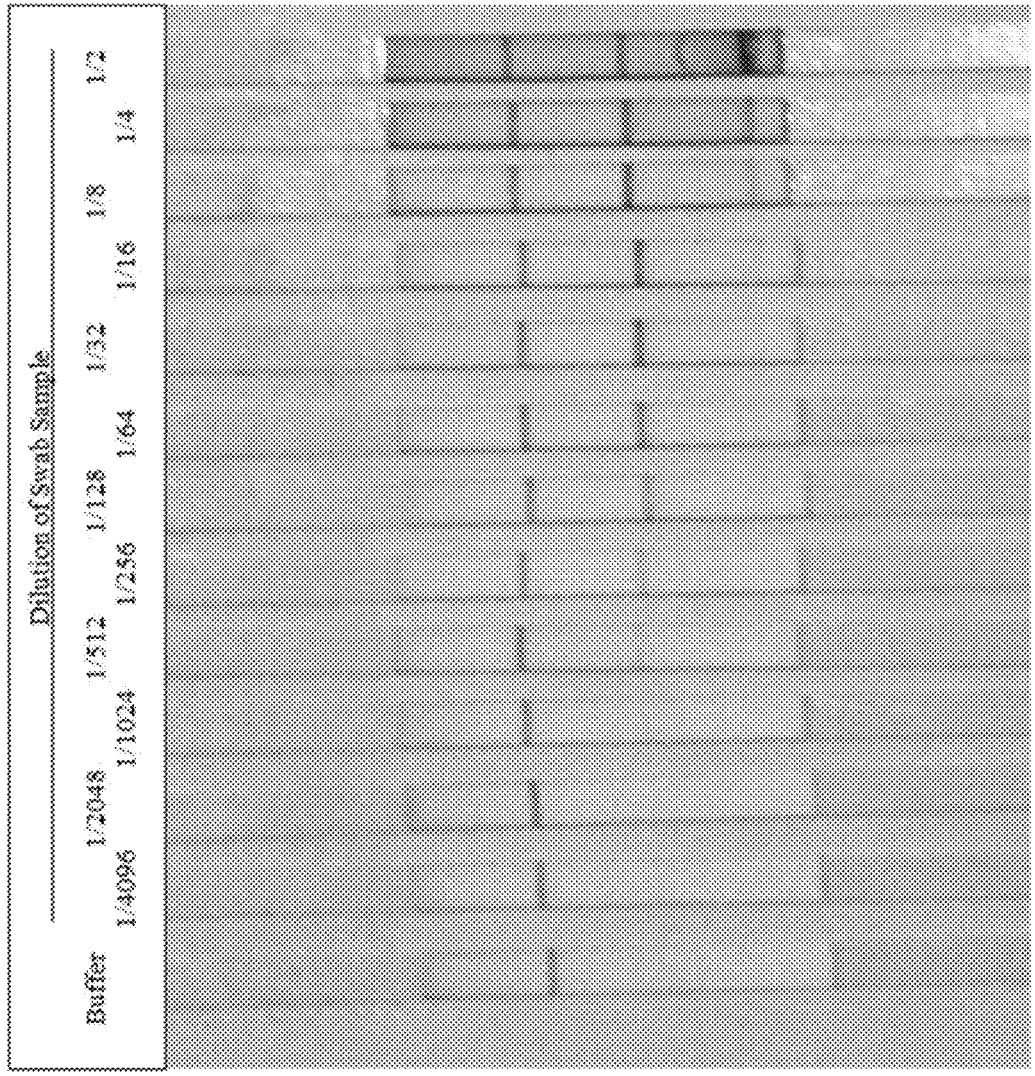
Figure 31:
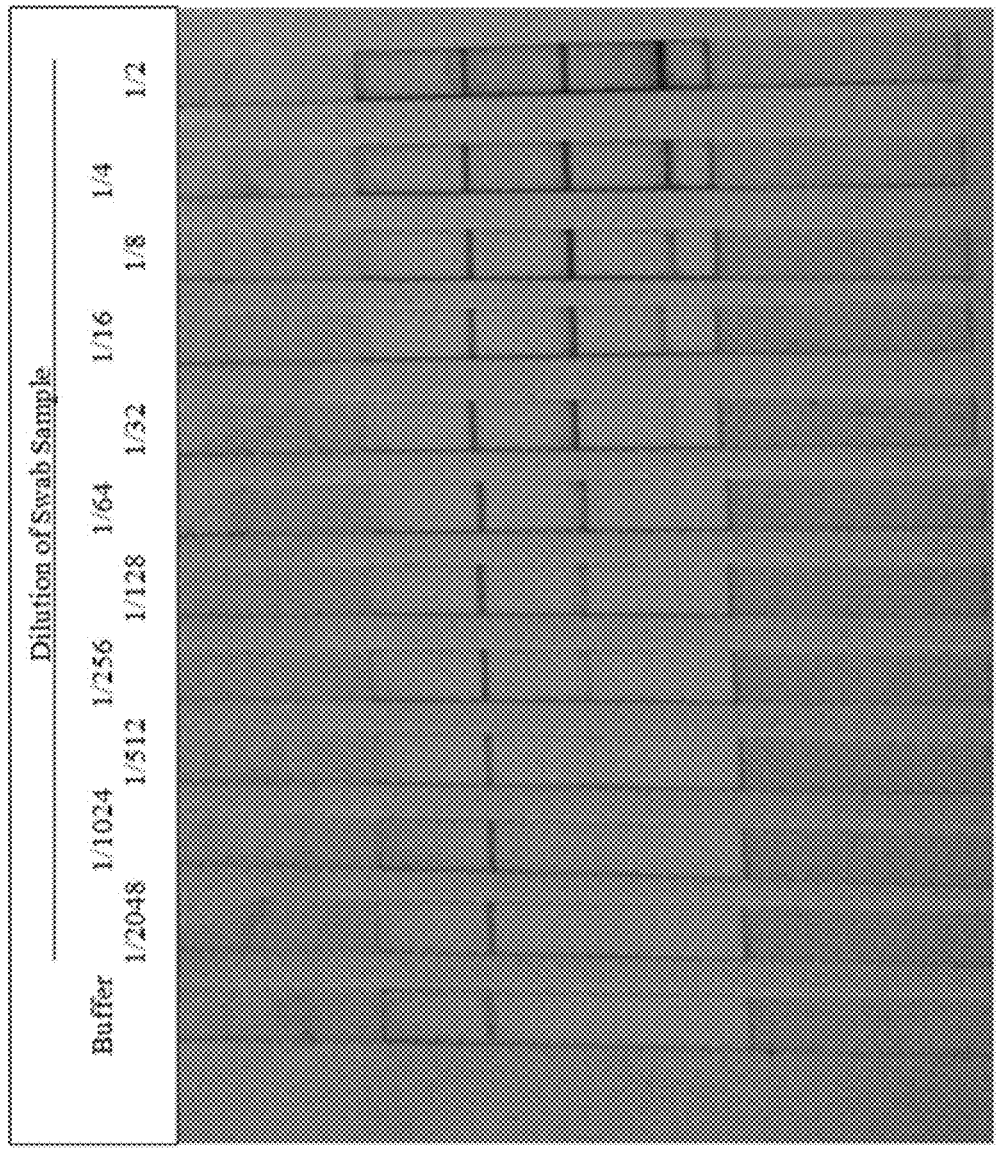

Tables 4-5 and FIG. 26A show that, in general, measured values of level 8 swabs were the highest and values of level 4 swabs were the lowest. Although visibility of test lines from level 5 swabs were similar to level 8 swabs (FIGS. 24 and 25, respectively), Axxin reader results in Table 4 and FIG. 26A show that level 8 swabs produced better signal intensities than level 4 and 5 swabs. Table 5 suggests that level 8 swabs contained more bed bug antigen than the other levels.

Extraction buffer 3 results: As shown in FIGS. 27-31, all strips showed positive control lines for the binding of the goat anti-mouse antibody to the gold-conjugated BB2 antibody. All strips showed the absence of test lines for the negative control strip in which extraction buffer was added instead of a swab sample. In FIGS. 27-31, the positive control lines are the top lines, and any test lines showing the presence of bed bug antigen are beneath the positive control lines. Dirt or insoluble particles from the swabs were present near the bottom of the membranes for level 3, 5, 7, and 8 test strips. The level 2 swab sample (not shown) had visible test lines from the 1/8 dilution to the 1/2 dilution. The level 3 swab sample (FIG. 27) had visible test lines from the 1/128 dilution to the 1/2 dilution. The level 4 swab sample (FIG. 28) had visible test lines from the 1/1024 dilution to the 1/2 dilution. The level 5 swab sample (FIG. 29) had visible test lines from the 1/512 dilution to the 1/2 dilution. The level 7 swab sample (FIG. 30) had visible test lines from the 1/4096 dilution to the 1/2 dilution. The level 8 swab sample (FIG. 31) had visible test lines from the 1/2048 dilution to the 1/2 dilution. Although visually observed, some of the noted test lines are not readily apparent for certain dilutions in FIGS. 27-31 due to photographic limitations. All test lines were smeared. The signal intensity of the 1/2 dilution from the level 2 swab was approximately equal to that of the 1/64 dilution from the level 3 swab, the 1/64 dilution from the level 4 swab, the 1/64 dilution from the level 5 swab, the 1/1024 dilution from the level 7 swab, and the 1/512 dilution from the level 8 swab. Therefore, visible signal intensity of the 1/2 dilution from the level 2 swab was weakest compared to that of the 1/2 dilutions from the other levels. The signal of the 1/2 dilution from the level 8 swab was the strongest.

Signal intensities were also determined using an Axxin test strip reader (Axxin, Fairfield, Victoria, Australia) to measure the test line areas for different concentrations (1/2048 to 1/2) of level 4, 5, and 8 swab samples extracted in 350 µl of buffer 3. The results are shown in Table 6.

TABLE 6

Test Line Areas from Different Concentrations of Swab Samples (Buffer 3)

| | Test Line Areas | | | | | |
|---|---|---|---|---|---|---|
| Concentration | Level 8 | Level 7 | Level 5 | Level 4 | Level 3 | Level 2 |
| 0 | 441 | 283 | 263 | 225 | 170 | 231 |
| 1/2048 | 735 | 781 | — | — | — | — |
| 1/1024 | 798 | 1037 | 270 | 334 | — | — |
| 1/512 | 1414 | 2003 | 385 | 574 | 309 | 261 |
| 1/256 | 2691 | 2998 | 422 | 109 | 403 | 261 |
| 1/128 | 4741 | 4665 | 1026 | 1439 | 522 | 285 |
| 1/64 | 7173 | 6912 | 2013 | 2403 | 724 | 276 |
| 1/32 | 9603 | 8746 | 5763 | 4090 | 1360 | 269 |
| 1/16 | 10377 | 9626 | 5743 | 5842 | 2430 | 271 |
| 1/8 | 11788 | 11767 | 7021 | 8061 | 3462 | 340 |
| 1/4 | 10725 | 8466 | 7120 | 9518 | 5189 | 406 |
| 1/2 | 8584 | 6803 | 9408 | 10413 | 6098 | 752 |

The data expressed as Bo/B calculated from test line areas is provided in Table 7.

TABLE 7

Bo/B Calculated from Test Line Areas from Different Concentrations of Swab Samples (Buffer 3)

| | Bo/B | | | | | |
|---|---|---|---|---|---|---|
| Concentration | Level 8 | Level 7 | Level 5 | Level 4 | Level 3 | Level 2 |
| 0 | 1 | 1 | 1 | 1 | 1 | 1 |
| [1/2048] | 0.6 | 0.3624 | — | — | — | — |
| [1/1024] | 0.5526 | 0.2729 | 0.9741 | 0.6737 | — | — |
| [1/512] | 0.3119 | 0.1413 | 0.6831 | 0.3920 | 0.5502 | 0.8851 |
| [1/256] | 0.1639 | 0.0944 | 0.6232 | 0.2064 | 0.4218 | 0.8851 |
| [1/128] | 0.0930 | 0.0607 | 0.2563 | 0.1564 | 0.3257 | 0.8105 |
| [1/64] | 0.0615 | 0.0409 | 0.1307 | 0.0936 | 0.2348 | 0.8370 |
| [1/32] | 0.0459 | 0.0324 | 0.0456 | 0.0550 | 0.1250 | 0.8587 |
| [1/16] | 0.0425 | 0.0294 | 0.0458 | 0.0385 | 0.0700 | 0.8524 |
| [1/8] | 0.0374 | 0.0241 | 0.0375 | 0.0279 | 0.0491 | 0.6794 |
| [1/4] | 0.0411 | 0.0334 | 0.0369 | 0.0236 | 0.0328 | 0.5690 |
| [1/2] | 0.0514 | 0.0416 | 0.0280 | 0.0216 | 0.0279 | 0.3072 |

Figure 32A:
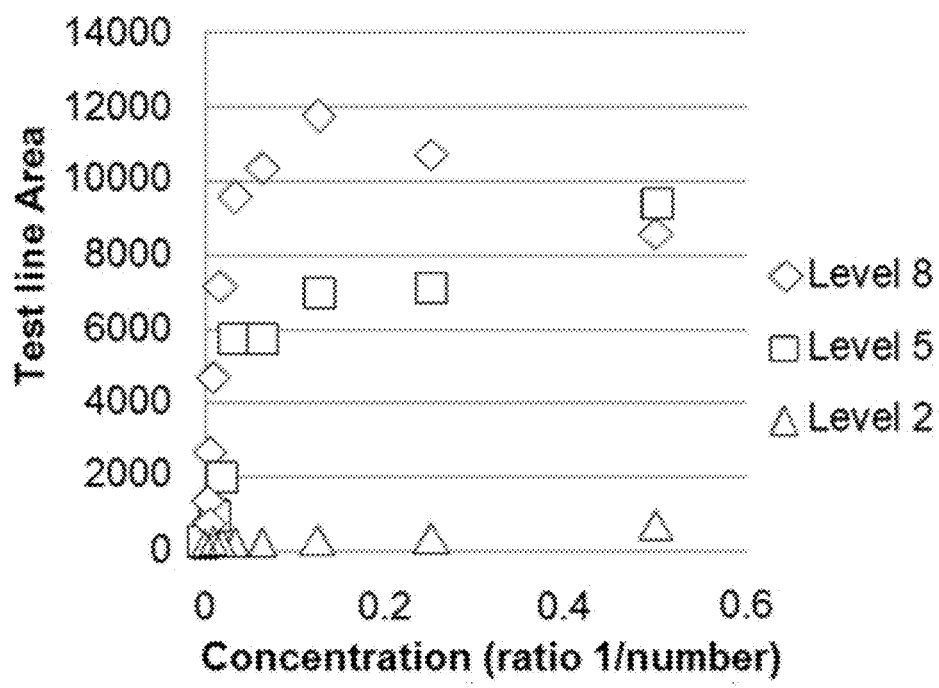
FIGS. 32A and 32B are graphs based on measurements made by the Axxin test strip reader of swab samples for levels 2, 5, and 8 extracted in buffer 3. Labeling of the graphs is as described for FIGS. 22A and 22B.
Figure 32B:
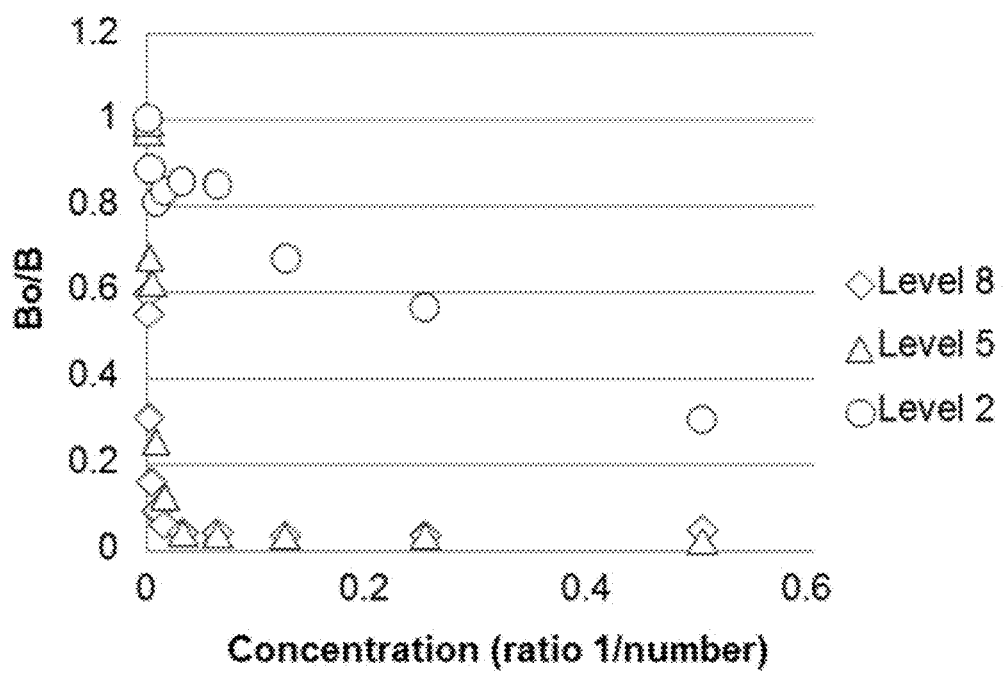
Figure 33A:
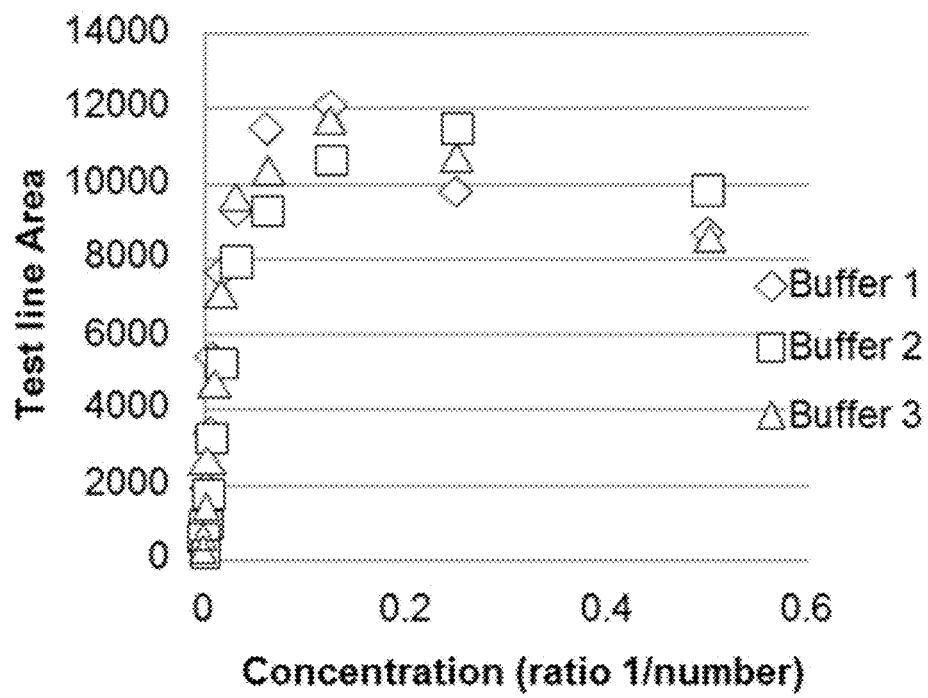
FIGS. 33A and 33B are graphs based on measurements made by the Axxin test strip reader showing a comparison of results for level 8 swab samples extracted in buffers 1, 2, and 3. Labeling of the graphs is as described for FIGS. 22A and 22B.
Figure 33B:
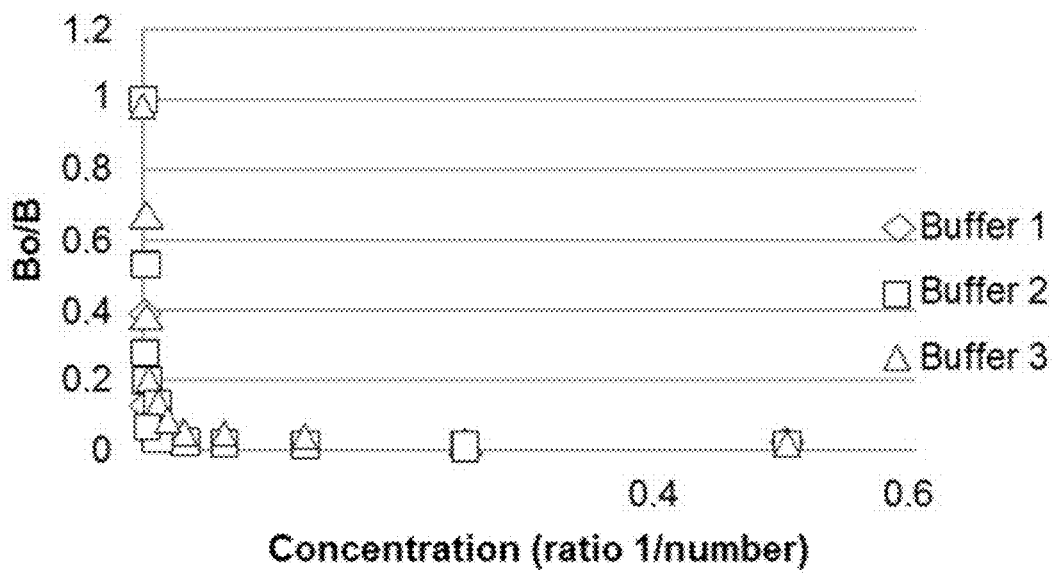

Tables 6-7 and FIG. 32A show that, in general, measured values of level 8 swabs were highest and values of level 2 swabs were lowest. Table 7 and FIG. 32A show that level 8 swabs produced better signal intensities than the other levels.

Comparison of extraction buffers: For extraction buffer 1, all test lines were clear and did not have smears, while extraction buffers 2 and 3 resulted in smeared test lines. For level 4 swabs, extraction with buffers 1 and 3 resulted in signals starting at the 1/1024 dilution, but extraction with buffer 2 resulted in signals starting at the 1/512 dilution. However, extraction of level 5 with buffer 2 yielded signal at a lower concentration (1/1024 dilution) than extraction with buffer 3 (1/512 dilution). Buffers 1 and 3 yielded signals at the same concentration for level 3 and 7 swabs. However, extraction of level 2 swabs with buffer 1 resulted in a signal at a lower concentration (1/16 dilution) than extraction with buffer 3 (1/8 dilution). In general, measured values of all test level swabs were higher for extraction with buffer 1 than for buffers 2 and 3.

Figure 34:
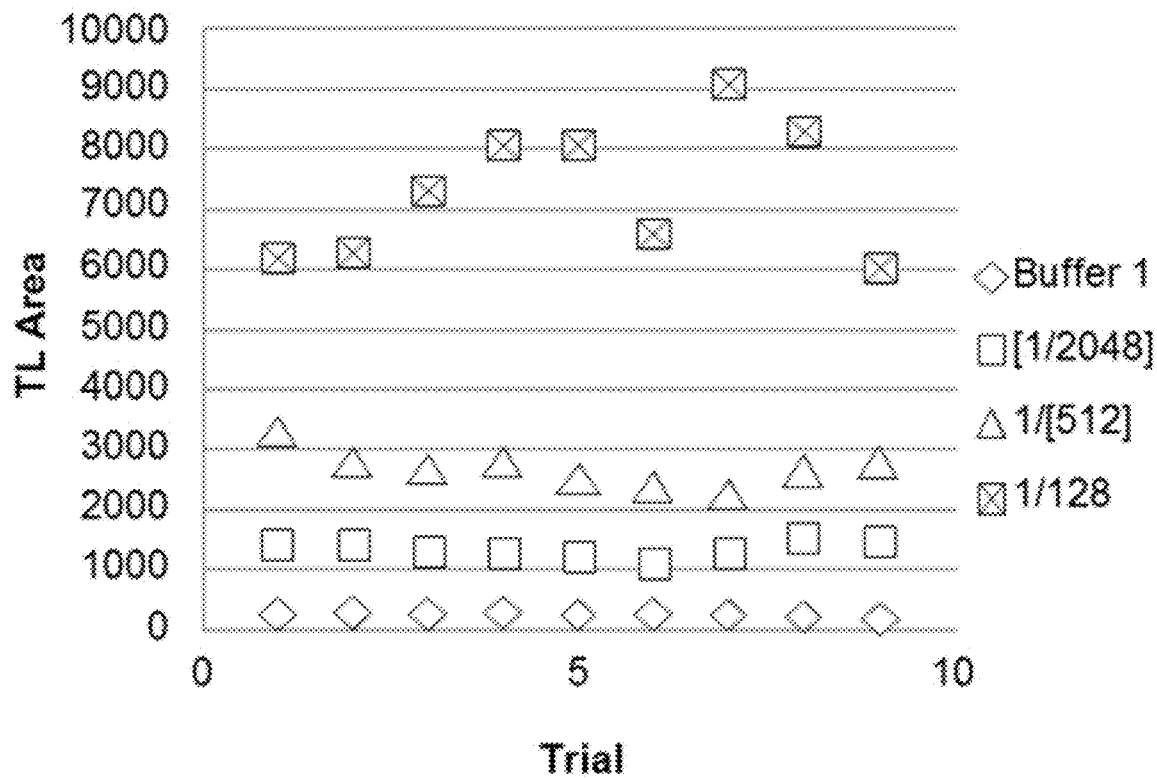
FIG. 34 is a graph based on measurements made by the Axxin test strip reader for nine replicates of extraction buffer 1 as a negative control and nine replicates each of 1/2048, 1/512, and 1/128 dilutions for level 7 swab samples extracted in buffer 1. The x-axis indicates the nine replicates by "trial" number; the y-axis is as described for FIG. 22A.

Precision study using Axxin reader: Nine replicates of extraction buffer 1 as a negative control and nine replicates each of 1/2048, 1/512, and 1/128 dilutions of level 7 swabs extracted with buffer 1 were prepared and test line areas were measured using an Axxin test strip reader (Axxin, Fairfield, Victoria, Australia). Test line areas are shown in Table 8 and FIG. 34.

TABLE 8

Precision Study Results of Replicate Test Line Areas

| | | Test Line Areas | | |
|---|---|---|---|---|
| Trial | Buffer 1 | Level 7 1/2048 | Level 7 1/512 | Level 7 1/128 |
| 1 | 250 | 1415 | 3299 | 6163 |
| 2 | 251 | 1426 | 2794 | 6276 |
| 3 | 233 | 1293 | 2684 | 7305 |
| 4 | 289 | 1238 | 2810 | 8079 |
| 5 | 260 | 1202 | 2531 | 8090 |
| 6 | 271 | 1075 | 2401 | 6583 |
| 7 | 260 | 1283 | 2260 | 9109 |
| 8 | 218 | 1540 | 2660 | 8297 |
| 9 | 194 | 1444 | 2773 | 5997 |
| Average | 247.3 | 1324.0 | 2690.2 | 7322.1 |
| STDEV | 28.6 | 144.3 | 295.3 | 1120.6 |
| % CV | 11.6 | 10.9 | 11.0 | 15.3 |

The percent coefficient of variation (% CV) was less than 20%, which is a good % CV for Axxin measurements

CONCLUSION

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

The breadth and scope of the invention should not be limited by any of the above-described exemplary embodiments, but should be defined only in accordance with the following claims and their equivalents.

What is claimed is:

1. A detection device for analyzing a test fluid to determine prior or present infestations of bed bugs, comprising a lateral flow assay test processed within the detection device, wherein the lateral flow assay test comprises a test strip for receiving the test fluid near a first end of the test strip, wherein the test strip comprises:
    (a) a reagent portion comprising a monoclonal antibody or antigen-binding fragment thereof that is conjugated to a colored particle and is capable of binding to a bed bug antigen within the test fluid to form a bed bug molecule, wherein the monoclonal antibody or antigen-binding fragment thereof comprises three heavy and three light chain complementarity determining regions of an antibody produced by a hybridoma deposited at the American Type Culture Collection (ATCC) under Accession Number PTA-122644 [BB2] or Accession Number PTA-122645 [BB7], and
    (b) a reaction portion comprising an immobilized monoclonal antibody or antigen-binding fragment thereof that is capable of binding to the bed bug molecule, wherein the monoclonal antibody or antigen-binding fragment thereof comprises three heavy and three light chain complementarity determining regions of an antibody produced by a hybridoma deposited at the ATCC under Accession Number PTA-122644 [BB2] or Accession Number PTA-122645 [BB7].

2. The detection device of claim 1, wherein the test strip comprises: (a) a backing strip comprising a wick for receiving and absorbing the test fluid, (b) a porous carrier strip comprising a reagent pad affixed to the wick, wherein the reagent pad comprises the reagent portion, (c) a line forming zone comprising the reaction portion, and (d) an absorption pad at the opposite end portion of the test strip from the wick.

3. The detection device of claim 1, wherein the monoclonal antibody or antigen-binding fragment thereof in the reagent portion and/or the reaction portion comprises the heavy and light chain variable regions of the antibody produced by the hybridoma deposited at the ATCC under Accession Number PTA-122644 [BB2] or Accession Number PTA-122645 [BB7].

4. The detection device of claim 1, wherein the monoclonal antibody or antigen-binding fragment thereof in the reagent portion and/or the reaction portion comprises the heavy and light chains of the antibody produced by the hybridoma deposited at the ATCC under Accession Number PTA-122644 [BB2] or Accession Number PTA-122645 [BB7].

5. The detection device of claim 1, wherein the monoclonal antibody or antigen-binding fragment thereof in the reagent portion and/or the reaction portion is capable of binding to the bed bug antigen in a lysate of whole bed bugs or an extract of collection paper comprising bed bug waste material.

6. The detection device of claim 1, wherein the monoclonal antibody or antigen-binding fragment thereof in the reagent portion comprises the antibody produced by the hybridoma deposited at the ATCC under Accession Number PTA-122644 [BB2], or an antigen-binding fragment thereof.

7. The detection device of claim 1, wherein the monoclonal antibody or antigen-binding fragment thereof in the reagent portion comprises the antibody produced by the hybridoma deposited at the ATCC under Accession Number PTA-122645 [BB7], or an antigen-binding fragment thereof.

8. The detection device of claim 1, wherein the monoclonal antibody or antigen-binding fragment thereof in the reaction portion comprises the antibody produced by the hybridoma deposited at the ATCC under Accession Number PTA-122644 [BB2], or an antigen-binding fragment thereof.

9. The detection device of claim 1, wherein the monoclonal antibody or antigen-binding fragment thereof in the reaction portion comprises the antibody produced by the hybridoma deposited at the ATCC under Accession Number PTA-122645 [BB7], or an antigen-binding fragment thereof.

10. The detection device of claim 1, wherein the monoclonal antibody or antigen-binding fragment thereof in the reagent portion comprises the antibody produced by the hybridoma deposited at the ATCC under Accession Number PTA-122644 [BB2], or an antigen-binding fragment thereof, and the monoclonal antibody or antigen-binding fragment thereof in the reaction portion comprises the antibody produced by the hybridoma deposited at the ATCC under Accession Number PTA-122645 [BB7], or an antigen-binding fragment thereof.

11. The detection device of claim 1, wherein the monoclonal antibody or antigen-binding fragment thereof in the reagent portion comprises the antibody produced by the hybridoma deposited at the ATCC under Accession Number PTA-122645 [BB7], or an antigen-binding fragment thereof, and the monoclonal antibody or antigen-binding fragment thereof in the reaction portion comprises the antibody produced by the hybridoma deposited at the ATCC under Accession Number PTA-122644 [BB2], or an antigen-binding fragment thereof.

12. The detection device of claim 1, wherein the colored particle in the reagent portion is selected from the group consisting of colloidal gold, latex microspheres, and fluorescent particles.

13. A kit comprising the detection device of claim 1 and directions for performing assays with the detection device.

14. A method for analyzing a test fluid to determine prior or present infestations of bed bugs, comprising contacting the test fluid with the test strip of the detection device of claim 1.

* * * * *